United States Patent
Sakai et al.

(10) Patent No.: US 10,428,014 B2
(45) Date of Patent: Oct. 1, 2019

(54) BASE GENERATOR, BASE-REACTIVE COMPOSITION CONTAINING SAID BASE GENERATOR, AND BASE GENERATION METHOD

(71) Applicants: FUJIFILM Wako Pure Chemical Corporation, Osaka (JP); TOKYO UNIVERSITY OF SCIENCE FOUNDATION, Tokyo (JP)

(72) Inventors: Nobuhiko Sakai, Kawagoe (JP); Kosuke Yanaba, Kawagoe (JP); Koji Arimitsu, Tokyo (JP)

(73) Assignees: FUJIFILM Wako Pure Chemical Corporation, Osaka (JP); Tokyo University of Science Foundation, Tokyo (JP)

( * ) Notice: Subject to any disclaimer, the term of this patent is extended or adjusted under 35 U.S.C. 154(b) by 430 days.

(21) Appl. No.: 14/901,525

(22) PCT Filed: Jun. 25, 2014

(86) PCT No.: PCT/JP2014/066912
§ 371 (c)(1),
(2) Date: Dec. 28, 2015

(87) PCT Pub. No.: WO2014/208632
PCT Pub. Date: Dec. 31, 2014

(65) Prior Publication Data
US 2016/0122292 A1  May 5, 2016

(30) Foreign Application Priority Data

Jun. 28, 2013 (JP) ................................. 2013-137489

(51) Int. Cl.
| | |
|---|---|
| *C07C 279/26* | (2006.01) |
| *B01J 19/12* | (2006.01) |
| *C07D 311/86* | (2006.01) |
| *C07C 59/84* | (2006.01) |
| *C07C 65/28* | (2006.01) |
| *C07D 209/48* | (2006.01) |
| *G03F 7/004* | (2006.01) |

(52) U.S. Cl.
CPC .......... *C07C 279/26* (2013.01); *B01J 19/123* (2013.01); *B01J 19/127* (2013.01); *B01J 19/128* (2013.01); *C07C 59/84* (2013.01); *C07C 65/28* (2013.01); *C07D 209/48* (2013.01); *C07D 311/86* (2013.01); *G03F 7/0045* (2013.01); *C07C 2601/14* (2017.05); *C07C 2603/24* (2017.05)

(58) Field of Classification Search
None
See application file for complete search history.

(56) References Cited

U.S. PATENT DOCUMENTS

| | | | |
|---|---|---|---|
| 2,768,205 A | | 10/1956 | Hechenbleikner et al. |
| 3,113,026 A | * | 12/1963 | Sprung ............... C07C 279/26 562/512 |
| 3,261,809 A | | 7/1966 | Sherr |
| 3,272,863 A | * | 9/1966 | Cutler ................ C07C 317/42 562/467 |
| 4,333,929 A | | 6/1982 | Cantello |
| 2006/0009643 A1 | | 1/2006 | Pleschke et al. |
| 2011/0015304 A1 | | 1/2011 | Gaud et al. |

FOREIGN PATENT DOCUMENTS

| | | |
|---|---|---|
| FR | 2796940 | 2/2001 |
| JP | 56118057 | 9/1981 |
| JP | 59106994 | 6/1984 |
| JP | 09278738 | 10/1997 |
| JP | 09292712 | 11/1997 |
| JP | 2006022105 | 1/2006 |
| JP | 2011515553 | 5/2011 |
| JP | 2011236416 | 11/2011 |
| JP | 2012131936 | 7/2012 |
| JP | 2012250969 | 12/2012 |

OTHER PUBLICATIONS

G. Gelbard and F. Vielfaure-Joly, "Polynitrogen Strong Bases: 1-New Syntheses of Biguandides and their Catalytic Properties in Transesterification Reactions," Tetrahedron Letters 39 (1998), p. 2743-2746.

(Continued)

*Primary Examiner* — Ana Z Muresan
(74) *Attorney, Agent, or Firm* — Hamre, Schumann, Mueller & Larson, P.C.

(57) ABSTRACT

The present invention relates to a compound represented by the general formula (A), a base generator comprising the compound, a base-reactive composition which comprises the base generator and a base-reactive compound, as well as a method for generating a base, etc.

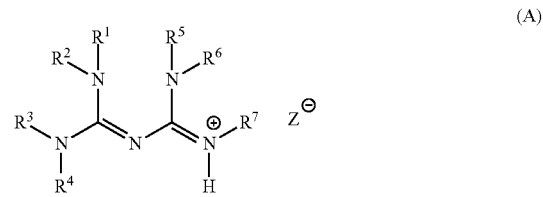

(A)

8 Claims, No Drawings

(56) References Cited

OTHER PUBLICATIONS

S. Hassoon et al., "Photochemistry of (Benzophenonylmethyl)-tri-n-butylammonium Triphenylbutyrlborate: Inter- and Intra-Ion-Pair Electron Transfer Photoreduction," J. Am. Chem. Soc. 117 (1995), p. 11369-11370.

K. Ito et al., "Thermal Crosslinking of Poly(glycidyl methacrylate) Films and Epoxy Resin Films Using Amines Formed by Photolysis of O-acyloximes," Journal of Polymer Science: Part A: Polymer Chemistry, vol. 32 (1994), p. 1793-1796.

J. C. Jochims et al., "Amino-substituted 2-Azaallenium Salts," Chem. Ber. 117 (1984) p. 1900-1912.

X. Sun et al., Bicyclic Guanidinium Tetraphenylborate: A Photobase Generator and A Photocatalyst for Living Anionic Ring-Opening Polymerization and Cross-Linking of Polymeric Materials Containing Ester and Hydroxy Groups, J. Am. Chem. Soc. 130 (2008), p. 8130-8131.

\* cited by examiner

BASE GENERATOR, BASE-REACTIVE COMPOSITION CONTAINING SAID BASE GENERATOR, AND BASE GENERATION METHOD

TECHNICAL FIELD

The present invention relates to a base generator, etc. to be used in a resist field, etc., and for more detail, relates to a compound having a property generating biguanides, as a strong base, by irradiation of active energy ray, a base generator comprising these, a base-reactive composition comprising the base generator, and a method for generating a base.

BACKGROUND ART

Curing (hereafter, it may be abbreviated as photo-curing) by a polymerization initiator (hereafter, it may be abbreviated as a photo-polymerization initiator) sensitive to active energy ray, such as, for example, infrared rays, visible rays, ultraviolet rays, X-rays, has many advantages, such that it is possible to cure at lower temperature and in a shorter period of time, and to form finer patterns, etc., as compared with curing (hereafter, it may be abbreviated as heat-curing) by a heat sensitive polymerization initiator (hereafter, it may be abbreviated as a thermal-polymerization initiator), therefore, these photo-polymerization initiators have been used, as photo-curing materials, widely in the fields of surface processing of a paint, a printing ink, a dental material, a resist, etc.

The photo-polymerization initiators to be used in photo-curing technology are largely classified into three groups of photo-radical generators, a photo-cation (acid) generator and a photo-anion (base) generator, depending on the active species generated. The photo-radical generator is a photo-polymerization initiator for generating radical species by irradiation of the active energy ray, and it is the generator which has been used widely in the past, however, it has the drawbacks that the radical species are deactivated by oxygen in air, a polymerization reaction is inhibited and curing is suppressed. Therefore, in using the photo-radical generator, special contrivance has been required, such that oxygen in air is intercepted. The photo-cation (acid) generator is a photo-polymerization initiator, which generates an acid by irradiation of active energy ray and thus does not receive inhibition by oxygen, therefore various kinds of the photo-cation (acid) generators have been provided to practical use since the latter half of 1990's. However, there may be the case where the acid generated by irradiation of the active energy ray remains in a system even after curing, and there have been pointed out a problem of decrease in film performance, caused by denaturation of a cured film after curing of a photo-sensitive composition containing the photo-cation (acid) generator, or a problem of corrosive property to a metal wiring on a semiconductor substrate, caused by the acid. In contrast, the photo-anion (base) generator is the generator which generates a base by irradiation of active energy ray, and thus does not receive inhibition by oxygen in air, and a problem of corrosive property or denaturation of a cured film hardly occurs, therefore research and development thereof has been actively carried out in recent years.

Recently, there has been investigated a means for applying the photo-sensitive composition containing the photo-anion (base) generator to a photo-resist material or a photo-curing material, etc. For example, there has been proposed a method in which amines are generated in an epoxy resin by irradiation of active energy ray, and subsequently the epoxy resin is cured by heating treatment, by utilizing that, for example, a compound having an epoxy group cures by generating a cross-linking reaction by an action of a base (for example, NON PATENT LITERATURE 1).

In the case of curing an epoxy-based compound by amines generating from the photo-anion (base) generator, a primary amine or a secondary amine requires a long period of time for a cross-linking reaction with an epoxy group, therefore, it is necessary to carry out heating treatment, etc. at high temperature, in order to increase cure rate. In addition, it is also possible to increase cure rate by increasing a crosslinking density with using a polyfunctionalized primary amine or secondary amine, however, it is necessary for all amines to be made photo-latent (protected), and solubility is likely to be reduced significantly. In contrast, when the epoxy-based compound is cured by amines, such as a tertiary amine, amidine, guanidine, phosphazene, these amines easily function as a catalyst, and thus can cure the epoxy-based compound, even by using relatively less amount, and particularly in combined use with a cross-linking agent (for example, polyfunctional carboxylic acid, polyfunctional phenol, polyfunctional thiol, polyfunctional β-ketoester, etc.) having an acidic proton, it can cure the epoxy-based compound at low temperature and quickly.

As such amines, there have been known conventionally a photo-anion (base) generator, such as, for example, a tertiary amine, an amine-imide-based compound (for example, PATENT LITERATURE 1) which generate amidine, such as 1,5-diazabicyclo[4.3.0]-5-nonene (DBN), 1,8-diazabicyclo [5.4.0]-7-undecene (DBU) by irradiation of active energy rays, and an ammonium borate-based compound (for example, NON PATENT LITERATURE 2). In addition, there have been known a photo-anion (base) generator, such as a tetraphenyl borate-based compound (for example, NON PATENT LITERATURE 3) which generates a strong base, such as guanidine, such as 1,1,3,3-tetramethylguanidine (TMG), 1,5,7-triazabicyclo[4.4.0]deca-5-ene (TBD), 7-methyl-1,5,7-triazabicyclo[4.4.0]deca-5-ene (MTBD), or phosphazene, for example, by irradiation of active energy rays; a compound (for example, PATENT LITERATURE 2) comprising a carboxylic acid, which is decarboxylated by irradiation of active energy rays, and amines; a benzoic acid-based compound (for example, PATENT LITERATURE 3) forming a cyclic ester by irradiation of active energy rays. On the other hand, as a strong organic base exceeding amidine or guanidine, biguanides have been known (for example, PATENT LITERATURE 4, NON PATENT LITERATURE 4, NON PATENT LITERATURE 5), and an example where the biguanides are used for epoxy curing application has also been reported (for example, PATENT LITERATURE 5). In addition, such an application example has been known as a potential heat-curing catalyst by formation of a salt between a thermally decomposable compound and biguanides, although it is not as the photo-anion (base) generator (for example, PATENT LITERATURE 6, PATENT LITERATURE 7).

CITATION LIST

Patent Literature

PATENT LITERATURE 1: JP-A-2012-131936
PATENT LITERATURE 2: JP-A-2011-236416
PATENT LITERATURE 3: JP-A-2012-250969
PATENT LITERATURE 4: U.S. Pat. No. 2,768,205

PATENT LITERATURE 5: U.S. Pat. No. 3,261,809
PATENT LITERATURE 6: JP-A-9-278378
PATENT LITERATURE 7: JP-A-9-292712

Non Patent Literature

NON PATENT LITERATURE 1: J. Polym. Sci., Part A: Polym. Chem., 32, 1793 (1994)
NON PATENT LITERATURE 2: J. Am. Chem. Soc., 117, 11369 (1995)
NON PATENT LITERATURE 3: J. Am. Chem. Soc., 130, 8130 (2008)
NON PATENT LITERATURE 4: Tetrahedron Lett., 39, 2743 (1998)
NON PATENT LITERATURE 5: Chem. Ber. 117, 1900-1912 (1984)

SUMMARY OF INVENTION

Technical Problem

According to a curing process by using of a photo-sensitive composition containing these photo-anion (base) generators, it has been said to be able to cure a resin material, such as, for example, an epoxy-based compound, a silicon-based compound, by effects of a base generating from the photo-anion (base) generators.

However, the above-described photo-anion (base) generator is generally a solid in many cases, and most of them are not soluble sufficiently to an organic solvent, and it has particularly poor solubility to an organic solvent generally used in this field, such as a glycol-based solvent, such as, for example, propylene glycol monomethyl ether (PGME), propylene glycol monomethyl ether acetate (PGMEA), an ester-based solvent, such as, for example, ethyl lactate (EL). Therefore, in the case of attempting to prepare a cured film by dissolving the photo-sensitive composition containing these photo-anion (base) generators into the above-described organic solvent, there is a problem of decrease in contrast between an exposed area (cured area) and an unexposed area (uncured area), because only trace amount of the photo-anion (base) generator can be used, or on the contrary, in using a large amount of the photo-anion (base) generator, aiming at improving the contrast, the photo-anion (base) generator results in to be precipitated as a solid. In addition, recently, such a curing process has been required for preparing a cured film by directly dissolving the photo-anion (base) generator into a base-reactive compound, such as a monomer or an oligomer, by decreasing use amount of the organic solvent as less as possible, or without using the organic solvent, intending low environmental load, however, a conventional photo-anion (base) generator, which generates a strong base, has a problem of difficulty in progressing a reaction in good efficiency, due to having poor compatibility with the base-reactive compound.

In addition, in the case of the photo-anion (base) generator composed of, for example, a carboxylic acid and amines, although there exists an oily compound not causing a problem of solubility to an organic solvent, depending on combination of these, there is a problem that such a photo-anion (base) generator generally has poor potential of a base, lacks storage stability, and has low heat resistance. As the base (amines) generating, such amines is preferable that indicates strong basicity and heat resistance, as well as functions as a catalyst with low nucleophilicity and degree of freedom without being incorporated in a polymer (resin). Under such a background, development of such photo-anion (base) generator has been desired that has high solubility to various organic solvents and a base-reactive compound, and is provided with both performance of high heat resistance and low nucleophilicity, and generates a strong base.

The present invention has been made in view of the above-described circumstances, and it is an object of the present invention to provide a base generator which has high solubility to general-purpose organic solvents, and also can dissolve directly into a base-reactive compound, such as an epoxy-based compound, and is provided with both performance of high heat resistance and low nucleophilicity, and generates a strong base; a base-reactive composition comprising the base generator and the base-reactive compound; as well as a method for generating a base.

Solution to Problem

The present invention is composed of the following constitution.

(1) A compound represented by the general formula (A).

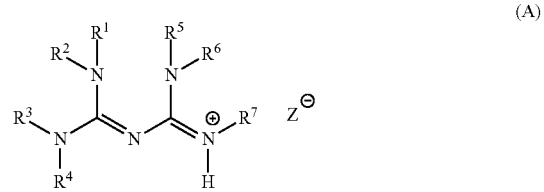

(A)

(wherein $R^1$ to $R^5$ each independently represent a hydrogen atom; an alkyl group having 1 to 12 carbon atoms; an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group; or an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group, $R^6$ represents a hydrogen atom; an alkyl group having 1 to 12 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group; an alkenyl group having 2 to 12 carbon atoms; an alkynyl group having 2 to 12 carbon atoms; an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group; or an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group, $R^7$ represents a hydrogen atom; an alkyl group having 1 to 12 carbon atoms which may have an amino group; an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group; or an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group, and $Z^-$ represents an anion derived from a carboxylic acid represented by the general formula ($B_1$), ($B_2$), ($B_3$) or ($B_4$).)

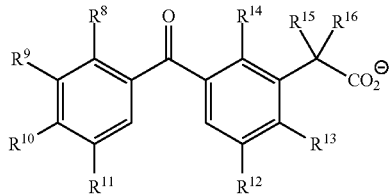
($B_1$)

(wherein $R^8$ to $R^{16}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom or a nitro group.)

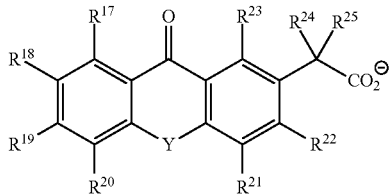
($B_2$)

(wherein $R^{17}$ to $R^{25}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom or a nitro group, and Y represents an oxygen atom or a sulfur atom.)

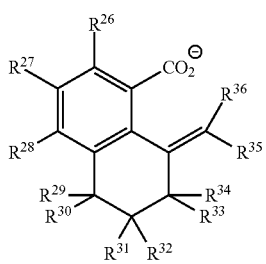
($B_3$)

(wherein $R^{26}$ to $R^{36}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom or a nitro group, and two pieces of R may form a ring structure by binding to each other.)

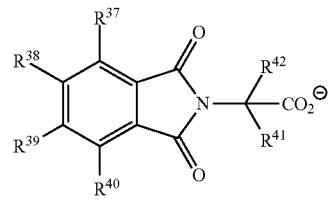
($B_4$)

(wherein $R^{37}$ to $R^{42}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom or a nitro group, and two pieces of R may form a ring structure by binding to each other.)

(2) A base generator comprising the compound represented by the above-described general formula (A).

(3) A base-reactive composition, which comprises the base generator comprising the compound represented by the above-described general formula (A) and a base-reactive compound.

(4) A method for generating a base, which comprises irradiating active energy ray to the compound represented by the above-described general formula (A).

(5) A compound represented by the general formula ($C_1$) or ($C_2$).

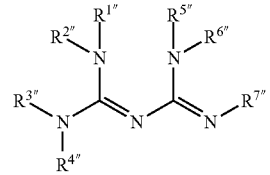
($C_1$)

(wherein $R^{1''}$ to $R^{4''}$ each independently represent an alkyl group having 1 to 8 carbon atoms, $R^{5''}$ represents an alkyl group having 2 to 8 carbon atoms, $R^{6''}$ represents an alkyl group having 1 to 6 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group; an alkenyl group having 2 to 6 carbon atoms; or an arylalkyl group having 7 to 15 carbon atoms which may have a substituent selected form the group consisting of an alkyl group having 1 to 6 carbon atoms, an alkoxy group having 1 to 6 carbon atoms, a halogen atom and a nitro group, and $R^{7''}$ represents an alkyl group having 2 to 8 carbon atoms which may have an amino group.)

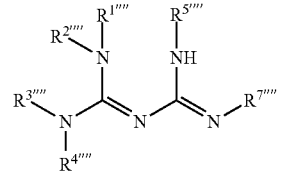
($C_2$)

(wherein $R^{1''''}$ to $R^{4''''}$ each independently represent an alkyl group having 1 to 8 carbon atoms, $R^{5''''}$ represents an alkyl group having 1 to 10 carbon atoms; or an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group, and $R^{7''''}$ represents an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group.)

Advantageous Effects of Invention

The compound represented by the general formula (A) of the present invention is a compound by formation of a salt between a carboxylic acid having a specific structure and biguanides, and is a compound which generates a strong base (biguanides) by irradiation of active energy ray. These compounds exert effect of high general-purpose as the base generator, because of having high solubility to various organic solvents and a base-reactive compound, and having both performance of high heat resistance and low nucleophilicity.

The base generator of the present invention has high solubility to a base-reactive compound, and is capable of containing a large amount of the base generator in a composition containing the base-reactive compound, therefore exerts effect of enabling to generate a large amount of a strong base (biguanides) in the composition, by irradiation of active energy ray.

The base-reactive composition of the present invention progresses a polymerization reaction of the base-reactive compound, using a strong base (biguanides) generated from the base generator in the base-reactive composition of the present invention by irradiation of active energy ray, as an initiator, and not only makes curing of the base-reactive compound progress effectively, but also is able to make a large amount of the base generator contain in the composition, and as a result, exerts effect of providing patterns having high contrast between an exposed area (cured area) and an unexposed area (uncured area). In addition, the following effect is exerted by pattern formation by making the glycol ether acetate-based solvent or the ester-based solvent contain into the base-reactive composition of the present invention. That is, there are the following effects, (1) these solvents have suitable boiling point, therefore not only preparation of the composition, which is usually carried out at normal temperature, can be carried out stably but also the base generator and the base-reactive compound little receive adverse influence by heat, because high baking temperature is not necessary in pre-baking, (2) these solvents have good compatibility with a substrate and good flatting of the composition in spin coating, therefore the composition can be coated onto a substrate simply and conveniently, (3) these solvents have higher solubility of the base generator, as compared with other solvents, therefore phase separation of the base generator is difficult to be caused, and (4) these solvents have good stability without indicating basicity due to the decomposing material, different from the amide-based solvent, etc.

The method for generating a base of the present invention is a method for generating a base by irradiating active energy ray to the compound represented by the general formula (A) of the present invention, and exerts effect that a strong base (biguanides) can be generated more efficiently from the compound represented by the general formula (A) of the present invention, as compared with a method for generating a base by heat energy.

The present inventors have intensively studied a way to achieve the above-described objects and as a result, by focusing on that pKa of biguanides is 31.8, while pKa of DBU, which is a kind of amidines known as an organic strong base, is 24.3, and pKa of TBD, which is a kind of guanidines, is 26.0, and by combining biguanides, which are such a strong base, and a carboxylic acid having a specific structure and having high sensitivity to active energy ray, found that not only a strong base can be generated by irradiation of active energy ray, but also a base generator, having high heat resistance and good solubility to an organic solvent and a base-reactive compound, is obtained, and have thus completed the present invention.

DESCRIPTION OF EMBODIMENTS

In the present invention, active energy ray include, excluding the case where a wavelength is specified, not only an electromagnetic wave (visible rays) having a wavelength of a visible region, but also, for example, an electromagnetic wave (ultraviolet rays) having a wavelength of an ultraviolet region, an electromagnetic wave (infrared rays), having a wavelength of an infrared region, and an electromagnetic wave having a wavelength of a non-visible region, such as X-rays. In the present invention, there may be the case where a base generator sensitive to active energy ray (a base generator which generates a base by irradiation of active energy ray) is called a photo base generator. In addition, there may be the case where active energy ray, having a wavelength of 365 nm, 405 nm and 436 nm, may be written as i-rays, h-rays and g-rays, respectively.

—A Compound Represented by the General Formula (A) of the Present Invention—

The compound of the present invention is a compound represented by the following general formula (A).

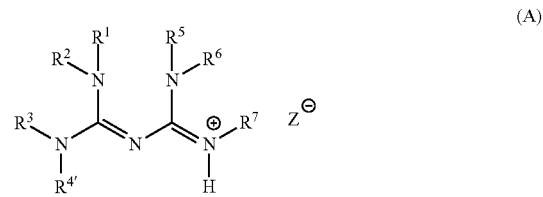

(wherein $R^1$ to $R^5$ each independently represent a hydrogen atom; an alkyl group having 1 to 12 carbon atoms; an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group; or an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group, $R^6$ represents a hydrogen atom; an alkyl group having 1 to 12 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group; an alkenyl group having 2 to 12 carbon atoms; an alkynyl group having 2 to 12 carbon atoms; an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group; or an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group, $R^7$ represents a hydrogen atom; an alkyl group having 1 to 12 carbon atoms which may have an amino group; an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group; or an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group, and $Z^-$ represents an anion derived from a carboxylic acid represented by the general formula ($B_1$), ($B_2$), ($B_3$) or ($B_4$).)

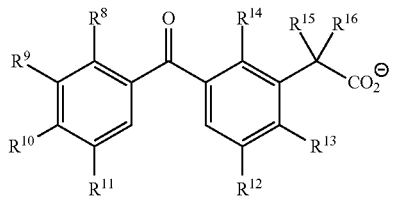

(B$_1$)

(wherein $R^8$ to $R^{16}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom or a nitro group.)

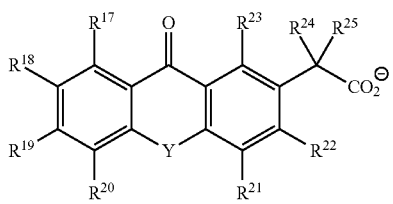

(B$_2$)

(wherein $R^{17}$ to $R^{25}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom or a nitro group, and Y represents an oxygen atom or a sulfur atom.)

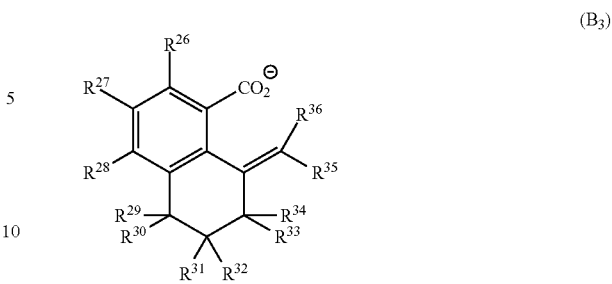

(B$_3$)

(wherein $R^{26}$ to $R^{36}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom or a nitro group, and two pieces of R may form a ring structure by binding to each other.)

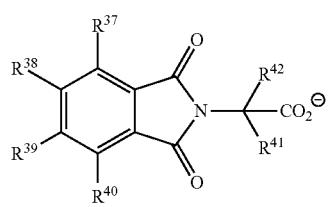

(B$_4$)

(wherein $R^{37}$ to $R^{42}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom or a nitro group, and two pieces of R may form a ring structure by binding to each other.)

An alkyl group having 1 to 12 carbon atoms represented by $R^1$ to $R^5$ and $R^8$ to $R^{42}$ in the general formulae (A), (B$_1$), (B$_2$), (B$_3$) and (B$_4$) may be any of a straight chained, branched or cyclic group, and specifically includes, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a n-nonyl group, an isononyl group, a sec-nonyl group, a tert-nonyl group, a neononyl group, a cyclononyl group, a n-decyl group, an isodecyl group, a sec-decyl group, a tert-decyl group, a neodecyl group, a cyclodecyl group, a n-undecyl group, a cycloundecyl group, a n-dodecyl group, a cyclododecyl group, a norbornyl group (a norbornane-χ-yl group), a bornyl group (a bornane-χ-yl group), a menthyl group (a mentha-χ-yl group), an adamantyl group, a decahydronaphthyl group, etc.

Among these alkyl groups, in $R^1$ to $R^4$ of the general formula (A), the straight chained, branched, or cyclic alkyl group having 1 to 8 carbon atoms, such as, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a norbornyl group (a norbornane-χ-yl group), is preferable, among them, the straight chained, branched, or cyclic alkyl group having 1 to 4 carbon atoms, such as, for example, a methyl group, an ethyl group, a n-propyl group, an isopropyl group, a n-butyl group, an isobutyl group, a sec-butyl group, a tert-butyl group, a cyclobutyl group, is more preferable, and among them, a methyl group, which is an alkyl group having one carbon atom, is still more preferable. In $R^5$, the straight chained, branched, or cyclic alkyl group having 1 to 10 carbon atoms, such as, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, 2-ethylhexyl group, a cyclooctyl group, a n-nonyl group, an isononyl group, a sec-nonyl group, a tert-nonyl group, a neononyl group, a cyclononyl group, a n-decyl group, an isodecyl group, a sec-decyl group, a tert-decyl group, a neodecyl group, a cyclodecyl group, a norbornyl group (a norbornane-χ-yl group), a bornyl group (a bornane-χ-yl group), a menthyl group (a mentha-χ-yl group), an adamantyl group, a decahydronaphthyl group, is preferable, among them, the straight chained, branched, or cyclic alkyl group having 1 to 8 carbon atoms, such as, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a norbornyl group (a norbornane-χ-yl group), is more preferable, and among them, for example, the straight chained, branched, or cyclic alkyl group having 2 to 8 carbon atoms, such as, for example, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a norbornyl group (a norbornane-χ-yl group), is still more preferable.

Among the above-described alkyl groups, in $R^8$ to $R^{42}$ of the general formulae $(B_1)$, $(B_2)$, $(B_3)$ and $(B_4)$, the straight chained, branched, or cyclic alkyl group having 1 to 4 carbon atoms, such as, for example, a methyl group, an ethyl group, a n-propyl group, an isopropyl group, a n-butyl group, an isobutyl group, a sec-butyl group, a tert-butyl group, a cyclobutyl group, is preferable, and among them, a methyl group, which is an alkyl group having one carbon atom, is still more preferable.

An aryl group having 6 to 14 carbon atoms, in "an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group", represented by $R^1$ to $R^7$ in the general formula (A), may be any of a mono cyclic or a condensed polycyclic group, and specifically includes, for example a phenyl group, a naphthyl group, an anthracenyl group (an anthryl group), a phenanthrenyl group (a phenanthryl group), etc., among them, an aryl group having 6 to 10 carbon atoms, such as, for example, a phenyl group, a naphthyl group, is preferable, and among them, a phenyl group which is an aryl group having 6 carbon atoms is more preferable. It should be noted that number of the carbon atoms in the aryl group shown here means number of the carbon atoms constituting the aryl group, and number of the carbon atoms constituting a substituent is not contained in number of the carbon atoms represented by the "6 to 14 carbon atoms".

An alkyl group having 1 to 6 carbon atoms in "an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group", represented by $R^1$ to $R^7$ in the general formula (A), means an alkyl group having 1 to 6 carbon atoms binding to carbon atom on the aryl group, and specific examples thereof include, for example, a methyl group, an ethyl group, a n-propyl group, an isopropyl group, a n-butyl group, an isobutyl group a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, etc., and among them, an alkyl group having 1 to 4 carbon atoms, such as, for example, a methyl group, an ethyl group, a n-propyl group, an isopropyl group, a n-butyl group, an isobutyl group, a sec-butyl group, a tert-butyl group, a cyclobutyl group, is preferable.

An alkoxy group having 1 to 6 carbon atoms in "an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group", represented by $R^1$ to $R^7$ in the general formula (A), means an alkoxy group having 1 to 6 carbon atoms binding to carbon atom on the aryl group, and specific examples thereof include, for example, a methoxy group, an ethoxy group, a n-propoxy group, an isopropoxy group, a n-butoxy group, an isobutoxy group, a sec-butoxy group, a tert-butoxy group, a cyclobutoxy group, a n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, a n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, a cyclohexyloxy group, etc., and among them, an alkoxy group having 1 to 4 carbon atoms, such as, for example, a methoxy group, an ethoxy group, a n-propoxy group, an isopropoxy group, a n-butoxy group, an isobutoxy group, a sec-butoxy group, a tert-butoxy group, a cyclobutoxy group, is preferable.

A halogen atom in "an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group", represented by $R^1$ to $R^7$ in the general formula (A), means a halogen atom binding to carbon atom on the aryl group, and specific examples thereof include, for example, a fluorine atom, a chlorine atom, a bromine atom, an iodine atom, etc., and among them, a chlorine atom and a bromine atom are preferable.

A nitro group in "an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group", represented by $R^1$ to $R^7$ in the general formula (A), means a nitro group binding to carbon atom on the aryl group.

Among the substituents in "an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group", represented by $R^1$ to $R^7$ in the general formula (A), an alkyl group having 1 to 6 carbon atoms, and an alkoxy group having 1 to 6 carbon atoms are preferable.

An aryl group having 6 to 14 carbon atoms represented by $R^8$ to $R^{42}$ in the general formulae $(B_1)$, $(B_2)$, $(B_3)$ and $(B_4)$ may be any of a monocyclic or condensed polycyclic group, and specifically includes, for example, a phenyl group, a naphthyl group, an anthracenyl group (an anthryl group), a phenanthrenyl group (a phenanthryl group), etc., among them, an aryl group having 6 to 10 carbon atoms, such as, for example, a phenyl group, a naphthyl group, is preferable, and among them, a phenyl group, which is an aryl group having 6 carbon atoms, is more preferable.

An arylalkyl group having 7 to 15 carbon atoms in "an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group", represented by $R^1$ to $R^7$ in the general formula (A), may be any of a monocyclic or condensed polycyclic group, and specifically includes, for example, a benzyl group, a phenethyl group, a methylbenzyl group, a phenylpropyl group, a 1-methylphenylethyl group, a phenylbutyl group, a 2-methylphenylpropyl group, a tetrahydronaphthyl group, a naphthylmethyl group, a naphthylethyl group, an indenyl group, a fluorenyl group, an anthracenylmethyl group (an anthrylmethyl group), a phenanthrenylmethyl group (a phenanthrylmethyl group), etc. It should be noted that number of the carbon atoms of the arylalkyl group shown here means number of the carbon atoms constituting the arylalkyl group, and number of the carbon atoms constituting a substituent is not contained in number of the carbon atoms represented by the "7 to 15 carbon atoms".

Among these arylalkyl groups, in $R^1$ to $R^5$, $R^7$, a benzyl group, which is an arylalkyl group having 7 carbon atoms, is preferable.

Among these arylalkyl groups, in $R^6$, a benzyl group, and an anthracenylmethyl group (an anthrylmethyl group) are preferable.

An alkyl group having 1 to 6 carbon atoms in "an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group", represented by $R^1$ to $R^7$ in the general formula (A), means an alkyl group having 1 to 6 carbon atoms binding to carbon atom on an aryl group, and specific examples thereof include, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, etc., and among them, an alkyl group having 1 to 4 carbon atoms, such as, for example, a methyl group, an ethyl group, a n-propyl group, an isopropyl group, a n-butyl group, an isobutyl group, a sec-butyl group, a tert-butyl group, a cyclobutyl group, is preferable.

An alkoxy group having 1 to 6 carbon atoms in "an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group", represented by $R^1$ to $R^7$ in the general formula (A), means an alkoxy group having 1 to 6 carbon atoms binding to carbon atom on an aryl group, and specific examples thereof include, for example, a methoxy group, an ethoxy group, a n-propoxy group, an isopropoxy group, a n-butoxy group, an isobutoxy group, a sec-butoxy group, a tert-butoxy group, a cyclobutoxy group, a n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, a n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, an cyclohexyloxy group, etc., and among them, an alkoxy group having 1 to 4 carbon atoms, such as, for example, a methoxy group, an ethoxy group, a n-propoxy group, an isopropoxy group, a n-butoxy group, an isobutoxy group, a sec-butoxy group, a tert-butoxy group, a cyclobutoxy group, is preferable.

A halogen atom in "an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group", represented by $R^1$ to $R^7$ in the general formula (A), means a halogen atom binding to carbon atom on an aryl group, and specific examples thereof include, for example, a fluorine atom, a chlorine atom, a bromine atom, an iodine atom, etc., and among them, a chlorine atom and a bromine atom are preferable.

A nitro group in "an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group", represented by $R^1$ to $R^7$ in the general formula (A), means a nitro group binding to carbon atom on an aryl group.

Among the substituents in "an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group", represented by $R^1$ to $R^7$ in the general formula (A), an alkyl group having 1 to 6 carbon atoms, and an alkoxy group having 1 to 6 carbon atoms are preferable.

An arylalkyl group having 7 to 15 carbon atoms, represented by $R^8$ to $R^{42}$ in the general formulae ($B_1$), ($B_2$), ($B_3$) and ($B_4$), may be any of a monocyclic or condensed polycyclic group, and specifically includes, for example, a benzyl group, a phenethyl group, a methylbenzyl group, a phenylpropyl group, a 1-methylphenylethyl group, a phenylbutyl group, a 2-methylphenylpropyl group, a tetrahydronaphthyl group, a naphthylmethyl group, a naphthylethyl group, an indenyl group, a fluorenyl group, an anthracenylmethyl group (an anthrylmethyl group), a phenanthrenylmethyl group (a phenanthrylmethyl group), etc., and among them, a benzyl group, which is an alkyl group having 7 carbon atoms, is preferable.

An alkyl group having 1 to 12 carbon atoms in "an alkyl group having 1 to 12 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group" represented by $R^6$ in the general formula (A), may be any of a straight chained, branched, or cyclic group, and specifically, includes, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a n-nonyl group, an isononyl group, a sec-nonyl group, a tert-nonyl group, a neononyl group, a cyclononyl group, a n-decyl group, an isodecyl group, a sec-decyl group, a tert-decyl group, a neodecyl group, a cyclodecyl group, a n-undecyl group, a cycloundecyl group, n-dodecyl group, a cyclododecyl group, a norbornyl group (a norbornane-χ-yl group), a bornyl group (a bornane-χ-yl group), a menthyl group (a mentha-χ-yl group), an adamantyl group, a decahydronaphthyl group, etc., among them, an alkyl group having 1 to 6 carbon atoms, which is the straight chained, branched, or cyclic alkyl group, such as, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, is preferable, and among them, an alkyl group having 1 to 4 carbon atoms which is the straight chained, branched or cyclic alkyl group, for example, a methyl group, an ethyl group, a n-propyl group, an isopropyl group, a n-butyl group, an isobutyl group, a sec-butyl group, a tert-butyl group, a cyclobutyl group, etc., are more preferable. It should be noted that number of the carbon atoms of the alkyl group shown here means number of the carbon atoms constituting the alkyl group, and number of the carbon atoms constituting a substituent is not contained in number of the carbon atoms represented by the "1 to 12 carbon atoms".

An alkoxycarbonyl group having 2 to 6 carbon atoms in "an alkyl group having 1 to 12 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group" represented by $R^6$ in the general formula (A), may be any of a straight chained, branched, or cyclic group, and specifically includes, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a cyclobutoxycarbonyl group, a n-pentyloxycarbonyl group, an isopentyloxycarbonyl group, a sec-pentyloxycarbonyl group, a tert-pentyloxycarbonyl group, a neopentyloxycarbonyl group, a 2-methylbutoxycarbonyl group, a 1,2-dimethylpropoxycarbonyl group, a 1-ethylpropoxycarbonyl group, a cyclopentyloxycarbonyl group, etc., and among them, an alkoxycarbonyl group having 2 to 5 carbon atoms, such as, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a cyclobutoxycarbonyl group, is preferable.

Specific examples of the alkyl group having 1 to 12 carbon atoms having an epoxy group, represented by $R^6$ in the general formula (A), include those represented by, for example, the following general formula ($D_1$).

(wherein $n_1$ pieces of $R^{43}$ and $R^{44}$ each independently represent a hydrogen atom or an alkyl group having 1 to 4 carbon atoms, and $n_1$ represents an integer of 1 to 3, provided that number of carbon atoms of a group constituting $n_1$ pieces of ($R^{43}$—C—$R^{44}$) is 12 or less.)

An alkyl group having 1 to 4 carbon atoms represented by $R^{43}$ and $R^{44}$ in the general formula ($D_1$) may be any of a straight chained, branched, or cyclic group, and specifically includes, for example, a methyl group, an ethyl group, a n-propyl group, an isopropyl group, a n-butyl group, an isobutyl group, a sec-butyl group, a tert-butyl group, a cyclobutyl group, etc., and among them, a methyl group, which is an alkyl group having one carbon atom, is preferable.

As $n_1$ pieces of $R^{43}$ and $R^{44}$ in the general formula ($D_1$), a hydrogen atom is more preferable.

$n_1$ in the general formula ($D_1$) represents usually an integer of 1 to 3, and among them, an integer of 1 to 2 is preferable, and 1 is more preferable.

Number of carbon atoms of a group constituting $n_1$ pieces of ($R^{43}$—C—$R^{44}$) in the general formula ($D_1$) is usually an integer of 12 or less, among them, an integer of 6 or less is preferable, and among them an integer of 4 or less is more preferable, and 1 is particularly preferable.

Specific examples of the alkyl group having 1 to 12 carbon atoms having an alkoxycarbonyl group having 2 to 6 carbon atoms, represented by $R^6$ in the general formula (A), include those represented by, for example, the following general formula ($D_2$).

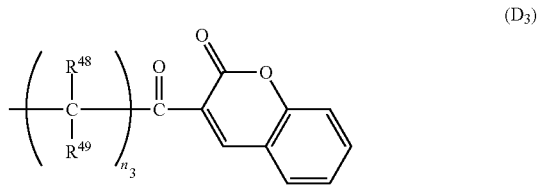

(D₂)

(wherein $n_2$ pieces of $R^{45}$ and $R^{46}$ each independently represent a hydrogen atom or an alkyl group having 1 to 4 carbon atoms, $R^{47}$ represents an alkyl group having 1 to 5 carbon atoms, and $n_2$ represents an integer of 1 to 3, provided that number of carbon atoms of a group constituting $n_2$ pieces of ($R^{45}$—C—$R^{46}$) is 12 or less.)

Specific examples of the alkyl group having 1 to 4 carbon atoms represented by $R^{45}$ and $R^{46}$ in the general formula ($D_2$), include those similar to specific examples of the alkyl group having 1 to 4 carbon atoms represented by $R^{43}$ and $R^{44}$ in the general formula ($D_1$), and also specific examples of the preferable alkyl group include the same.

An alkyl group having 1 to 5 carbon atoms represented by $R^{47}$ in the general formula ($D_2$), may be any of a straight chained, branched, or cyclic group, and specifically includes, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, etc., and among them, an alkyl group having 1 to 4 carbon atoms, such as, for example, a methyl group, an ethyl group, a n-propyl group, an isopropyl group, a n-butyl group, an isobutyl group, a sec-butyl group, a tert-butyl group, a cyclobutyl group, is preferable.

$n_2$ in the general formula ($D_2$) represents usually an integer of 1 to 3, and among them, an integer of 1 to 2 is preferable.

Number of carbon atoms of a group constituting $n_2$ pieces of ($R^{45}$—C—$R^{46}$) in the general formula ($D_2$) is usually an integer of 12 or less, among them, an integer of 6 or less is preferable, and among them an integer of 4 or less is more preferable.

Specific examples of the alkyl group having 1 to 12 carbon atoms having a coumarinylcarbonyl group, represented by $R^6$ in the general formula (A), include those represented by, for example, the following general formula ($D_3$).

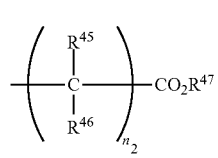

(D₃)

(wherein $n_3$ pieces of $R^{48}$ and $R^{49}$ each independently represent a hydrogen atom or an alkyl group having 1 to 4 carbon atoms, and $n_3$ represents an integer of 1 to 3, provided that number of carbon atoms of a group constituting $n_3$ pieces of ($R^{48}$—C—$R^{49}$) is 12 or less.)

Specific examples of the alkyl group having 1 to 4 carbon atoms represented by $R^{48}$ and $R^{49}$ in the general formula ($D_3$), include those similar to specific examples of the alkyl group having 1 to 4 carbon atoms represented by $R^{43}$ and $R^{44}$ in the general formula ($D_1$), and also specific examples of the preferable alkyl group include the same.

As $n_3$ pieces of $R^{48}$ and $R^{49}$ in the general formula ($D_3$), a hydrogen atom is more preferable.

$n_3$ in the general formula ($D_3$) is an integer similar to $n_1$ in the general formula ($D_1$), and preferable $n_3$ and more preferable $n_3$ are also integers similar to $n_1$.

Number of carbon atoms of a group constituting $n_3$ pieces of ($R^{48}$—C—$R^{49}$) in the general formula ($D_3$) is usually an integer of 12 or less, among them, an integer of 6 or less is preferable, and among them an integer of 4 or less is more preferable, and 1 is particularly preferable.

Specific examples of the alkyl group having 1 to 12 carbon atoms having an anthraquinonyl group, represented by $R^6$ in the general formula (A), include those represented by, for example, the following general formula ($D_4$).

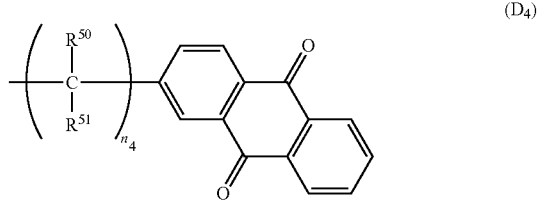

(D₄)

(wherein $n_4$ pieces of $R^{50}$ and $R^{51}$ each independently represent a hydrogen atom or an alkyl group having 1 to 4 carbon atoms, and $n_4$ represents an integer of 1 to 3, provided that number of carbon atoms of a group constituting $n_4$ pieces of ($R^{50}$—C—$R^{51}$) is 12 or less.)

Specific examples of the alkyl group having 1 to 4 carbon atoms represented by $R^{50}$ and $R^{51}$ in the general formula ($D_4$), include those similar to specific examples of the alkyl group having 1 to 4 carbon atoms represented by $R^{43}$ and $R^{44}$ in the general formula ($D_1$), and also specific examples of the preferable alkyl group include the same.

As $n_4$ pieces of $R^{50}$ and $R^{51}$ in the general formula ($D_4$), a hydrogen atom is more preferable.

$n_4$ in the general formula ($D_4$) is an integer similar to $n_1$ in the general formula ($D_1$), and preferable $n_4$ and more preferable $n_4$ are also integers similar to $n_1$.

Number of carbon atoms of a group constituting $n_4$ pieces of ($R^{50}$—C—$R^{51}$) in the general formula ($D_4$) is usually an integer of 12 or less, among them, an integer of 6 or less is preferable, and among them an integer of 4 or less is more preferable.

Specific examples of the alkyl group having 1 to 12 carbon atoms having a xanthonyl group, represented by $R^6$ in the general formula (A), include those represented by, for example, the following general formula ($D_5$).

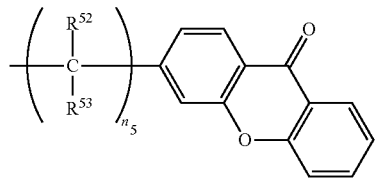

($D_5$)

(wherein $n_5$ pieces of $R^{52}$ and $R^{53}$ each independently represent a hydrogen atom or an alkyl group having 1 to 4 carbon atoms, and $n_5$ represents an integer of 1 to 3, provided that number of carbon atoms of a group constituting $n_5$ pieces of ($R^{52}$—C—$R^{53}$) is 12 or less.)

Specific examples of the alkyl group having 1 to 4 carbon atoms represented by $R^{52}$ and $R^{53}$ in the general formula ($D_5$), include those similar to specific examples of the alkyl group having 1 to 4 carbon atoms represented by $R^{43}$ and $R^{44}$ in the general formula ($D_1$), and also specific examples of the preferable alkyl group include the same.

As $n_5$ pieces of $R^{52}$ and $R^{53}$ in the general formula ($D_5$), a hydrogen atom is more preferable.

$n_5$ in the general formula ($D_5$) is an integer similar to $n_1$ in the general formula ($D_1$), and preferable $n_5$ and more preferable $n_5$ are also integers similar to $n_1$.

Number of carbon atoms of a group constituting $n_5$ pieces of ($R^{52}$—C—$R^{53}$) in the general formula ($D_5$) is usually an integer of 12 or less, among them, an integer of 6 or less is preferable, and among them an integer of 4 or less is more preferable.

Specific examples of the alkyl group having 1 to 12 carbon atoms having a thioxanthonyl group, represented by $R^6$ in the general formula (A), include those represented by, for example, the following general formula ($D_6$).

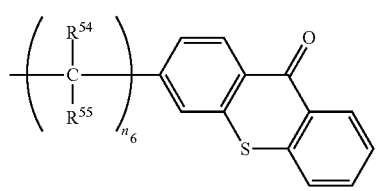

($D_6$)

(wherein $n_6$ pieces of $R^{54}$ and $R^{55}$ each independently represent a hydrogen atom or an alkyl group having 1 to 4 carbon atoms, and $n_6$ represents an integer of 1 to 3, provided that number of carbon atoms of a group constituting $n_6$ pieces of ($R^{54}$—C—$R^{55}$) is 12 or less.)

Specific examples of the alkyl group having 1 to 4 carbon atoms represented by $R^{54}$ and $R^{55}$ in the general formula ($D_6$), include those similar to specific examples of the alkyl group having 1 to 4 carbon atoms represented by $R^{43}$ and $R^{44}$ in the general formula ($D_1$), and also specific examples of the preferable alkyl group include the same.

As $n_6$ pieces of $R^{54}$ and $R^{55}$ in the general formula ($D_6$), a hydrogen atom is more preferable.

$n_6$ in the general formula ($D_6$) is an integer similar to $n_1$ in the general formula ($D_1$), and preferable $n_6$ and more preferable $n_6$ are also integers similar to $n_1$.

Number of carbon atoms of a group constituting $n_6$ pieces of ($R^{54}$—C—$R^{55}$) in the general formula ($D_6$) is usually an integer of 12 or less, among them, an integer of 6 or less is preferable, and among them an integer of 4 or less is more preferable.

An alkenyl group having 2 to 12 carbon atoms represented by $R^6$ in the general formula (A) may be any of a straight chained, branched, or cyclic group, and specifically includes, for example, a vinyl group, a 1-propenyl group, a 2-propenyl group (an allyl group), an isopropenyl group, a n-butenyl group, a n-pentenyl group, a cyclopentenyl group, a n-hexenyl group, a cyclohexenyl group, a n-heptenyl group, a n-octenyl group, a n-nonenyl group, a n-decenyl group, etc., among them, a straight chained, branched alkenyl group having 2 to 6 carbon atoms, such as, for example, a vinyl group, a 1-propenyl group, a 2-propenyl group (an allyl group), an isopropenyl group, a n-butenyl group, a n-pentenyl group, a cyclopentenyl group, a n-hexenyl group, a cyclohexenyl group, is preferable, and among them, a straight chained, branched alkenyl group having carbon atoms of 2 to 3, such as, for example, a vinyl group, a 1-propenyl group, a 2-propenyl group (an allyl group), is more preferable.

An alkynyl group having 2 to 12 carbon atoms represented by $R^6$ in the general formula (A) may be any of a straight chained, branched group, and specifically includes, for example, an ethynyl group, a 1-propynyl group, a 2-propynyl group (a propargyl group), a n-butynyl group, a 1-methylpropargyl group, a n-pentynyl group, a n-hexynyl group, a n-heptynyl group, a n-octynyl group, a n-nonynyl group, a n-decynyl group, among them, a straight chained, branched alkynyl group having 2 to 6 carbon atoms, such as, for example, an ethynyl group, a 1-propynyl group, a 2-propynyl group (a propargyl group), a n-butynyl group, a 1-methylpropargyl group, a n-pentynyl group, a n-hexynyl group, are preferable, and among them, a straight chained, branched alkynyl group having carbon atoms of 2 to 3, such as, for example, an ethynyl group, a 1-propynyl group, a 2-propynyl group (a propargyl group), are more preferable.

An alkyl group having 1 to 12 carbon atoms, in an alkyl group having 1 to 12 carbon atoms which may have an amino group represented by $R^7$ in the general formula (A), includes those similar to specific examples of an alkyl group having 1 to 12 carbon atoms represented by $R^1$ to $R^5$ and $R^8$ to $R^{42}$ in the general formulae (A), ($B_1$), ($B_2$), ($B_3$) and ($B_4$), and specific examples of a preferable alkyl group, the more preferable alkyl group and the further preferable alkyl group include the similar alkyl group to $R^5$ in the general formula (A).

An amino group in an alkyl group having 1 to 12 carbon atoms which may have an amino group, represented by $R^7$ in the general formula (A), may be an unsubstituted amino group, or an amino group substituted with an alkyl group having 1 to 4 carbon atoms. Specific examples of the amino group include, for example, an (unsubstituted) amino group (—NH$_2$ group), an amino group substituted with an alkyl group having 1 to 4 carbon atoms, such as, for example, a methylamino group, a dimethylamino group, an ethylamino group, a diethylamino group, a n-propylamino group, a di-n-propylamino group, an isopropylamino group, a diisopropylamino group, a n-butylamino group, a di-n-butylamino group, an isobutylamino group, a diisobutylamino group, a sec-butylamino group, a di-sec-butylamino group, a tert-butylamino group, a di-tert-butylamino group, a cyclobutylamino group, a dicyclobutylamino group, among them, an amino group substituted with an alkyl group having 1 to 4 carbon atoms is preferable, and among them, a dimethylamino group in which an amino group is substituted with an alkyl group having one carbon atom is more preferable.

Specific examples of the alkyl group having 1 to 12 carbon atoms having an amino group, represented by R$^7$ in the general formula (A), include those represented by, for example, the following general formula (D$_7$).

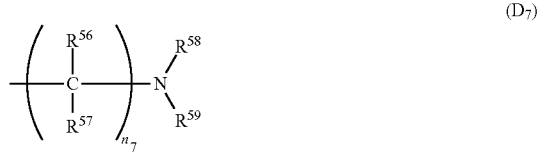

(D$_7$)

(wherein n$_7$ pieces of R$^{56}$ and R$^{57}$ each independently represent a hydrogen atom or an alkyl group having 1 to 4 carbon atoms, R$^{58}$ and R$^{59}$ each independently represent a hydrogen atom or an alkyl group having 1 to 4 carbon atoms, and n$_7$ represents an integer of 1 to 8, provided that number of carbon atoms of a group constituting n$_7$ pieces of (R$^{56}$—C—R$^{57}$) is 12 or less.)

An alkyl group having 1 to 4 carbon atoms represented by R$^{56}$ to R$^{59}$ in the general formula (D$_7$) may be any of a straight chained, branched, or cyclic group, and specifically includes, for example, a methyl group, an ethyl group, a n-propyl group, an isopropyl group, a n-butyl group, an isobutyl group, a sec-butyl group, a tert-butyl group, a cyclobutyl group, and among them, a methyl group, which is an alkyl group having one carbon atom, is preferable.

As n$_7$ pieces of R$^{56}$ and R$^{57}$ in the general formula (D$_7$), a hydrogen atom is more preferable.

As R$^{58}$ and R$^{59}$ in the general formula (D$_7$), an alkyl group having 1 to 4 carbon atoms is more preferable.

n$_7$ in the general formula (D$_7$) represents usually an integer of 1 to 8, among them, an integer of 2 to 8 is preferable, and among them, an integer of 2 to 6 is more preferable, and an integer of 2 to 3 is particularly preferable.

Number of carbon atoms of a group constituting n$_7$ pieces of (R$^{56}$—C—R$^{57}$) in the general formula (D$_7$) is usually an integer of 12 or less, among them, an integer of 8 or less is preferable, and among them an integer of 6 or less is more preferable, and an integer of 3 or less is particularly preferable.

An alkoxy group having 1 to 12 carbon atoms, represented by R$^8$ to R$^{42}$ in the general formulae (B$_1$), (B$_2$), (B$_3$) and (B$_4$), may be any of a straight chained, branched, or cyclic group, and specifically includes, for example, a methoxy group, an ethoxy group, a n-propoxy group, an isopropoxy group, a n-butoxy group, an isobutoxy group, a sec-butoxy group, a tert-butoxy group, a cyclobutoxy group, a n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, a n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, a cyclohexyloxy group, a n-heptyloxy group, an isoheptyloxy group, a sec-heptyloxy group, a tert-heptyloxy group, a neoheptyloxy group, a cycloheptyloxy group, a n-octyloxy group, an isooctyloxy group, a sec-octyloxy group, a tert-octyloxy group, a neooctyloxy group, a 2-ethylhexyloxy group, a cyclooctyloxy group, a n-nonyloxy group, an isononyloxy group, a sec-nonyloxy group, a tert-nonyloxy group, a neononyloxy group, an cyclononyloxy group, a n-decyloxy group, an isodecyloxy group, a sec-decyloxy group, a tert-decyloxy group, a neodecyloxy group, a cyclodecyloxy group, a n-undecyloxy group, a cycloundecyloxy group, a n-dodecyloxy group, a cyclododecyloxy group, a norbornyloxy group (a norbornane-χ-yloxy group), a bornyloxy group (a bornane-χ-yloxy group), a menthyloxy group (a mentha-χ-yloxy group), an adamantyloxy group, a decahydronaphthyloxy group, etc., among them, a straight chained, branched or cyclic alkoxy group having 1 to 4 carbon atoms, such as, for example, a methoxy group, an ethoxy group, a n-propoxy group, an isopropoxy group, a n-butoxy group, an isobutoxy group, a sec-butoxy group, a tert-butoxy group, a cyclobutoxy group, is preferable, and among them, a methoxy group, which is an alkoxy group having one carbon atom, is more preferable.

A halogen atom represented by R$^8$ to R$^{42}$ in the general formulae (B$_1$), (B$_2$), (B$_3$) and (B$_4$) specifically includes, for example, a fluorine atom, a chlorine atom, a bromine atom, an iodine atom, etc., and among them, a chlorine atom and a bromine atom are preferable.

In the general formulae (B$_3$) and (B$_4$), in the case that 2 pieces of R may form a ring structure by binding to each other, 2 pieces of R indicate the case of R$^{26}$ and R$^{27}$, R$^{27}$ and R$^{28}$, R$^{28}$ and R$^{29}$, R$^{30}$ and R$^{31}$, R$^{32}$ and R$^{33}$, R$^{34}$ and R$^{35}$, R$^{37}$ and R$^{38}$, R$^{38}$ and R$^{39}$, and R$^{39}$ and R$^{40}$. That is, it means that these 2 pieces of form a ring structure by binding to each other via a saturated or unsaturated alkylene chain. Such a ring structure may be an alicyclic or aromatic ring, and specifically includes an aliphatic ring having 5 to 8 carbon atoms, such as, for example, a cyclopentane ring, a cyclohexane ring, a cycloheptane ring, a cyclooctane ring, and an aromatic ring having 6 to 10 carbon atoms, such as, for example, a benzene ring, a naphthalene ring.

As R$^1$ to R$^4$ in the general formula (A), an alkyl group having 1 to 12 carbon atoms is preferable.

As R$^5$ in the general formula (A), an alkyl group having 1 to 12 carbon atoms; and an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group, are preferable.

As R$^6$ in the general formula (A), a hydrogen atom; an alkyl group having 1 to 12 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group; an alkenyl group having 2 to 12 carbon atoms; an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group, are more preferable.

As "an alkyl group having 1 to 12 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group" in $R^6$ in the general formula (A), an alkyl group having 1 to 12 carbon atoms, which has no substituent, is more preferable.

As $R^7$ in the general formula (A), an alkyl group having 1 to 12 carbon atoms which may have an amino group; and an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group, are more preferable.

As $Z^-$ in the general formula (A), an anion derived from a carboxylic acid represented by the general formula ($B_1$), ($B_2$) or ($B_3$) is more preferable, and among them, an anion derived from a carboxylic acid represented by the general formula ($B_1$) or ($B_2$) is further preferable, and an anion derived from a carboxylic acid represented by the general formula ($B_1$) is particularly preferable.

As $R^8$ to $R^{15}$ in the general formula ($B_1$), a hydrogen atom and an alkyl group having 1 to 12 carbon atoms are more preferable, and among them, a hydrogen atom is further preferable.

As $R^{16}$ in the general formula ($B_1$), a hydrogen atom and an alkyl group having 1 to 12 carbon atoms are more preferable, and among them, an alkyl group having 1 to 12 carbon atoms is further preferable.

As $R^{17}$ to $R^{24}$ in the general formula ($B_2$), a hydrogen atom and an alkyl group having 1 to 12 carbon atoms are more preferable, and among them, a hydrogen atom is further preferable.

As $R^{25}$ in the general formula ($B_2$), a hydrogen atom and an alkyl group having 1 to 12 carbon atoms are more preferable, and among them, an alkyl group having 1 to 12 carbon atoms is further preferable.

As Y in the general formula ($B_2$), an oxygen atom is preferable.

As $R^{26}$, $R^{27}$, $R^{29}$ to $R^{34}$ and $R^{36}$ in the general formula ($B_3$), a hydrogen atom and an alkyl group having 1 to 12 carbon atoms are more preferable, and among them, a hydrogen atom is further preferable.

As $R^{28}$ in the general formula ($B_3$), a hydrogen atom and an alkoxy group having 1 to 12 carbon atoms are more preferable, and among them, an alkoxy group having 1 to 12 carbon atoms is further preferable.

As $R^{35}$ in the general formula ($B_3$), a hydrogen atom and an alkyl group having 1 to 12 carbon atoms are more preferable, and among them, an alkyl group having 1 to 12 carbon atoms is further preferable.

As $R^{37}$ to $R^{42}$ in the general formula ($B_4$), a hydrogen atom and an alkyl group having 1 to 12 carbon atoms are more preferable, and among them, a hydrogen atom is further preferable.

More preferable specific examples of the compounds represented by the above-described general formula (A) of the present invention include the compounds represented by the following general formulae (A') and (A"). The compounds represented by the general formulae (A') and (A") are those preferable in view of being producible easily and in lower cost, in a shorter step, and providing the base generator having higher solubility to an organic solvent and a base-reactive compound, among the compounds represented by the general formula (A) of the present invention.

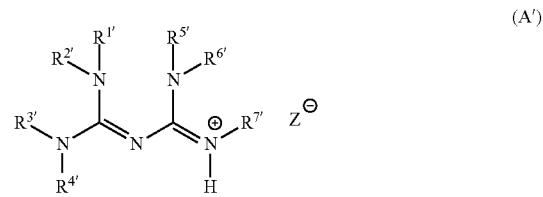

(A')

(wherein $R^{1'}$ to $R^{5'}$ each independently represent an alkyl group having 1 to 8 carbon atoms, $R^{6'}$ represents a hydrogen atom; an alkyl group having 1 to 6 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group; an alkenyl group having 2 to 6 carbon atoms; or an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group, $R^{7'}$ represents an alkyl group having 1 to 8 carbon atoms which may have an amino group, and $Z^-$ is the same as described above.)

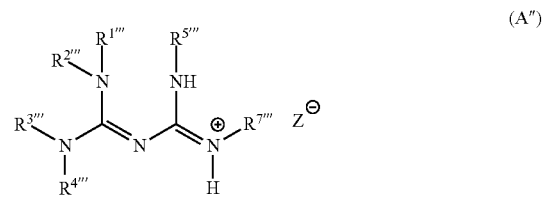

(A")

(wherein $R^{1'''}$ to $R^{4'''}$ each independently represent an alkyl group having 1 to 8 carbon atoms, $R^{5'''}$ represents an alkyl group having 1 to 10 carbon atoms; or an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group, $R^{7'''}$ represents an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group, and $Z^-$ is the same as described above.)

An alkyl group having 1 to 8 carbon atoms represented by $R^{1'}$ to $R^{5'}$ in the general formula (A') may be any of a straight chained, branched, or cyclic group, and specifically includes, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a norbornyl group (a norbornane-χ-yl group), etc., among them, in $R^{1'}$ to $R^{4'}$, a straight chained, branched, or cyclic alkyl group having 1 to 4 carbon atoms, such as, for example, a methyl group, an ethyl group, a n-propyl group, an isopropyl group, a n-butyl group, an isobutyl group, a sec-butyl group, a tert-butyl group, a cyclobutyl group, is preferable, and among them, a methyl group, which is an alkyl group having one carbon atom, is more preferable, and in $R^{5'}$, a straight chained, branched, or cyclic alkyl group having 2 to 8 carbon atoms, such as, for example, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a norbornyl group (a norbornane-χ-yl group), is preferable, and among them, a straight chained, branched, or cyclic alkyl group having 2 to 6 carbon atoms, for example, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, are more preferable.

An alkyl group having 1 to 6 carbon atoms in "an alkyl group having 1 to 6 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group" represented by $R^{6'}$ in the general formula (A') may be any of a straight chained, branched, or cyclic group, and specifically includes, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, and among them, a straight chained, branched, or cyclic alkyl group having 1 to 4 carbon atoms, such as, for example, a methyl group, an ethyl group, a n-propyl group, an isopropyl group, a n-butyl group, an isobutyl group, a sec-butyl group, a tert-butyl group, a cyclobutyl group, is preferable. It should be noted that number of the carbon atoms of the alkyl group shown here means number of the carbon atoms constituting the alkyl group, and number of the carbon atoms constituting a substituent is not contained in number of the carbon atoms represented by "1 to 6 carbon atoms".

An alkoxycarbonyl group having 2 to 6 carbon atoms in "an alkoxycarbonyl group having 2 to 6 carbon atoms in an alkyl group having 1 to 6 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group" represented by $R^{6'}$ in the general formula (A') may be any of a straight chained, branched, or cyclic group, and specifically includes, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a cyclobutoxycarbonyl group, a n-pentyloxycarbonyl group, an isopentyloxycarbonyl group, a sec-pentyloxycarbonyl group, a tert-pentyloxycarbonyl group, a neopentyloxycarbonyl group, a 2-methylbutoxycarbonyl group, a 1,2-dimethylpropoxycarbonyl group, a 1-ethylpropoxycarbonyl group, a cyclopentyloxycarbonyl group, and among them, an alkoxycarbonyl group having 2 to 5 carbon atoms, such as, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a cyclobutoxycarbonyl group, is preferable.

Specific examples of the alkyl group having 1 to 6 carbon atoms having an epoxy group, represented by $R^{6'}$ in the general formula (A'), include those represented by, for example, the following general formula ($D_1'$).

($D_1'$)

(wherein $n_1'$ pieces of $R^{43'}$ and $R^{44'}$ each independently represent a hydrogen atom or a methyl group, and $n_1'$ represents an integer of 1 to 3, provided that number of carbon atoms of a group constituting $n_1'$ pieces of ($R^{43'}$—C—$R^{44'}$) is 6 or less.)

As $n_1'$ pieces of $R^{43'}$ and $R^{44'}$ in the general formula ($D_1'$), a hydrogen atom is more preferable.

$n_1'$ in the general formula ($D_1'$) represents usually an integer of 1 to 3, among them, an integer of 1 to 2 is preferable and 1 is more preferable.

Number of carbon atoms of a group constituting $n_1'$ pieces of ($R^{43'}$—C—$R^{44'}$) in the general formula ($D_1'$) is usually an integer of 6 or less, among them, an integer of 4 or less is preferable, and among them 1 is more preferable.

Specific examples of the alkyl group having 1 to 6 carbon atoms having an alkoxycarbonyl group having 2 to 6 carbon atoms, represented by $R^{6'}$ in the general formula (A'), include those represented by, for example, the following general formula ($D_2'$).

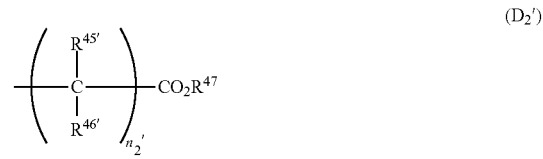

($D_2'$)

(wherein $n_2'$ pieces of $R^{45'}$ and $R^{46'}$ each independently represent a hydrogen atom or a methyl group, $R^{47'}$ represents an alkyl group having 1 to 5 carbon atoms, and $n_2'$ represents an integer of 1 to 3, provided that number of carbon atoms of a group constituting $n_2'$ pieces of ($R^{45'}$—C—$R^{46'}$) are 6 or less.)

An alkyl group having 1 to 5 carbon atoms represents by $R^{47'}$ in the general formula ($D_2'$) may be a straight chained, branched, or cyclic group, and specifically includes, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, 2-methylbutyl group, a 1,2-dimethylpropyl group, a 1-ethylpropyl group, a cyclopentyl group, etc., and among them, an alkyl group having 1 to 4 carbon atoms, such as, for example, a methyl group, an ethyl group, a n-propyl group, an isopropyl group, a n-butyl group, an isobutyl group, a sec-butyl group, a tert-butyl group, a cyclobutyl group, is preferable.

$n_2'$ in the general formula ($D_2'$) is an integer similar to $n_1'$ in the general formula ($D_1'$), and preferable $n_2'$ and more preferable $n_2'$ are also integers similar to $n_1'$.

Number of carbon atoms of a group constituting $n_2'$ pieces of ($R^{45'}$—C—$R^{46'}$) in the general formula ($D_2'$) is usually an integer of 6 or less, and among them, and an integer of 4 or less is preferable.

Specific examples of the alkyl group having 1 to 6 carbon atoms having a coumarinylcarbonyl group, represented by $R^{6'}$ in the general formula (A'), include those represented by, for example, the following general formula ($D_3'$).

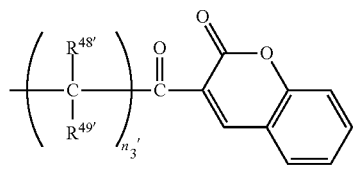

(D$_3'$)

(wherein $n_3'$ pieces of $R^{48'}$ and $R^{49'}$ each independently represent a hydrogen atom or a methyl group, and $n_3'$ represents an integer of 1 to 3, provided that number of carbon atoms of a group constituting $n_3'$ pieces of ($R^{48'}$—C—$R^{49'}$) are 6 or less.)

As $n_3'$ pieces of $R^{48'}$ and $R^{49'}$ in the general formula ($D_3'$), a hydrogen atom is more preferable.

$n_3'$ in the general formula ($D_3'$) is an integer similar to $n_1'$ in the general formula ($D_1'$), and preferable $n_3'$ and more preferable $n_3'$ are also integers similar to $n_1'$.

Number of carbon atoms of a group constituting $n_3'$ pieces of ($R^{48'}$—C—$R^{49'}$) in the general formula ($D_3'$) is usually an integer of 6 or less, among them, an integer of 4 or less is preferable, and among them, 1 is particularly preferable.

Specific examples of the alkyl group having 1 to 6 carbon atoms having an anthraquinonyl group, represented by $R^{6'}$ in the general formula (A'), include those represented by, for example, the following general formula ($D_4'$).

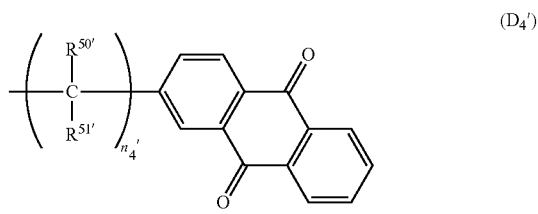

(D$_4'$)

(wherein $n_4'$ pieces of $R^{50'}$ and $R^{51'}$ each independently represent a hydrogen atom or a methyl group, and $n_4'$ represents an integer of 1 to 3, provided that number of carbon atoms of a group constituting $n_4'$ pieces of ($R^{50'}$—C—$R^{51'}$) are 6 or less.)

As $n_4'$ pieces of $R^{50'}$ and $R^{51'}$ in the general formula ($D_4'$), a hydrogen atom is more preferable.

$n_4'$ in the general formula ($D_4'$) is an integer similar to $n_1'$ in the general formula ($D_1'$), and preferable $n_4'$ and more preferable $n_4'$ are also integers similar to $n_1'$.

Number of carbon atoms of a group constituting $n_4'$ pieces of ($R^{50'}$—C—$R^{51'}$) in the general formula ($D_4'$) are usually an integer of 6 or less, and among them, an integer of 4 or less is preferable.

Specific examples of the alkyl group having 1 to 6 carbon atoms having a xanthonyl group, represented by $R^{6'}$ in the general formula (A'), includes those represented by, for example, the following general formula ($D_5'$).

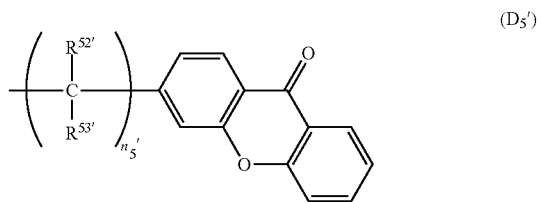

(D$_5'$)

(wherein $n_5'$ pieces of $R^{52'}$ and $R^{53'}$ each independently represent a hydrogen atom or a methyl group, and $n_5'$ represents an integer of 1 to 3, provided that number of carbon atoms of a group constituting $n_5'$ pieces of ($R^{52'}$—C—$R^{53'}$) are 6 or less.)

As $n_5'$ pieces of $R^{52'}$ and $R^{53'}$ in the general formula ($D_5'$), a hydrogen atom is more preferable.

$n_5'$ in the general formula ($D_5'$) is an integer similar to $n_1'$ in the general formula ($D_1'$), and preferable $n_5'$ and more preferable $n_5'$ are also integers similar to $n_1'$.

Number of carbon atoms of a group constituting $n_5'$ pieces of ($R^{52'}$—C—$R^{53'}$) in the general formula ($D_5'$) are usually an integer of 6 or less, and among them, an integer of 4 or less is preferable.

Specific examples of the alkyl group having 1 to 6 carbon atoms having a thioxanthonyl group, represented by $R^{6'}$ in the general formula (A'), include those represented by, for example, the following general formula ($D_6'$).

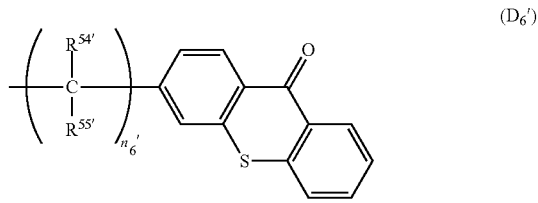

(D$_6'$)

(wherein $n_6'$ pieces of $R^{54'}$ and $R^{55'}$ each independently represent a hydrogen atom or a methyl group, and $n_6'$ represents an integer of 1 to 3, provided that number of carbon atoms of a group constituting $n_6'$ pieces of ($R^{54'}$—C—$R^{55'}$) are 6 or less.)

As $n_6'$ pieces of $R^{54'}$ and $R^{55'}$ in the general formula ($D_6'$), a hydrogen atom is more preferable.

$n_6'$ in the general formula ($D_6'$) is an integer similar to $n_1'$ in the general formula ($D_1'$), and preferable $n_6'$ and more preferable $n_6'$ are also integers similar to $n_1'$.

Number of carbon atoms of a group constituting $n_6'$ pieces of ($R^{54'}$—C—$R^{55'}$) in the general formula ($D_6'$) is usually an integer of 6 or less, and among them, an integer of 4 or less is preferable.

An alkenyl group having 2 to 6 carbon atoms represented by $R^{6'}$ in the general formula (A') may be any of a straight chained, branched, or cyclic group, and specifically includes, for example, an vinyl group, a 1-propenyl group, a 2-propenyl group (an allyl group), an isopropenyl group, a n-butenyl group, a n-pentenyl group, a cyclopentenyl group, a n-hexenyl group, a cyclohexenyl group, etc., and among them, a straight chained, branched alkenyl group having carbon atoms of 2 to 3, such as, for example, a vinyl group, a 1-propenyl group, a 2-propenyl group (an allyl group), is preferable.

An arylalkyl group having 7 to 15 carbon atoms, in "an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group" represented by $R^{6'}$ in the general formula (A'), may be any of a monocyclic, or condensed polycyclic group, and specifically includes, for example, a benzyl group, a phenethyl group, a methylbenzyl group, a phenylpropyl group, a 1-methylphenylethyl group, a phenylbutyl group, a 2-methylphenylpropyl group, a tetrahydronaphthyl group, a naphthylmethyl group, a naphthylethyl group, an indenyl group, a fluorenyl group, an anthracenylmethyl group (an anthrylmethyl group), a phenanthrenylmethyl group (a phenanthrylmethyl group), etc., and among them, a benzyl group, and an anthracenylmethyl group (an anthrylmethyl group) are preferable. It should be noted that number of the carbon atoms of the arylalkyl group shown here means number of the carbon atoms constituting the arylalkyl group, and number of the carbon atoms constituting a substituent is not contained in number of the carbon atoms represented by the "7 to 15 carbon atoms".

An alkyl group having 1 to 6 carbon atoms, in "an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group" represented by $R^{6'}$ in the general formula (A'), means an alkyl group having 1 to 6 carbon atoms binding to carbon atoms on an aryl group, and specific examples thereof include, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, etc., and among them, an alkyl group having 1 to 4 carbon atoms, such as, for example, a methyl group, an ethyl group, a n-propyl group, an isopropyl group, a n-butyl group, an isobutyl group, a sec-butyl group, a tert-butyl group, a cyclobutyl group, is preferable.

An alkoxy group having 1 to 6 carbon atoms, in "an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group" represented by $R^{6'}$ in the general formula (A'), means an alkoxy group having 1 to 6 carbon atoms binding to carbon atom on an aryl group, and specific examples thereof includes, for example, a methoxy group, an ethoxy group, a n-propoxy group, an isopropoxy group, a n-butoxy group, an isobutoxy group, a sec-butoxy group, a tert-butoxy group, a cyclobutoxy group, a n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, a n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, a cyclohexyloxy group, etc., and among them, an alkoxy group having 1 to 4 carbon atoms, such as, for example, a methoxy group, an ethoxy group, a n-propoxy group, an isopropoxy group, a n-butoxy group, an isobutoxy group, a sec-butoxy group, a tert-butoxy group, a cyclobutoxy group, is preferable.

A halogen atom, in "an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group" represented by $R^{6'}$ in the general formula (A'), means a halogen atom binding to carbon atoms on an aryl group, and specific examples thereof include, such as, for example, a fluorine atom, a chlorine atom, a bromine atom, an iodine atom, and among them, a chlorine atom and a bromine atom are preferable.

A nitro group, in "an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group" represented by $R^{6'}$ in the general formula (A'), means a nitro group binding to carbon atoms on an aryl group.

Among the substituents, in "an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group" represented by $R^{6'}$ in the general formula (A'), an alkyl group having 1 to 6 carbon atoms, and an alkoxy group having 1 to 6 carbon atoms are preferable.

An alkyl group having 1 to 8 carbon atoms, in an alkyl group having 1 to 8 carbon atoms which may have an amino group represented by $R^{7'}$ in the general formula (A'), may be any of a straight chained, branched, or cyclic group, and specifically includes, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a norbornyl group (a norbornane-χ-yl group), etc., among them, an alkyl group having 2 to 8 carbon atoms, such as, for example, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a norbornyl group (a norbornane-χ-yl group), is preferable, and among them, a straight chained, branched, or cyclic alkyl group having 2 to 6 carbon atoms, such as, for example, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, is more preferable.

An amino group, in an alkyl group having 1 to 8 carbon atoms which may have an amino group, represented by $R^{7'}$ in the general formula (A'), may be an unsubstituted amino group, or an amino group substituted with an alkyl group having 1 to 4 carbon atoms. Specific examples of the amino group include, for example, an (unsubstituted) amino group ($-NH_2$ group), an amino group substituted with an alkyl group having 1 to 4 carbon atoms, such as, for example, a methylamino group, a dimethylamino group, an ethylamino group, a diethylamino group, a n-propylamino group, a di-n-propylamino group, an isopropylamino group, a diisopropylamino group, a n-butylamino group, a di-n-butylamino group, an isobutylamino group, a diisobutylamino group, a sec-butylamino group, a di-sec-butylamino group, a tert-butylamino group, a di-tert-butylamino group, a cyclobutylamino group, a dicyclobutylamino group, among them, an amino group substituted with an alkyl group having 1 to 4 carbon atoms is preferable, and among them, a dimethylamino group in which an amino group is substituted with an alkyl group having one carbon atom is more preferable.

Specific examples of the alkyl group having 1 to 8 carbon atoms having an amino group, represented by $R^{7'}$ in the general formula (A'), include those represented by, for example, the following general formula ($D_7'$).

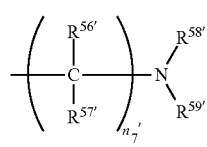
(D$_7'$)

(wherein $n_7'$ pieces of $R^{56'}$ and $R^{57'}$ each independently represent, a hydrogen atom or a methyl group, $R^{58'}$ and $R^{59'}$ each independently represent a hydrogen atom or an alkyl group having 1 to 4 carbon atoms, and $n_7'$ represents an integer of 1 to 8, provided that number of carbon atoms of a group constituting $n_7'$ pieces of ($R^{56'}$—C—$R^{57'}$) are 8 or less.)

As $n_7'$ pieces of $R^{56'}$ and $R^{57'}$ in the general formula (D$_7'$), a hydrogen atom is more preferable.

As $R^{58'}$ and $R^{59'}$ in the general formula (D$_7'$), an alkyl group having 1 to 4 carbon atoms is more preferable.

$n_7'$ in the general formula (D$_7'$) represents usually an integer of 1 to 8, among them, an integer of 2 to 8 is preferable, and among them, an integer of 2 to 6 is preferable, and among them, an integer of 2 to 3 is particularly preferable, and 3 is most preferable.

Number of carbon atoms of a group constituting $n_7'$ pieces of ($R^{56'}$—C—$R^{57'}$) in the general formula (D$_7'$) is usually an integer of 8 or less, among them, an integer of 6 or less is preferable, and among them an integer of 3 or less is more preferable, and 3 is most preferable.

More preferable specific examples of the anion derived from a carboxylic acid, represented by $Z^-$ in the general formula (A') include the anion represented by the following general formulae (B$_1'$), (B$_2'$), (B$_3'$) and (B$_4'$).

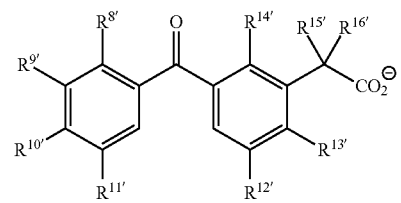
(B$_1'$)

(wherein $R^{8'}$ to $R^{16'}$ each independently represent a hydrogen atom or an alkyl group having 1 to 4 carbon atoms.)

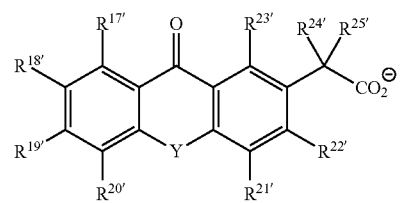
(B$_2'$)

(wherein $R^{17'}$ to $R^{25'}$ each independently represent a hydrogen atom or an alkyl group having 1 to 4 carbon atoms, and Y represents an oxygen atom or a sulfur atom.)

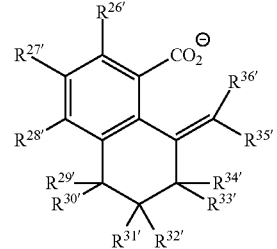
(B$_3'$)

(wherein $R^{26'}$, $R^{27'}$, and $R^{29'}$ to $R^{36'}$ each independently represent a hydrogen atom or an alkyl group having 1 to 4 carbon atoms, and $R^{28'}$ represents a hydrogen atom or an alkoxy group having 1 to 4 carbon atoms.)

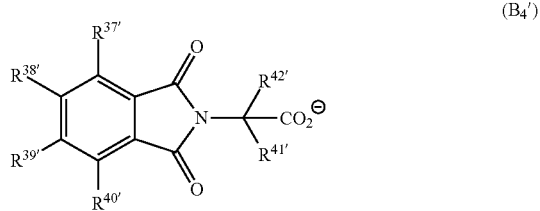

(B₄')

(wherein $R^{37'}$ to $R^{42'}$ each independently represent a hydrogen atom or an alkyl group having 1 to 4 carbon atoms.)

An alkyl group having 1 to 4 carbon atoms represented by $R^{8'}$ to $R^{27'}$ and $R^{29'}$ to $R^{42'}$ in the general formulae ($B_1'$), ($B_2'$), ($B_3'$) and ($B_4'$) may be any of a straight chained, branched, and cyclic group, and specifically includes, for example, a methyl group, an ethyl group, a n-propyl group, an isopropyl group, a n-butyl group, an isobutyl group, a sec-butyl group, a tert-butyl group, a cyclobutyl group, etc., and among them, a methyl group, which is an alkyl group having one carbon atom, is preferable.

An alkoxy group having 1 to 4 carbon atoms represented by $R^{28'}$ in the general formulae ($B_1'$), ($B_2'$), ($B_3'$) and ($B_4'$) may be any of a straight chained, branched, and cyclic group, and specifically includes, for example, a methoxy group, an ethoxy group, a n-propoxy group, an isopropoxy group, a n-butoxy group, an isobutoxy group, a sec-butoxy group, a tert-butoxy group, a cyclobutoxy group, etc., and among them, a methoxy group, which is an alkoxy group having one carbon atom, is preferable.

As $Z^-$ in the general formula (A'), an anion derived from a carboxylic acid, represented by the general formula ($B_1'$), ($B_2'$) or ($B_3'$) is more preferable, and among them, an anion derived from a carboxylic acid, represented by the general formula ($B_1'$) or ($B_2'$) is still more preferable, and an anion derived from a carboxylic acid, represented by the general formula ($B_1'$) is particularly preferable.

As "an alkyl group having 1 to 6 carbon atoms which may have a substituent selected from the group consisting of an epoxy group, an alkoxycarbonyl group carbon having number 2 to 6, a coumarinylcarbonyl group, an anthraquinonyl group, a xanthonyl group and a thioxanthonyl group" represented by $R^{6'}$ in the general formula (A'), an alkyl group having 1 to 6 carbon atoms, which has no substituent, is more preferable.

As $R^{8'}$ to $R^{15'}$ in the general formula ($B_1'$), a hydrogen atom is more preferable.

As $R^{16'}$ in the general formula ($B_1'$), an alkyl group having 1 to 4 carbon atoms is more preferable.

As $R^{17'}$ to $R^{24'}$ in the general formula ($B_2'$), a hydrogen atom is more preferable.

As $R^{25'}$ in the general formula ($B_2'$), an alkyl group having 1 to 4 carbon atoms is more preferable.

As Y in the general formula ($B_2'$), an oxygen atom is more preferable.

As $R^{26'}$, $R^{27'}$, $R^{29'}$ to $R^{34'}$ and $R^{36'}$ in the general formula ($B_3'$), a hydrogen atom is more preferable.

As $R^{28'}$ in the general formula ($B_3'$), an alkoxy group having 1 to 4 carbon atoms is more preferable.

As $R^{35'}$ in the general formula ($B_3'$), an alkyl group having 1 to 4 carbon atoms is more preferable.

As $R^{37'}$ to $R^{42'}$ in the general formula ($B_4'$), a hydrogen atom is more preferable.

Among the compounds represented by the general formula (A'), the compounds composed of a combination of a biguanidium cation (a biguanide structure) selected from the following formulae (A-1) to (A-16), and a carboxylic acid ion (an anion derived from a carboxylic acid; a carboxylic acid structure) selected from the following formulae ($B_1$-1), ($B_2$-1), ($B_3$-1) and ($B_4$-1) are more preferable.

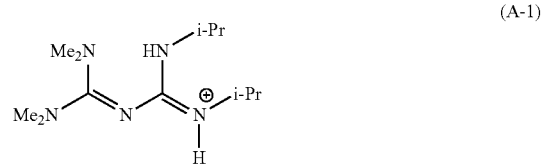

(A-1)

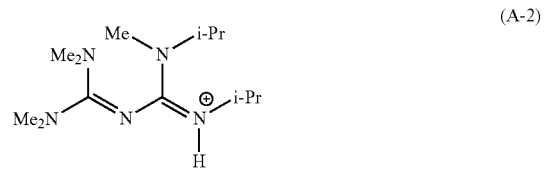

(A-2)

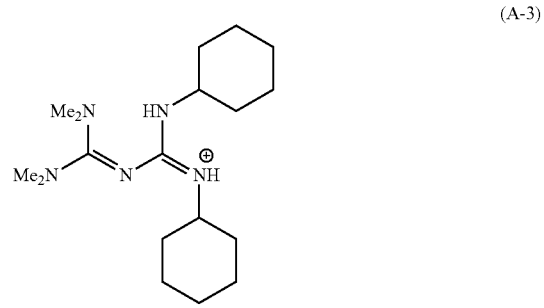

(A-3)

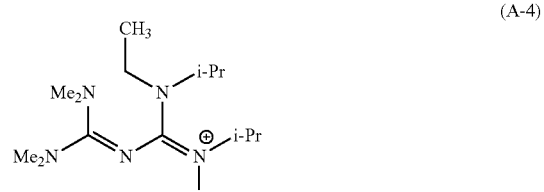

(A-4)

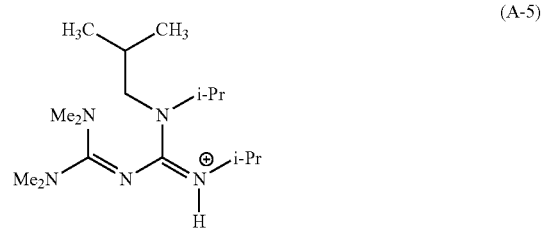

(A-5)

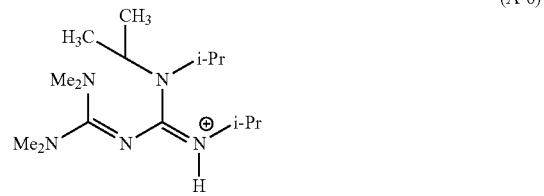

(A-6)

(A-7)
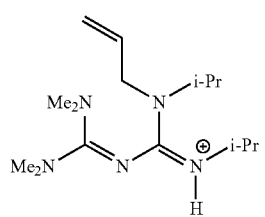
(A-8)
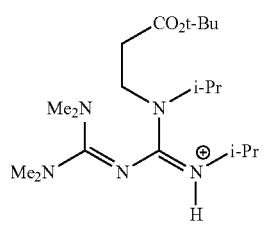
(A-9)
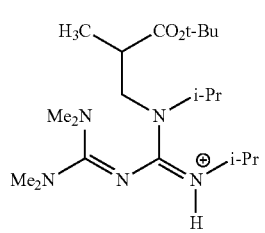
(A-10)
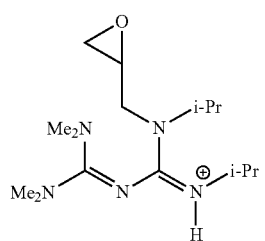
(A-11)
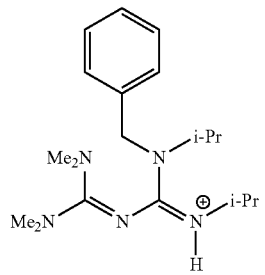
(A-12)
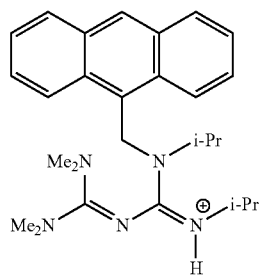
(A-13)
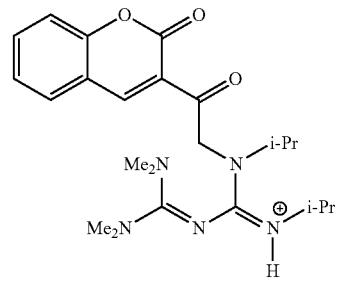
(A-14)
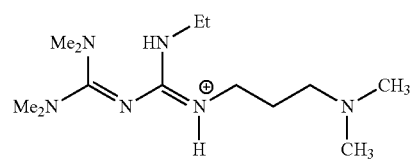
(A-15)
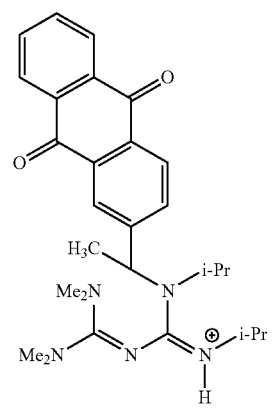
(A-16)
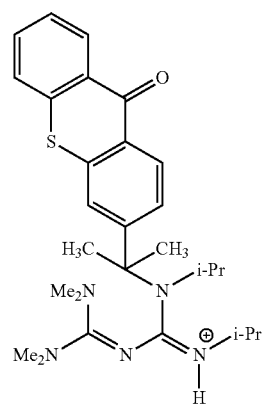
(B₁-1)
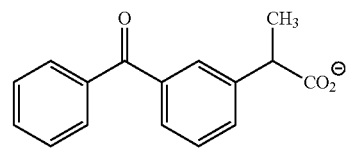
(B₂-1)
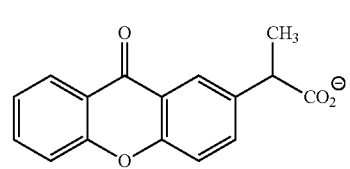

(B₃-1) 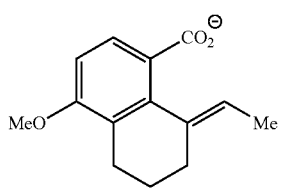
(B₄-1) 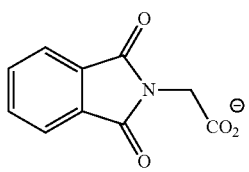
Still more, specific examples of the compounds composed of a combination of the above-described biguanidium cation (a biguanide structure) and the above-described carboxylic acid ion (an anion derived from a carboxylic acid; a carboxylic acid structure) include, for example, the compounds represented by following formulae (1), (2), (3), (4), (5), (6), (7) and (8).
(1) 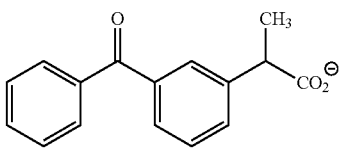
(2) 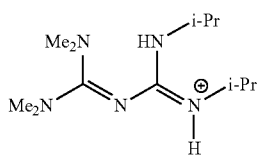
(3) 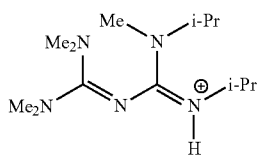
(4) 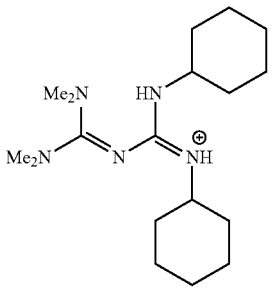
(5) 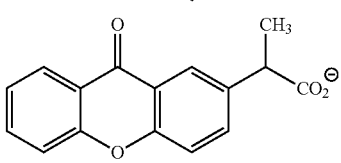
(6) 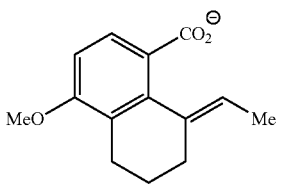
(7) 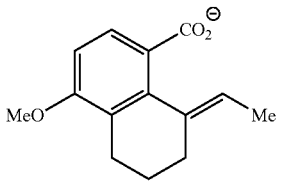

-continued

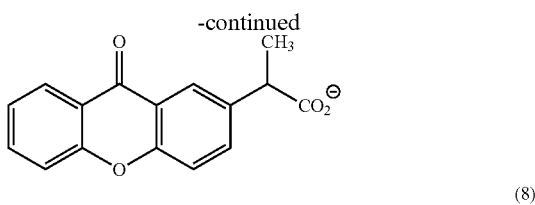

(8)

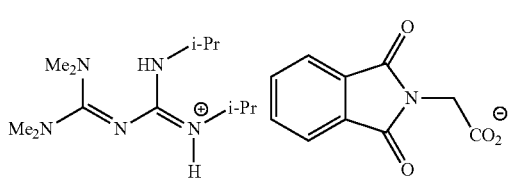

The compound represented by the formula (1) corresponds to a compound, in the compound represented by the general formula (A), where $R^1$ to $R^4$ are a methyl group, which is an alkyl group having one carbon atom, $R^5$ and $R^7$ are an isopropyl group, which is a branched alkyl group having 3 carbon atoms, $R^6$ is a hydrogen atom, $Z^-$ is an anion derived from a carboxylic acid, represented by the general formula ($B_1$), where $R^8$ to $R^{15}$ in the general formula ($B_1$) are a hydrogen atom, and $R^{16}$ is a methyl group, which is an alkyl group having one carbon atom.

The compound represented by the formula (2) corresponds to a compound, in the compound represented by the general formula (A), where $R^1$ to $R^4$ is a methyl group, which is an alkyl group having one carbon atom, $R^5$ and $R^7$ are an isopropyl group, which is a branched alkyl group having 3 carbon atoms, $R^6$ is a methyl group, which is an alkyl group having one carbon atom and not having a substituent, $Z^-$ is an anion derived from a carboxylic acid, represented by the general formula ($B_1$), where $R^8$ to $R^{15}$ in the general formula ($B_1$) are a hydrogen atom, and $R^{16}$ is a methyl group, which is an alkyl group having one carbon atom.

The compound represented by the formula (3) corresponds to a compound, in the compound represented by the general formula (A), where $R^1$ to $R^4$ is a methyl group, which is an alkyl group having one carbon atom, $R^5$ and $R^7$ are an cyclohexyl group, which is a cyclic alkyl group having 6 carbon atoms, $R^6$ is a hydrogen atom, $Z^-$ is an anion derived from a carboxylic acid, represented by the general formula ($B_1$), where $R^8$ to $R^{15}$ in the general formula ($B_1$) are a hydrogen atom, and $R^{16}$ is a methyl group, which is an alkyl group having one carbon atom.

The compound represented by the formula (4) corresponds to a compound, in the compound represented by the general formula (A), where $R^1$ to $R^4$ is a methyl group, which is an alkyl group having one carbon atom, $R^5$ and $R^7$ are an cyclohexyl group, which is a cyclic alkyl group having 6 carbon atoms, $R^6$ is a hydrogen atom, $Z^-$ is an anion derived from a carboxylic acid, represented by the general formula ($B_2$), where $R^{17}$ to $R^{24}$ in the general formula ($B_2$) are a hydrogen atom, $R^{25}$ is a methyl group, which is an alkyl group having one carbon atom, and Y is an oxygen atom.

The compound represented by the formula (5) corresponds to a compound, in the compound represented by the general formula (A), where $R^1$ to $R^4$ is a methyl group, which is an alkyl group having one carbon atom, $R^5$ and $R^7$ are an isopropyl group, which is a branched alkyl group having 3 carbon atoms, $R^6$ is a hydrogen atom, $Z^-$ is an anion derived from a carboxylic acid, represented by the general formula ($B_3$), where $R^{26}$, $R^{27}$, $R^{29}$ to $R^{34}$ and $R^{36}$ in the general formula ($B_3$) are a hydrogen atom, $R^{28}$ is a methoxy group, which is an alkoxy group having one carbon atom, and $R^{35}$ is a methyl group, which is an alkyl group having one carbon atom.

The compound represented by the formula (6) corresponds to a compound, in the compound represented by the general formula (A), where $R^1$ to $R^4$ is a methyl group, which is an alkyl group having one carbon atom, $R^5$ and $R^7$ are an cyclohexyl group, which is a cyclic alkyl group having 6 carbon atoms, $R^6$ is a hydrogen atom, $Z^-$ is an anion derived from a carboxylic acid, represented by the general formula ($B_3$), where $R^{26}$, $R^{27}$, $R^{29}$ to $R^{34}$ and $R^{36}$ in the general formula ($B_3$) are a hydrogen atom, $R^{28}$ is a methoxy group, which is an alkoxy group having one carbon atom, and $R^{35}$ is a methyl group, which is an alkyl group having one carbon atom.

The compound represented by the formula (7) corresponds to a compound, in the compound represented by the general formula (A), where $R^1$ to $R^4$ is a methyl group, which is an alkyl group having one carbon atom, $R^5$ and $R^7$ are an isopropyl group, which is a branched alkyl group having 3 carbon atoms, $R^6$ is a hydrogen atom, $Z^-$ is an anion derived from a carboxylic acid, represented by the general formula ($B_2$), where $R^{17}$ to $R^{24}$ in the general formula ($B_2$) are a hydrogen atom, and $R^{25}$ is a methyl group, which is an alkyl group having one carbon atom, and Y is an oxygen atom.

The compound represented by the formula (8) corresponds to a compound, in the compound represented by the general formula (A), where $R^1$ to $R^4$ is a methyl group, which is an alkyl group having one carbon atom, $R^5$ and $R^7$ are an isopropyl group, which is a branched alkyl group having 3 carbon atoms, $R^6$ is a hydrogen atom, $Z^-$ is an anion derived from a carboxylic acid, represented by the general formula ($B_4$), where $R^{37}$ to $R^{42}$ in the general formula ($B_4$) are a hydrogen atom.

An alkyl group having 1 to 8 carbon atoms represented by $R^{1''''}$ to $R^{4''''}$ in the general formula (A'') may be any of a straight chained, branched, or cyclic group, and specifically includes, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a norbornyl group (a norbornane-χ-yl group), etc., among them, a straight chained, branched, or cyclic alkyl group having 1 to 4 carbon atoms, such as, for example, a methyl group, an ethyl group, a n-propyl group, an isopropyl group, a n-butyl group, an isobutyl group, a sec-butyl group, a tert-butyl group, a cyclobutyl group, is preferable, and among them, a methyl group which is an alkyl group having one carbon atom, is more preferable.

An alkyl group having 1 to 10 carbon atoms represented by $R^{5'''}$ in the general formula (A'') may be any of a straight chained, branched, or cyclic group, and specifically includes, for example, a methyl group, an ethyl group, a n-propyl group, an isopropyl group, a n-butyl group, an isobutyl group, a sec-butyl group, a tert-butyl group, a cyclobutyl group, n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a n-nonyl group, an isononyl group, a sec-nonyl group, a tert-nonyl group, a neononyl group, a cyclononyl group, a n-decyl group, an isodecyl group, a sec-decyl group, a tert-decyl group, a neodecyl group, a cyclodecyl group, a norbornyl group (a norbornane-χ-yl group), a bornyl group (a bornane-χ-yl group), a menthyl group (a mentha-χ-yl group), an adamantyl group, a decahydronaphthyl group, among them, a straight chained, branched, or cyclic alkyl group having 1 to 8 carbon atoms, such as, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a norbornyl group (a norbornane-χ-yl group), is preferable, and among them, a straight chained, branched, or cyclic alkyl group having 2 to 8 carbon atoms, such as, for example, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, a isooctyl group, a sec-octyl group, a tert-octyl group, a neooctyl group, a 2-ethylhexyl group, a cyclooctyl group, a norbornyl group (a norbornane-χ-yl group), etc., is more preferable.

Specific examples of the aryl group having 6 to 14, in "an aryl group having 6 to 14 which may have a substituent selected from the group consisting of an alkyl group having 1 to 6 carbon atoms, an alkoxy group having 1 to 6 carbon atoms, a halogen atom and a nitro group" represented by $R^{5'''}$ and $R^{7'''}$ in the general formula (A''), include those similar to specific examples of an aryl group having 6 to 14 carbon atoms, in "an aryl group having 6 to 14 which may have a substituent selected from the group consisting of an alkyl group having 1 to 6 carbon atoms, an alkoxy group having 1 to 6 carbon atoms, a halogen atom and a nitro group" represented by $R^1$ and $R^7$ in the general formula (A), and also specific examples of the preferable aryl group and the more preferable aryl group include the same.

Specific examples of the alkyl group having 1 to 6, in "an aryl group having 6 to 14 which may have a substituent selected from the group consisting of an alkyl group having 1 to 6 carbon atoms, an alkoxy group having 1 to 6 carbon atoms, a halogen atom and a nitro group" represented by $R^{5'''}$ and $R^{7'''}$ in the general formula (A''), include those similar to specific examples of an alkyl group having 1 to 6 carbon atoms, in "an aryl group having 6 to 14 which may have a substituent selected from the group consisting of an alkyl group having 1 to 6 carbon atoms, an alkoxy group having 1 to 6 carbon atoms, a halogen atom and a nitro group" represented by $R^1$ to $R^7$ in the general formula (A), and also specific examples of the preferable alkyl group include the same.

Specific examples of the alkoxy group having 1 to 6, in "an aryl group having 6 to 14 which may have a substituent selected from the group consisting of an alkyl group having 1 to 6 carbon atoms, an alkoxy group having 1 to 6 carbon atoms, a halogen atom and a nitro group" represented by $R^{5'''}$ and $R^{7'''}$ in the general formula (A''), include those similar to specific examples of an alkoxy group having 1 to 6 carbon atoms, in "an aryl group having 6 to 14 which may have a substituent selected from the group consisting of an alkyl group having 1 to 6 carbon atoms, an alkoxy group having 1 to 6 carbon atoms, a halogen atom and a nitro group" represented by $R^1$ to $R^7$ in the general formula (A), and also specific examples of the preferable alkoxy group include the same.

Specific examples of the halogen atom, in "an aryl group having 6 to 14 which may have a substituent selected from the group consisting of an alkyl group having 1 to 6 carbon atoms, an alkoxy group having 1 to 6 carbon atoms, a halogen atom and a nitro group" represented by $R^{5'''}$ and $R^{7'''}$ in the general formula (A''), include those similar to specific examples of a halogen atom, in "an aryl group having 6 to 14 which may have a substituent selected from the group consisting of an alkyl group having 1 to 6 carbon atoms, an alkoxy group having 1 to 6 carbon atoms, a halogen atom and a nitro group" represented by $R^1$ to $R^7$ in the general formula (A), and also specific examples of the preferable halogen atom include the same.

A nitro group, in "an aryl group having 6 to 14 which may have a substituent selected from the group consisting of an alkyl group having 1 to 6 carbon atoms, an alkoxy group having 1 to 6 carbon atoms, a halogen atom and a nitro group" represented by $R^{5'''}$ and $R^{7'''}$ in the general formula (A''), means a nitro group binding to carbon atoms on an aryl group.

Among the substituents, in "an aryl group having 6 to 14 which may have a substituent selected from the group consisting of an alkyl group having 1 to 6 carbon atoms, an alkoxy group having 1 to 6 carbon atoms, a halogen atom and a nitro group" represented by $R^{5'''}$ and $R^{7'''}$ in the general formula (A''), an alkyl group having 1 to 6 carbon atoms, and an alkoxy group having 1 to 6 carbon atoms are preferable.

Specific examples of "an aryl group having 6 to 14 which may have a substituent selected from the group consisting of an alkyl group having 1 to 6 carbon atoms, an alkoxy group having 1 to 6 carbon atoms, a halogen atom and a nitro group" represented by $R^{5'''}$ and $R^{7'''}$ in the general formula (A'') include an aryl group having 6 to 14 carbon atoms having no substituents, such as, for example, a phenyl group, a naphthyl group; an aryl group having 6 to 14 carbon atoms having an alkyl group having 1 to 4 carbon atoms, such as, for example, a 4-methylphenyl group, a 4-ethylphenyl group, a 4-n-propylphenyl group, a 4-isopropylphenyl group, a 4-n-butylphenyl group, a 4-isobutylphenyl group, a 4-sec-butylphenyl group, a 4-tert-butylphenyl group, a 4-cyclobutylphenyl group, a 2,6-dimethylphenyl group, a 2,6-diethylphenyl group, a 2,6-di-n-propylphenyl group, a 2,6-diisopropylphenyl group, a 2,6-di-n-butylphenyl group, a 2,6-diisobutylphenyl group, a 2,6-di-sec-butylphenyl group, a 2,6-di-tert-butylphenyl group, a 2,6-dicyclobutylphenyl group; and an aryl group having 6 to 14 carbon atoms having an alkoxy group having 1 to 4 carbon atoms, such as, for example, a 3,4-dimethoxyphenyl group, a 3,4-diethoxyphenyl group, a 3,4-di-n-propoxyphenyl group, a 3,4-diisopropoxyphenyl group, a 3,4-di-n-butoxyphenyl group, a 3,4-diisobutoxyphenyl group, a 3,4-di-sec-butoxyphenyl group, a 3,4-di-tert-butoxyphenyl group, a 3,4-dicyclobutoxyphenyl group.

More preferable specific examples of the anion derived from a carboxylic acid, represented by $Z^-$ in the general formula (A") include an anion represented by the above-described general formulae ($B_1'$), ($B_2'$), ($B_3'$) and ($B_4'$).

Among the compounds represented by the general formula (A"), the compounds composed of a combination of a biguanidium cation (a biguanide structure) selected from the following formulae (A-17) to (A-20), and a carboxylic acid ion (an anion derived from a carboxylic acid; a carboxylic acid structure) selected from the following formulae ($B_1$-1), ($B_2$-1), ($B_3$-1) and ($B_4$-1) are more preferable.

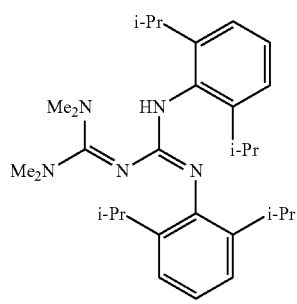

(A-17)

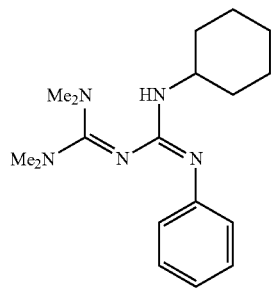

(A-18)

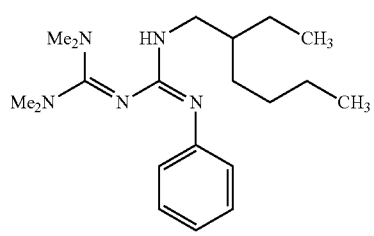

(A-19)

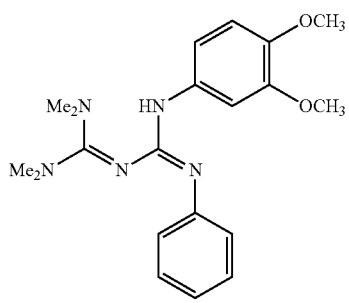

(A-20)

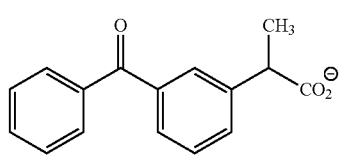

($B_1$-1)

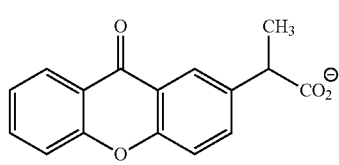

($B_2$-1)

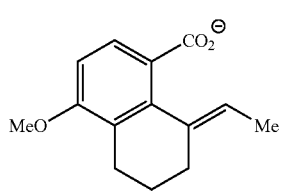

($B_3$-1)

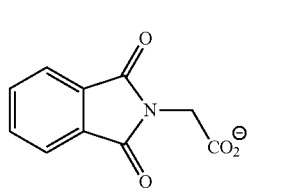

($B_4$-1)

Still more, specific examples of the compounds composed of a combination of the above-described biguanidium cation (a biguanide structure) and the above-described carboxylic acid ion (an anion derived from a carboxylic acid; a carboxylic acid structure) include, for example, the compounds represented by the following formulae (9), (10), (11) and (12).

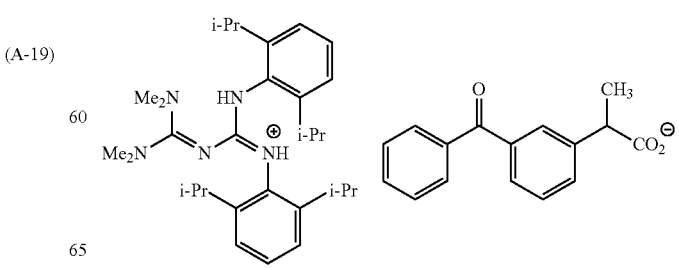

(9)

-continued (10)

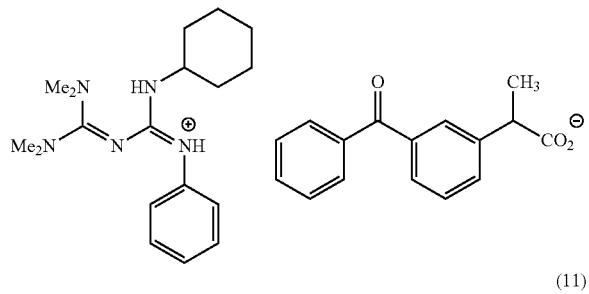

(11)

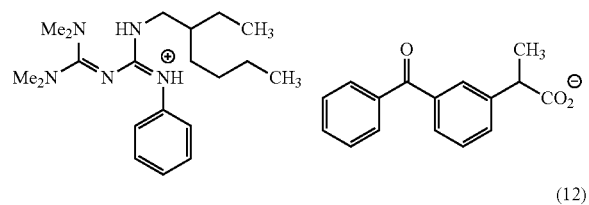

(12)

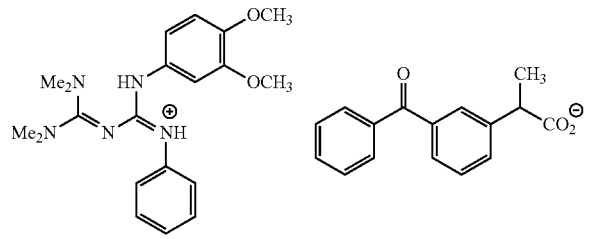

The compound represented by the formula (9) corresponds to a compound, in the compound represented by the general formula (A), where $R^1$ to $R^4$ are a methyl group, which is an alkyl group having one carbon atom, $R^5$ and $R^7$ are a phenyl group, which is an aryl group having 6 carbon atoms which contains 2 pieces of isopropyl groups having 3 carbon atoms of the branched alkyl group as substituents, $R^6$ is a hydrogen atom, $Z^-$ is an anion derived from a carboxylic acid represented by the general formula ($B_1$), where $R^8$ to $R^{15}$ in the general formula ($B_1$) are a hydrogen atom, and $R^{16}$ is a methyl group, which is an alkyl group having one carbon atom.

The compound represented by the formula (10) corresponds to a compound, in the compound represented by the general formula (A), where $R^1$ to $R^4$ are a methyl group, which is an alkyl group having one carbon atom, $R^5$ is a cyclohexyl group, which is an alkyl group having 6 carbon atoms, $R^6$ is a hydrogen atom, $R^7$ is a phenyl group, which is an aryl group having 6 carbon atoms, $Z^-$ is an anion derived from a carboxylic acid represented by the general formula ($B_1$), where $R^8$ to $R^{15}$ in the general formula ($B_1$) are a hydrogen atom, and $R^{16}$ is a methyl group, which is an alkyl group having one carbon atom.

The compound represented by the formula (11) corresponds to a compound, in the compound represented by the general formula (A), where $R^1$ to $R^4$ are a methyl group, which is an alkyl group having one carbon atom, $R^5$ is a 2-ethyl-n-hexyl group, which is a branched alkyl group having 8 carbon atoms, $R^6$ is a hydrogen atom, $R^7$ is a phenyl group, which is an aryl group having 6 carbon atoms, and $Z^-$ is an anion derived from a carboxylic acid represented by the general formula ($B_1$), where $R^8$ to $R^{15}$ in the general formula ($B_1$) are a hydrogen atom, and $R^{16}$ is a methyl group, which is an alkyl group having one carbon atom.

The compound represented by the formula (12) corresponds to a compound, in the compound represented by the general formula (A), where $R^1$ to $R^4$ are a methyl group, which is an alkyl group having one carbon atom, $R^5$ is a phenyl group, which is an aryl group having 6 carbon atoms which contains 2 pieces of methoxy groups having one carbon atom of the alkoxy group as substituents, $R^6$ is a hydrogen atom, $R^7$ is a phenyl group, which is an aryl group having 6 carbon atoms, $Z^-$ is an anion derived from a carboxylic acid represented by the general formula ($B_1$), where $R^8$ to $R^{15}$ in the general formula ($B_1$) are a hydrogen atom, and $R^{16}$ is a methyl group, which is an alkyl group having one carbon atom.

The compound represented by the general formula (A) of the present invention represents the compound where a proton is bound to a terminal imine, and an cation is present at a terminal part, however, the proton also binds to nitrogen atom at 3 position in a biguanide structure in the compound represented by the general formula (A) to be able to form the compound represented by the following general formula (AA). That is, these cause proton tautomerism, and the compound represented by the general formula (A) and the compound represented by the general formula (AA) are in a relationship of tautomerism each other. Accordingly, the compounds represented by the general formula (A) of the present invention are contained the compounds represented by the general formula (AA), or these mixed compounds are also contained in the compounds represented by the general formula (A) of the present invention.

(AA)

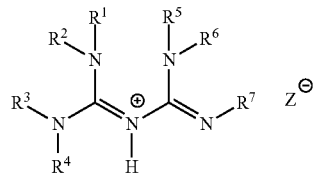

(wherein $R^1$ to $R^7$ and $Z^-$ are the same as described above.)

—A Production Method of the Compound Represented by the General Formula (A) of the Present Invention—

The compound represented by the general formula (A) of the present invention mentioned above can be produced by a method represented by, for example, the following scheme. That is, among the compounds represented by the general formula (A), the compound where $R^6$ in the general formula (A) is a hydrogen atom (a compound represented by the following general formula ($A_1$)), may be synthesized, for example, by reacting a guanidine or a guanidine derivative represented by the general formula (I) with a carbodiimide derivative represented by the general formula (II) to obtain the compound represented by the general formula (III), and subsequently by a reacting the compound represented by the general formula (III) with a carboxylic acid represented by the general formula ($B_1$—H), ($B_2$—H), ($B_3$—H) or ($B_4$—H). In addition, among the compounds represented by the general formula (A), the compound where $R^6$ in the general formula (A) is other than a hydrogen atom (a compound represented by the following general formula ($A_2$)) may be synthesized, for example, by reacting the compound represented by the general formula (III) synthesized by the method described above with a compound represented by the general formula (IV), under presence of a base, to obtain the compound represented by the general formula (V), and subsequently by reacting the compound represented by the general formula (V) with a carboxylic acid represented by the general formula ($B_1$—H), ($B_2$—H), ($B_3$—H) or ($B_4$—H).

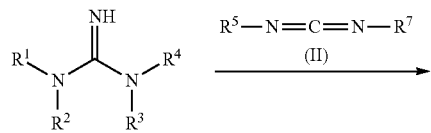

(I)

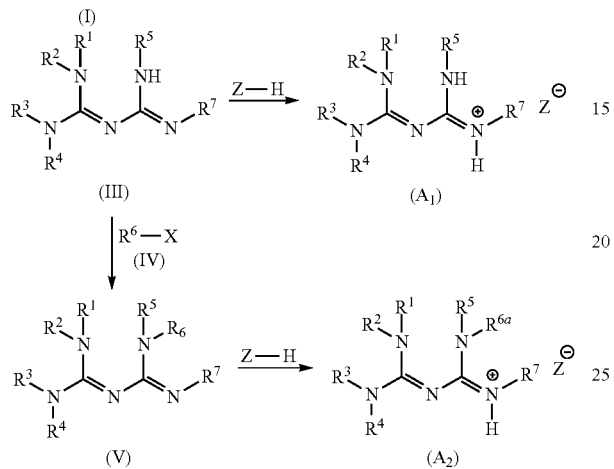

(I)

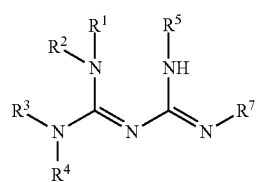

(wherein $R^1$ to $R^4$ are the same as described above.)

$R^5$=N=C=N—$R^7$ (II)

(wherein $R^5$ to $R^7$ are the same as described above.)

(III)

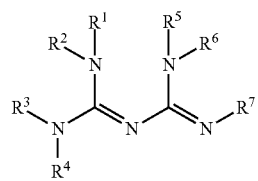

(wherein $R^1$ to $R^5$ and $R^7$ are the same as described above.)

$R^6$—X (IV)

(wherein X represents a halogen atom and $R^6$ is the same as described above.)

(V)

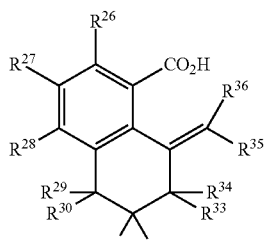

(wherein $R^1$ to $R^7$ are the same as described above.)

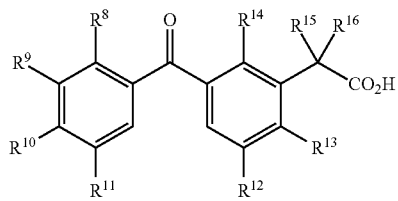

($B_1$-H)

(wherein $R^8$ to $R^{16}$ are the same as described above.)

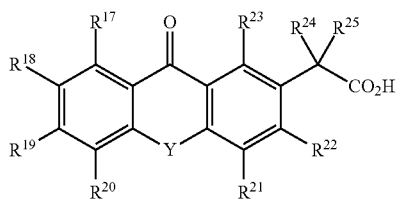

($B_2$-H)

(wherein $R^{17}$ to $R^{25}$ and Y are the same as described above.)

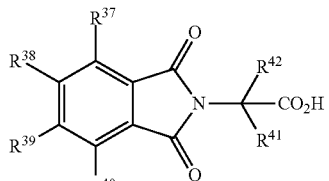

($B_3$-H)

(wherein $R^{26}$ to $R^{36}$ are the same as described above.)

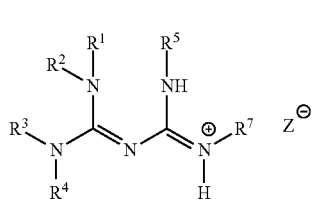

($B_4$-H)

(wherein $R^{37}$ to $R^{42}$ are the same as described above.)

($A_1$)

(wherein $R^1$ to $R^5$, $R^7$ and $Z^-$ are the same as described above.)

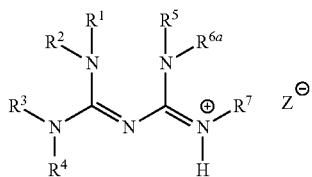

(A₂)

(wherein $R^{6a}$ is an alkyl group having 1 to 12 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group, and a thioxanthonyl group; an alkenyl group having 2 to 12 carbon atoms; an alkynyl group having 2 to 12 carbon atoms; an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group; or an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group, and $R^1$ to $R^5$, $R^7$ and $Z^-$ are the same as the described above.)

A halogen atom represented by X in the general formula (IV) specifically includes, for example, a chlorine atom, a bromine atom, an iodine atom, etc., and among them, an iodine atom is preferable.

Specific examples of "an alkyl group having 1 to 12 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group" represented by $R^{6a}$ in the general formula (A₂), include those similar to specific examples of "an alkyl group having 1 to 12 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group" represented by $R^6$ in the general formula (A), and also preferable specific examples include the same.

Specific examples of the alkenyl group having 2 to 12 carbon atoms represented by $R^{6a}$ in the general formula (A₂), include those similar to specific examples of an alkenyl group having 2 to 12 carbon atoms represented by $R^6$ in the general formula (A), and also specific examples of the preferable alkenyl group and the more preferable alkenyl group include the same.

Specific examples of "an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group" represented by $R^{6a}$ in the general formula (A₂), include those similar to specific examples of "an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group" represented by $R^1$ to $R^7$ in the general formula (A), and also preferable specific examples include the same.

Specific examples of "an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group" represented by $R^{6a}$ in the general formula (A₂), include those similar to specific examples of "an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group" represented by $R^1$ to $R^7$ in the general formula (A), and also preferable specific examples include the same.

Specific examples of the guanidine derivative represented by the general formula (I) in the production method of the compound represented by the general formula (A) of the present invention include, for example, 1,1,3,3-tetramethylguanidine, 1,1,3,3-tetraethylguanidine, 1,1,3,3-tetra-n-propylguanidine, 1,1,3,3-tetraisopropylguanidine, 1,1,3,3-tetra-n-butylguanidine, 1,1,3,3-tetraisobutylguanidine, 1,1,3,3-tetra-sec-butylguanidine, 1,1,3,3-tetra-tert-butylguanidine, 1,1,3,3-tetracyclobutylguanidine, 1,1,3,3-tetra-n-pentylguanidine, 1,1,3,3-tetraisopentylguanidine, 1,1,3,3-tetra-sec-pentylguanidine, 1,1,3,3-tetra-tert-pentylguanidine, 1,1,3,3-tetraneopentylguanidine, 1,1,3,3-tetracyclopentylguanidine, 1,1,3,3-tetra-n-hexylguanidine, 1,1,3,3-tetraisohexylguanidine, 1,1,3,3-tetra-sec-hexylguanidine, 1,1,3,3-tetra-tert-hexylguanidine, 1,1,3,3-tetraneohexylguanidine, 1,1,3,3-tetracyclohexylguanidine, 1,1,3,3-tetra-n-heptylguanidine, 1,1,3,3-tetraisoheptylguanidine, 1,1,3,3-tetra-sec-heptylguanidine, 1,1,3,3-tetra-tert-heptylguanidine, 1,1,3,3-tetraneoheptylguanidine, 1,1,3,3-tetracycloheptylguanidine, 1,1,3,3-tetra-n-octylguanidine, 1,1,3,3-tetraisooctylguanidine, 1,1,3,3-tetra-sec-octylguanidine, 1,1,3,3-tetra-tert-octylguanidine, 1,1,3,3-tetraneooctylguanidine, 1,1,3,3-tetracyclooctylguanidine, 1,1,3,3-tetra-n-nonylguanidine, 1,1,3,3-tetraisononylguanidine, 1,1,3,3-tetra-sec-nonylguanidine, 1,1,3,3-tetra-tert-nonylguanidine, 1,1,3,3-tetraneononylguanidine, 1,1,3,3-tetracyclononylguanidine, 1,1,3,3-tetra-n-decylguanidine, 1,1,3,3-tetraisodecylguanidine, 1,1,3,3-tetra-sec-decylguanidine, 1,1,3,3-tetra-tert-decylguanidine, 1,1,3,3-tetraneodecylguanidine, 1,1,3,3-tetracyclodecylguanidine, 1,1,3,3-tetra-n-undecylguanidine, 1,1,3,3-tetracycloundecylguanidine, 1,1,3,3-tetra-n-dodecylguanidine, 1,1,3,3-tetracyclododecylguanidine, 1,1,3,3-tetranorbornylguanidine, 1,1,3,3-tetrabornylguanidine, 1,1,3,3-tetramenthylguanidine, 1,1,3,3-tetraadamantylguanidine, 1,1,3,3-tetra(decahydronaphthyl)guanidine, 1,1,3,3-tetraphenylguanidine, 1,1,3,3-tetranaphthylguanidine, 1,1,3,3-tetraanthracenylguanidine, 1,1,3,3-tetraphenanthrenylguanidine, 1,1,3,3-tetrabenzylguanidine, 1,1,3,3-tetraphenethylguanidine, 1,1,3,3-tetra(methylbenzyl)guanidine, 1,1,3,3-tetra(phenylpropyl)guanidine, 1,1,3,3-tetra(phenylbutyl)guanidine, 1,1,3,3-tetra(tetrahydronaphthyl)guanidine, 1,1,3,3-tetra(naphthylmethyl)guanidine, 1,1,3,3-tetra(naphthylethyl)guanidine, 1,1,3,3-tetraindenylguanidine, 1,1,3,3-tetrafluorenylguanidine, 1,1,3,3-tetra(anthracenylmethyl)guanidine, 1,1,3,3-tetra(phenanthrenylmethyl)guanidine, 1,5,7-triazabicyclo[4.4.0]deca-5-ene (TBD), etc. It should be noted that as guanidine or a guanidine derivative represented by the general formula (I), a commercially available one, or the one synthesized as appropriate by a method known per se may be used.

Specific examples of the carbodiimide derivative represented by the general formula (II) in the production method of the compound represented by the general formula (A) of the present invention include, for example, N,N'-diethylcarbodiimide, N,N'-diisopropylcarbodiimide, N-tert-butyl-N'-ethylcarbodiimide, N,N'-di-tert-butylcarbodiimide, N,N'-dicyclohexylcarbodiimide, N-[3-(dimethylamino)propyl]-N'- ethylcarbodiimide, N,N'-bis(2,6-diisopropylphenyl)carbodiimide, N,N'-bis(2,2-dimethyl-1,3-dioxolane-4-ylmethyl)carbodiimide, 1-cyclohexyl-3-phenylcarbodiimide, 1-(2-ethyl)hexyl-3-phenylcarbodiimide, 1-(3,4-dimethoxyphenyl)-3-phenylcarbodiimide, etc. It should be noted that, as a carbodiimide derivative represented by the general formula (II), a commercially available one, or the one synthesized as appropriate by a method known per se may be used.

Specific examples of the compound represented by the general formula (IV) in the production method of the compound represented by the general formula (A) of the present invention include, for example, methyl chloride, methyl bromide, methyl iodide, ethyl chloride, ethyl bromide, ethyl iodide, propyl chloride, propyl bromide, propyl iodide, butyl chloride, butyl bromide, butyl iodide, pentyl chloride, pentyl bromide, pentyl iodide, hexyl chloride, hexyl bromide, hexyl iodide, heptyl chloride, heptyl bromide, heptyl iodide, octyl chloride, octyl bromide, octyl iodide, nonyl chloride, nonyl bromide, nonyl iodide, decyl chloride, decyl bromide, decyl iodide, undecyl chloride, undecyl bromide, undecyl iodide, dodecyl chloride, dodecyl bromide, dodecyl iodide, norbornyl chloride, norbornyl bromide, norbornyl iodide, bornyl chloride, bornyl bromide, bornyl iodide, menthyl chloride, menthyl bromide, menthyl iodide, adamantyl chloride, adamantyl bromide, adamantyl iodide, decahydronaphthyl chloride, decahydronaphthyl bromide, decahydronaphthyl iodide, propenyl chloride (allyl chloride), propenyl bromide (allyl bromide), propenyl iodide (allyl iodide), butenyl chloride, butenyl bromide, butenyl iodide, pentenyl chloride, pentenyl bromide, pentenyl iodide, hexenyl chloride, hexenyl bromide, hexenyl iodide, heptenyl chloride, heptenyl bromide, heptenyl iodide, octenyl chloride, octenyl bromide, octenyl iodide, nonenyl chloride, nonenyl bromide, nonenyl iodide, decenyl chloride, decenyl bromide, decenyl iodide, propynyl chloride, propynyl bromide, propynyl iodide, butynyl chloride, butynyl bromide, butynyl iodide, pentynyl chloride, pentynyl bromide, pentynyl iodide, hexynyl chloride, hexynyl bromide, hexynyl iodide, heptynyl chloride, heptynyl bromide, heptynyl iodide, octynyl chloride, octynyl bromide, octynyl iodide, nonynyl chloride, nonynyl bromide, nonynyl iodide, decynyl chloride, decynyl bromide, decynyl iodide, chlorobenzene, bromobenzene, iodobenzene, chloronaphthalene, bromonaphthalene, iodonaphthalene, chloroanthracene, bromoanthracene, iodoanthracene, chlorophenanthrene, bromophenanthrene, iodophenanthrene, benzyl chloride, benzyl bromide, benzyl iodide, phenethyl chloride, phenethyl bromide, phenethyl iodide, methylnaphthyl chloride, methylnaphthyl bromide, methylnaphthyl iodide, ethylnaphthyl chloride, ethylnaphthyl bromide, ethylnaphthyl iodide, fluorenyl chloride, fluorenyl bromide, fluorenyl iodide, methylanthryl chloride, methylanthryl bromide, methylanthryl iodide, methylphenanthryl chloride, methylphenanthryl bromide, methylphenanthryl iodide, epichlorohydrin, epibromohydrin, epiiodohydrin, tert-butyl chloropropionate, tert-butyl bromopropionate, tert-butyl iodopropionate, tert-butyl chlorodimethylacetate, tert-butyl bromodimethylacetate, tert-butyl iododimethylacetate, 3-(2-chloroacetyl)-2H-1-benzopyran, 3-(2-bromoacetyl)-2H-1-benzopyran, 3-(2-iodoacetyl)-2H-1-benzopyran, 2-(1-chloroethyl)anthraquinone, 2-(1-bromoethyl)anthraquinone, 2-(1-iodoethyl)anthraquinone, 2-(2-chloro-2-methylethyl)thioxanthone, 2-(2-bromo-2-methylethyl)thioxanthone, 2-(2-iodo-2-methylethyl)thioxanthone, etc. It should be noted that in the above-described specific examples, an alkyl halide; an alkyl halide having a substituent selected from the group consisting of an epoxy group, an alkoxycarbonyl group, a coumarinylcarbonyl group, an anthraquinonyl group, a xanthonyl group and a thioxanthonyl group; an alkenyl halide; an alkynyl halide; and an arylalkyl halide are not limited to a normal-form, and an alkyl group of a branched-form group, such as sec-form, tert-form, iso-form, neo-form, or an alkyl group of a cyclo-form, such as cyclic-form are also contained in the above-described specific examples. In addition, as such a compound represented by the general formula (IV), a commercially available one, or the one synthesized as appropriate by a method known per se may be used.

Specific examples of the carboxylic acid represented by the general formula ($B_1$—H) in the production method of the compound represented by the general formula (A) of the present invention includes, for example, 3-benzoylphenyl acetic acid, ketoprofen, 2-acetoxymethyl-2-(3-benzoylphenyl)propionic acid, 2-(3-benzoylphenyl)-3-chloro-2-methyl propionic acid, 2-(3-benzoylphenyl)-3-bromo-2-methyl propionic acid, 2-(3-benzoylphenyl)-3-iodo-2-methyl propionic acid, etc. It should be noted that as such a carboxylic acid represented by the general formula ($B_1$—H), a commercially available one, or the one synthesized as appropriate by a method known per se may be used.

Specific examples of the carboxylic acid represented by the general formula ($B_2$—H) in the production method of the compound represented by the general formula (A) of the present invention include, for example, (9-oxo-9H-xanthene-2-yl) acetic acid, 2-(9-oxo-9H-xanthene-2-yl)propionic acid, 3-acetoxy-2-methyl-2-(9-oxo-9H-xanthene-2-yl) propionic acid, 3-chloro-2-methyl-2-(9-oxo-9H-xanthene-2-yl)propionic acid, 3-bromo-2-methyl-2-(9-oxo-9H-xanthene-2-yl)propionic acid, 3-iodo-2-methyl-2-(9-oxo-9H-xanthene-2-yl)propionic acid, etc. It should be noted that as such a carboxylic acid represented by the general formula ($B_2$—H), a commercially available one, or the one synthesized as appropriate by a method known per se may be used.

Specific examples of the carboxylic acid represented by the general formula ($B_3$—H) in the production method of the compound represented by the general formula (A) of the present invention include, for example, 8(7H)-ethylidene-4-methoxy-5,6-dihydronaphthalene-1-carboxylic acid, 8(7H)-ethylidene-2-methoxy-5,6-dihydronaphthalene-1-carboxylic acid, etc. It should be noted that as such a carboxylic acid represented by the general formula ($B_3$—H), a commercially available one, or the one synthesized as appropriate by a method known per se may be used.

Specific examples of the carboxylic acid represented by the general formula ($B_4$—H) in the production method of the compound represented by the general formula (A) of the present invention include, for example, N-phthaloylglycine, phthaloyl-D,L-alanine, 2-(5-nitro-1,3-dioxoisoindoline-2-yl) acetic acid, etc. It should be noted that as such a carboxylic acid represented by the general formula ($B_4$—H), a commercially available one, or the one synthesized as appropriate by a method known per se may be used.

Specific examples of the base to be used in a reaction to obtain the compound represented by the general formula (V), by reacting the compound represented by the general formula (III) with the compound represented by the general formula (IV), include, an alkaline metal hydride, such as, for example, sodium hydride, potassium hydride; an alkaline metal alkoxide, such as, for example, sodium methoxide, potassium methoxide, sodium ethoxide, potassium ethoxide, lithium tert-butoxide, sodium tert-butoxide, potassium tert-butoxide; an alkyl lithium, such as, for example, n-butyllithium, sec-butyllithium, tert-butyllithium, n-hexyllithium;

an alkaline metal hydroxide, such as, for example, sodium hydroxide, potassium hydroxide; an alkaline metal carbonate, such as, for example, sodium carbonate, potassium carbonate, cesium carbonate; a tertiary amine, such as, for example, triethylamine, pyridine, 1,8-diazabicyclo[5.4.0]undeca-7-ene (DBU), 1,5-diazabicyclo[4.3.0]nona-5-ene (DBN); a metal amide, such as, for example, lithium diisopropyl amide (LDA), lithium hexamethyldisilazane (LHMDS), sodium hexamethyldisilazane (NaHMDS), potassium hexamethyldisilazane (KHMDS), etc., and among them, an alkaline metal hydride, such as, for example, sodium hydride, potassium hydride, is preferable. It should be noted that, as such a base, one kind of the base may be used alone, or two or more kinds of the bases may be used in combination. In addition, as such a base, a commercially available one may be used.

In the production method of the compound represented by the general formula (A) of the present invention, use amount of the carbodiimide derivative represented by the above-described general formula (II) is not especially limited, as long as it is practical amount, and it is, for example, usually 0.8 to 10 equivalents, preferably 0.9 to 5 equivalents, and more preferably 1 to 2 equivalents, relative to mole number of guanidine or the guanidine derivative represented by the general formula (I). When the use amount of the carbodiimide derivative is extremely small, yield of the compound represented by the general formula (III) is likely to be decreased. On the other hand, when the use amount of the carbodiimide derivative is very large, a problem such as impairing economic performance occurs.

In the production method of the compound represented by the general formula (A) of the present invention, use amount of the compound represented by the above-described general formula (IV) is not especially limited, as long as it is practical amount, and it is, for example, usually 0.8 to 10 equivalents, preferably 0.9 to 5 equivalents, and more preferably 1 to 2 equivalents, relative to mole number of the compound represented by the general formula (III). When the use amount of the compound represented by the above-described general formula (IV) is extremely small, yield of the compound represented by the general formula (V) is likely to be decreased. On the other hand, when the use amount of the compound represented by the above-described general formula (IV) is very large, a problem such as impairing economic performance occurs.

In the production method of the compound represented by the general formula (A) of the present invention, use amount of the carboxylic acid represented by the above-described general formulae ($B_1$—H), ($B_2$—H), ($B_3$—H) and ($B_4$—H) is not especially limited, as long as it is practical amount, and it is, for example, usually 0.8 to 10 equivalents, preferably 0.9 to 5 equivalents, and more preferably 1 to 2 equivalents, relative to mole number of the compound represented by the general formula (III) or the general formula (V). When the use amount of the carboxylic acid is extremely small, yield of the compound represented by the general formula ($A_1$) or ($A_2$) of the present invention is likely to be decreased. On the other hand, when the use amount of the carboxylic acid is very large, a problem such as impairing economic performance occurs.

In the production method of the compound represented by the general formula (A) of the present invention, use amount of the base to be used in a reaction to obtain the compound represented by the above-described general formula (V) is not especially limited, as long as it is practical amount, and it is, for example, usually 0.8 to 10 equivalents, preferably 0.9 to 5 equivalents, and more preferably 1 to 2 equivalents, relative to mole number of the compound represented by the general formula (III). When the use amount of the base is extremely small, yield of the compound represented by the general formula (V) is likely to be decreased. On the other hand, when the use amount of the base is very large, a problem such as impairing economic performance occurs.

A series of reactions in the production method of the compound represented by the general formula (A) of the present invention, may be carried out under solvent-free condition, or in an organic solvent. Specific examples of the organic solvent is not especially limited, as long as it is an organic solvent which does not react with guanidine or a guanidine derivative, a carbodiimide derivative, a carboxylic acid, the compounds represented by the general formula (III), (IV) and (V), and a base, and include, for example, an aliphatic hydrocarbon-based solvent, such as, for example, hexane, heptane, octane; an aromatic hydrocarbon-based solvent, such as, for example, benzene, toluene, xylene; a halogen-based solvent, such as, for example, dichloromethane, trichloromethane (chloroform), tetrachloromethane (carbon tetrachloride); an ether-based solvent, such as, for example, diethyl ether, diisopropyl ether, methyl tert-butyl ether, cyclopentyl methyl ether, tetrahydrofuran, 2-methyltetrahydrofuran, 1,4-dioxane; a glycol ether-based solvent, such as, for example, ethylene glycol dimethyl ether, propylene glycol dimethyl ether, ethylene glycol diethyl ether, propylene glycol diethyl ether, diethylene glycol dimethyl ether, dipropylene glycol dimethyl ether, dipropylene glycol diethyl ether; a glycol ether acetate-based solvent, such as, for example, ethylene glycol monoethyl ether acetate, diethylene glycol monoethyl ether acetate, diethylene glycol monobutyl ether acetate, propylene glycol monomethyl ether acetate, propylene glycol monoethyl ether acetate, dipropylene glycol monomethyl ether acetate, dipropylene glycol monoethyl ether acetate; a ketone-based solvent, such as, for example, 2-propanone (acetone), 2-butanone (ethyl methyl ketone), 4-methyl-2-pentanone (methyl isobutyl ketone); an ester-based solvent, such as, for example, ethyl acetate, n-propyl acetate, isopropyl acetate, isobutyl acetate, sec-butyl acetate, tert-butyl acetate, ethyl butyrate, isoamyl butyrate; an amide-based solvent, such as, for example, N,N-dimethylformamide, N,N-dimethylacetamide, 1-methyl-2-pyrrolidinone (N-methylpyrrolidone), 1,3-dimethyl-2-imidazolidinone (dimethylethylene urea); a nitrile-based solvent, such as, for example, acetonitrile. It should be noted that, as such an organic solvent, one kind of the organic solvent may be used alone, or two or more kinds of the organic solvents may be used in combination. In addition, as such an organic solvent, a commercially available one may be used.

Use amount of the above-described organic solvent is not especially limited, as long as it is practical amount, and it is, for example, usually 0.01 to 500 mL, and preferably 0.1 to 100 mL, relative to 1 mmol of the compound represented by the general formula (III) or the compound represented by the general formula (V).

It is desirable that a series of reactions, in the production method of the compound represented by the general formula (A) of the present invention, are carried out under conditions (reaction temperature, pressure and reaction time) shown below.

It is desirable that temperature in the reaction (reaction temperature) of guanidine or the guanidine derivative represented by the general formula (I) with the carbodiimide derivative represented by the general formula (II) is set at temperature where the compound represented by the general formula (III) is obtained in good yield, by the efficient reaction of guanidine or the guanidine derivative and the carbodiimide derivative. Specifically, it is, for example, usually 0 to 180° C., and preferably 20 to 150° C.

It is desirable that temperature in the reaction (reaction temperature) of the compound represented by the general formula (III) with the compound represented by the general formula (IV) is set at temperature where the compound represented by the general formula (V) is obtained in good yield, by the efficient reaction of the compound represented by the general formula (III) and the compound represented by the general formula (IV). Specifically, it is, for example, usually −20 to 100° C., and preferably 0 to 80° C.

It is desirable that temperature in the reaction (reaction temperature) of the compound represented by the general formula (III) or the general formula (V) with the carboxylic acid represented by the general formulae ($B_1$—H), ($B_2$—H), ($B_3$—H) and ($B_4$—H) is set at temperature where the compound represented by the general formula ($A_1$) or the general formula ($A_2$) of the present invention is obtained in good yield, by the efficient reaction of the compound represented by the general formula (III) or the general formula (V) and the carboxylic acid. Specifically, it is, for example, usually −20 to 100° C., and preferably 0 to 80° C.

Pressure in a series of reactions, in the production method of the compound represented by the general formula (A) of the present invention, is not especially limited, as long as a series of reactions are carried out without delay, and the reactions may be carried out, for example, under normal pressure.

There may be the case where reaction time of a series of reactions, in the production method of the compound represented by the general formula (A) of the present invention, is influenced by a kind of guanidine or the guanidine derivative, the carbodiimide derivative, the carboxylic acid, the compounds represented by the general formulae (III), (IV) and (V), and the base, use amount of such a compound and the base, presence or absence of an organic solvent, and a kind of the organic solvent, reaction temperature, pressure in the reaction, etc. Therefore, desirable reaction time cannot be said unconditionally, however, it is, for example, usually 1 minute to 24 hours, and preferably 3 minutes to 12 hours.

A series of products after the reaction, in the production method of the compound represented by the general formula (A) of the present invention, can be isolated by a general post-treatment procedure and purification procedure usually carried out in this field. As a specific example of the isolation method, the products can be isolated, for example, by adding a non-polar solvent, such as hexane, into a reaction system, as needed, and after cooling, by filtration of the resulting crystal. In addition, the products may be isolated by filtration or washing of the reaction solution, as needed, or by carrying out re-crystallization, distillation, column chromatography, etc., of the residue obtained by concentration of the reaction solution.

Conventionally known synthesis of biguanides not only had a problem of safety, such as use of cyanogen chloride having high toxicity and corrosive property, or use of antimony which is an super strong acid, but also required multistep synthesis, however, the compound represented by the general formula (III) or the general formula (V) in the above-described production method can be synthesized by using safe raw materials and can be synthesized in a short process simply and conveniently, therefore, the compound represented by the general formula (A) of the present invention, obtained from such compounds, can be synthesized safely, as well as simply and conveniently.

—A Base Generator of the Present Invention—

The base generator of the present invention is a base generator comprising the compound represented by the above-described general formula (A) of the present invention.

The base generator of the present invention is a base generator which generates a base by irradiation of active energy ray, such as, for example, ultraviolet rays, visible rays, infrared rays, X-rays, and generates a base by irradiation of active energy ray having particularly a wavelength of 100 to 700 nm, preferably a wavelength of 200 to 500 nm. The base generator of the present invention is capable of generating a base efficiently, because of presence of an absorption wavelength region with high molar absorption coefficient, in a region of a wavelength of 200 to 500 nm. In addition, as the base generator of the present invention, such a base generator is preferable that shows absorption of active energy ray of at least one or more of i-rays, h-rays, and g-rays, among the above-described wavelength regions, in view of general-purpose. It should be noted that the base generator of the present invention is a base generator which generates a base by irradiation of active energy ray, but it should not exclude generation of a base by giving energy other than photo energy, such as, for example, heating.

It is preferable that the base generator of the present invention has a temperature, at which 5% weight from the initial weight by heating is reduced, (hereafter it may be abbreviated as 5% weight decrease temperature) of 150° C. or higher. In the case of preparing a cured film using the base generator of the present invention, there is the case where baking etc. is carried out, and when the 5% weight decrease temperature of the base generator is high, baking temperature can be set high, therefore, after baking, for example, the residue of an organic solvent contained in a base-reactive composition of the present invention, to be described later, can be decreased as small as possible. In this way, deterioration of contrast between an exposed area (cured area) and an unexposed area (uncured area), caused by the remaining organic solvent, can be suppressed.

Among the base generators of the present invention, the base generator of the present invention, having the anion derived from a carboxylic acid, represented by the general formula ($B_3$), generates a base by irradiation of active energy ray, as well as leads to a lactone structure with progress of photocyclization within a molecule. Since a strong base (biguanides) is generated without accompanying decarboxylation in this photocyclization, different from other base generators accompanying decarboxylation, decrease in film strength of a cured film caused by by-producing of carbon dioxide gas, or generation of film roughening of the surface of the cured film can be avoided.

—A Base-Reactive Composition of the Present Invention—

The base-reactive composition of the present invention is a composition comprising the base generator of the present invention and a base-reactive compound.

A base-reactive compound contained in the base-reactive composition of the present invention is not especially limited, as long as it is a compound which reacts by an action of a strong base (biguanides) generated from the base generator of the present invention, and cures by cross-linking, etc. Specific examples of the base-reactive compound include, for example, an epoxy-based compound having at least one epoxy group, for example, a silicon-based compound having at least one alkoxysilyl group or a silanol group, for example, an isocyanate-based compound having at least one isocyanate group, for example, a polyamic acid-based compound having at least one amide bond, etc. As such a base-reactive compound, one kind of the base-reactive compound may be used alone, or two or more kinds of the base-reactive compounds may be used in combination.

The epoxy-based compound (epoxy-based resin) may be any of a monomer, an oligomer or a polymer, and specifically includes, for example, diglycidyl ether, ethylene glycol diglycidyl ether, spiroglycol diglycidyl ether, diethylene glycol diglycidyl ether, propylene glycol diglycidyl ether, tripropylene glycol diglycidyl ether, butandiol diglycidyl ether, glycerin diglycidyl ether, glycidylpropoxy trimethoxy silane, allyl glycidyl ether, butyl glycidyl ether, neopentyl glycol diglycidyl ether, 1,6-hexanediol diglycidyl ether, phenyl glycidyl ether, cresyl glycidyl ether, alkylphenol glycidyl ether, aliphatic diglycidyl ether, polyfunctional glycidyl ether, tertiary aliphatic acid monoglycidyl ether, polyethylene glycol diglycidyl ether, polypropylene glycol diglycidyl ether, polyglycidyl methacrylate, glycerin polyglycidyl ether, diglycerin polyglycidyl ether, trimethylolpropane polyglycidyl ether, sorbitol polyglycidyl ether, etc. Such an epoxy-based compound may be halogenated or hydrogenated. In addition, as such an epoxy-based compound, a derivative of the above-described specific examples is also included. It should be noted that, as such an epoxy-based compound, one kind of the epoxy-based compound may be used alone, or two or more kinds of the epoxy-based compounds may be used in combination. In addition, as such an epoxy-based compound, a commercially available one, or the one synthesized as appropriate by a method known per se may be used.

In the case where the epoxy-based compound (epoxy-based resin) is an oligomer or a polymer, it is preferable to set weight average molecular weight, at 100 to 30,000, and more preferably at 200 to 20,000, in view of heat resistance, coating properties, solubility to an organic solvent, solubility to a developing solution of the base-reactive composition of the present invention, etc. When the weight average molecular weight is below 100, strength of a cured film or a molded article obtained from the base-reactive composition of the present invention is likely to be insufficient. On the other hand, when the weight average molecular weight is over 30,000, not only viscosity of the epoxy-based compound (epoxy-based resin) itself increases, which deteriorates solubility, but also it is likely to be difficult to obtain a cured film having uniform surface and constant film thickness of the cured film. It should be noted that weight average molecular weight is a value measured by gel permeation chromatography and then converted to standard polystyrene.

The silicon-based compound (silicon-based resin) may be any of a monomer, an oligomer or a polymer, and specifically includes, for example, an alkoxysilane compound or a silane coupling agent, etc. Specific examples of the alkoxysilane compound includes, for example, trimethylmethoxysilane, dimethyldimethoxysilane, methyltrimethoxysilane, tetramethoxysilane, trimethylethoxysilane, dimethyldiethoxysilane, methyltriethoxysilane, tetraethoxysilane, diphenyldimethoxysilane, phenyltrimethoxysilane, diphenyldiethoxysilane, phenyltriethoxysilane, hexyltrimethoxysilane, tetrapropoxysilane, tetrabutoxysilane, poly-3-(methyldimethoxysilyl)propyl methacrylate, poly-3-(methyldiethoxysilane)propyl methacrylate, poly-3-(trimethoxysilyl)propyl methacrylate, poly-3-(triethoxysilyl)propyl methacrylate, etc. As such an alkoxysilane compound, one kind of the alkoxysilane compound may be used alone, or two or more kinds of the alkoxysilane compounds may be used in combination. It should be noted that, as such an alkoxysilane compound, a commercially available one, or the one synthesized as appropriate by a method known per se may be used.

Specific examples of the silane coupling agent include, for example, a vinylsilane, an acrylsilane, an epoxysilane, an aminosilane, etc. Specific examples of the vinylsilane include, for example, vinyltrichlorosilane, vinyltris(β-methoxyethoxy)silane, vinyltriethoxysilane, vinyltrimethoxysilane, etc.

Specific examples of the acrylsilane include, for example, γ-methacryloxypropyltrimethoxysilane, γ-methacryloxypropylmethyldimethoxysilane, etc. Specific examples of the epoxysilane include, for example, β-(3,4-epoxycyclohexyl)ethyltrimethoxysilane, γ-glycidoxypropyltrimethoxysilane, γ-glycidoxypropylmethyldiethoxysilane, etc. Specific examples of the aminosilane include, for example, N-β-(aminoethyl)-γ-aminopropyltrimethoxysilane, N-β-(aminoethyl)-γ-aminopropylmethyldimethoxysilane, γ-aminopropyltrimethoxysilane, N-phenyl-γ-aminopropyltrimethoxysilane, etc. Specific examples of a silane coupling agent other than the above-described silane coupling agent include, for example, γ-mercaptopropyltrimethoxysilane, γ-chloropropylmethyldimethoxysilane, γ-chloropropylmethyldiethoxysilane, etc. As such a silane coupling agent, one kind of the silane coupling agent may be used alone, or two or more kinds of the silane coupling agents may be used in combination. It should be noted that, as such a silane coupling agent, a commercially available one, or the one synthesized as appropriate by a method known per se may be used.

In the case where the silicon-based compound (silicon-based resin) is an oligomer or a polymer, it is preferable to set weight average molecular weight, at 100 to 30,000, and more preferably at 200 to 20,000, in view of heat resistance, coating properties, solubility to an organic solvent, solubility to a developing solution of the base-reactive composition of the present invention, etc. When the weight average molecular weight is below 100, strength of a cured film or a molded article obtained from the base-reactive composition of the present invention is likely to be insufficient. On the other hand, when the weight average molecular weight is over 30,000, not only viscosity of the silicon-based compound (silicon-based resin) itself increases, which deteriorates solubility, but also it is likely to be difficult to obtain a cured film having uniform surface and constant film thickness of the cured film. It should be noted that weight average molecular weight is a value measured by gel permeation chromatography and then converted to standard polystyrene.

Specific examples of the isocyanate-based compound may be any of a monomer, an oligomer or a polymer, and specifically include, for example, an isocyanate-based compound of a monomer, an isocyanate-based compound of a dimer, etc. Preferable specific examples of the isocyanate-based compound include, for example, toluene-2,4-diisocyanate, toluene-2,6-diisocyanate, m-xylylene diisocyanate, hexahydro-m-xylylene diisocyanate, hexamethylene diisocyanate, isophorone diisocyanate, methylenediphenyl-4,4'-diisocyanate, polymethylene polyphenyl polyisocyanate, etc. As such an isocyanate-based compound, one kind of the isocyanate-based compound may be used alone, or two or more kinds of the isocyanate-based compounds may be used in combination. It should be noted that, as such an isocyanate-based compound, a commercially available one, or the one synthesized as appropriate by a method known per se may be used.

In the case where the isocyanate-based compound is an oligomer or a polymer, it is preferable to set weight average molecular weight, at 100 to 30,000, and more preferably at 200 to 20,000, in view of heat resistance, coating properties, solubility to an organic solvent, solubility to a developing solution of the base-reactive composition of the present invention, etc. When the weight average molecular weight is below 100, strength of a cured film or a molded article obtained from the base-reactive composition of the present invention is likely to be insufficient. On the other hand, when the weight average molecular weight is over 30,000, not only viscosity of the isocyanate-based compound itself increases, which deteriorates solubility, but also it is likely to be difficult to obtain a cured film having uniform surface and constant film thickness of the cured film. It should be noted that weight average molecular weight is a value measured by gel permeation chromatography and then converted to standard polystyrene.

Specific examples of the polyamic acid-based compound include a polyamic acid-based compound (polyamic acid-based resin), etc. known per se obtained by a reaction of an acid anhydride and a diamine. Preferable specific examples of the polyamic acid-based compound include a polyamic acid-based compound (polyamic acid-based resin), etc. obtained, for example, by reacting a tetracarboxylic dianhydride, such as, for example, pyromellitic dianhydride, naphthalenetetracarboxylic dianhydride, biphenyl ether tetracarboxylic dianhydride, benzophenone tetracarboxylic dianhydride, cyclopentanetetracarboxylic dianhydride, cyclohexanetetracarboxylic dianhydride, 4-(1,2-dicarboxyethyl)-1,2,3,4-tetrahydronaphthalene-1,2-dicarboxylic dianhydride, 5-(1,2-dicarboxyethyl)-3-methylcyclohexane-1,2-dicarboxylic dianhydride, with a diamine, such as phenylene diamine, diaminobiphenyl ether, diaminobenzophenone. Such a polyamic acid-based compound may be halogenated or hydrogenated. In addition, as such a polyamic acid-based compound, a derivative of the above-described specific examples is also included. It should be noted that, as such a polyamic acid-based compound, one kind of the polyamic acid-based compound may be used alone, or two or more kinds of the polyamic acid-based compounds may be used in combination. In addition, as such a polyamic acid-based compound, a commercially available one, or the one synthesized as appropriate by a method known per se may be used.

It is preferable to set weight average molecular weight of the polyamic acid-based compound, at 100 to 30,000, and more preferably at 200 to 20,000, in view of heat resistance, coating properties, solubility to an organic solvent, solubility to a developing solution of the base-reactive composition of the present invention, etc. When the weight average molecular weight is below 100, strength of a cured film or a molded article obtained from the base-reactive composition of the present invention is likely to be insufficient. On the other hand, when the weight average molecular weight is over 30,000, not only viscosity of the polyamic acid-based compound itself increases, which deteriorates solubility, but also it is likely to be difficult to obtain a cured film having uniform surface and constant film thickness of the cured film. It should be noted that weight average molecular weight is a value measured by gel permeation chromatography and then converted to standard polystyrene.

A contained amount of the base generator of the present invention contained in the base-reactive composition of the present invention is not especially limited, as long as it is practical amount, and it is, for example, usually 0.1 to 100% by weight, preferably 1 to 50% by weight, and more preferably 5 to 30% by weight, relative to weight of the base-reactive compound. When the contained amount of the base generator is extremely small, curing of the base-reactive composition of the present invention is likely to be insufficient. On the other hand, when the contained amount of the base generator is very large, a problem such as impairing economic performance occurs.

It is desirable that the base-reactive composition of the present invention further contains a thiol-based compound or/and an acid anhydride, as a cross-linking agent.

The thiol-based compound is a compound which acts as a cross-linking agent for curing the epoxy-based compound by reacting with an epoxy group in the epoxy-based compound by a combined use with the epoxy-based compound, etc. The thiol-based compound may be any of a monomer, an oligomer or a polymer, therefore, it is preferable to use the thiol-based compound having two or more thiol groups, and preferable specific examples of the thiol-based compound include, a thiol-based compound having 2 to 5 thiol groups, such as, for example, ethylene glycol bis(3-mercaptobutyrate), butandiol bis(3-mercaptobutyrate), pentaerythritol tetrakis(3-mercaptobutyrate), dipentaerythritol hexakis(3-mercaptobutyrate), ethylene glycol bis(3-mercaptoisobutyrate), butandiol bis(3-mercaptoisobutyrate), pentaerythritol tetrakis(3-mercaptoisobutyrate), dipentaerythritol hexakis(3-mercaptoisobutyrate), trimethylolpropane tris(3-mercaptoisobutyrate), tris[(3-mercaptopropionyloxy)ethyl]isocyanurate, pentaerythritol tetrakis(3-mercaptopropionate), dipentaerythritol hexa(3-mercaptopropionate), trimethylolpropane tris(3-mercaptopropionate), diethylene glycol bis(3-mercaptopropionate), pentaerythritol tetrakis(3-mercaptobutyrate), 1,4-bis(3-mercaptobutyryloxy)butane, 1,3,5-tris(3-mercaptobutyryloxyethyl)-1,3,5-triazine-2,4,6-(1H,3H,5H)-trione, a liquefied polymercaptan, a polysulfide, etc. Among these thiol-based compounds, in consideration of reactivity, etc. and easy handling, pentaerythritol tetrakis(3-mercaptopropionate), pentaerythritol tetrakis(3-mercaptobutyrate), tris[(3-mercaptopropionyloxy)ethyl]isocyanurate are preferable. As such a thiol-based compound, one kind of the thiol-based compound may be used alone, or two or more kinds of the thiol-based compounds may be used in combination. It should be noted that, as such a thiol-based compound, a commercially available one, or the one synthesized as appropriate by a method known per se may be used.

In the case where the thiol-based compound is an oligomer or a polymer, it is preferable to set weight average molecular weight, at 100 to 10,000, and more preferably at 200 to 5,000, in view of heat resistance, coating properties, solubility to an organic solvent, solubility to a developing solution of the base-reactive composition of the present invention, etc. When the weight average molecular weight is below 100, strength of a cured film or a molded article obtained from the base-reactive composition of the present invention is likely to be insufficient. On the other hand, when the weight average molecular weight is over 10,000, not only viscosity of the thiol-based compound itself increases, which deteriorates solubility, but also it is likely to be difficult to obtain a cured film having uniform surface and constant film thickness of the cured film. It should be noted that weight average molecular weight is a value measured by gel permeation chromatography and then converted to standard polystyrene.

As for a contained amount of the thiol-based compound, it is preferable to set so as to attain a ratio of equivalent of the thiol group (equivalent of SH group)/equivalent of the epoxy group=0.3/1.7 to 1.7/0.3, and among them, is more preferable to set so as to attain the ratio of 0.8/1.2 to 1.2/0.8, for example, relative to the epoxy-based compound in the base-reactive compound.

The acid anhydride is a compound which acts as a cross-linking agent for curing the epoxy-based compound by reacting with an epoxy group in the epoxy-based compound by a combined use with the epoxy-based compound, etc. The acid anhydride may be any of a monomer, an oligomer or a polymer, and preferable specific examples of the acid anhydride include, a monofunctional acid anhydride, such as, for example, phthalic anhydride, tetrahydrophthalic anhydride, hexahydrophthalic anhydride, methyltetrahydrophthalic anhydride, methylhexahydrophthalic anhydride, methylnadic anhydride, dodecylsuccinic anhydride, chlorendic anhydride, a bifunctional acid anhydride, such as, for example, pyromellitic dianhydride, benzophenone tetracarboxylic dianhydride, ethylene glycol bis(anhydrotrimellitate), methylcyclohexene tetracarboxylic dianhydride, a free acid anhydride, such as, for example, trimellitic anhydride, poly azelaic anhydride. As such an acid anhydride, one kind of the acid anhydride may be used alone, or two or more kinds of the acid anhydrides may be used in combination. It should be noted that, as such an acid anhydride, a commercially available one, or the one synthesized as appropriate by a method known per se may be used.

In the case where the acid anhydride is an oligomer or a polymer, it is preferable to set weight average molecular weight, at 100 to 10,000, and more preferably at 200 to 5,000, in view of heat resistance, coating properties, solubility to an organic solvent, solubility to a developing solution of the base-reactive composition of the present invention, etc. When the weight average molecular weight is below 100, strength of a cured film or a molded article obtained from the base-reactive composition of the present invention is likely to be insufficient. On the other hand, when the weight average molecular weight is over 10,000, not only viscosity of the acid anhydride itself increases, which deteriorates solubility, but also it is likely to be difficult to obtain a cured film having uniform surface and constant film thickness of the cured film. It should be noted that weight average molecular weight is a value measured by gel permeation chromatography and then converted to standard polystyrene.

As for a contained amount of the acid anhydride, it is preferable to set so as to attain a ratio of equivalent of the acid anhydride group (equivalent of —C(=O)OC(=O)— group)/equivalent of the epoxy group=0.3/2.7 to 2.0/1.0, and among them, is more preferable to set so as to attain the ratio of 0.5/2.5 to 1.5/1.5, for example, relative to the epoxy-based compound in the base-reactive compound.

In the case of coating the base-reactive composition of the present invention onto a predetermined substrate, there is the case where the composition containing an organic solvent is desirable. By containing the organic solvent into the base-reactive composition, coating properties can be enhanced, thus leading to good workability. The organic solvent is not especially limited, as long as it is an organic solvent generally used in this field usually. Specific examples of the organic solvent include, a saturated, or unsaturated aliphatic hydrocarbon-based solvent, such as, for example, pentane, hexane, heptane, octane, nonane, decane, tetrahydronaphthalene, menthane, squalene; an aromatic hydrocarbon-based solvent, such as, for example, benzene, toluene, ethylbenzene, styrene, xylene, diethylbenzene, trimethylbenzene; a halogen-based solvent, such as, for example, dichloromethane, trichloromethane (chloroform), tetrachloromethane (carbon tetrachloride); an ether-based solvent, such as, for example, diethyl ether, di-n-propyl ether, diisopropyl ether, methyl tert-butyl ether, di-n-butyl ether, di-tert-butyl ether, cyclopentyl methyl ether, tetrahydrofuran, 2-methyltetrahydrofuran, 1,4-dioxane; an alcohol-based solvent, such as, for example, methanol, ethanol, n-propanol, isopropanol, n-butanol, isobutanol, sec-butanol, tert-butanol, 2-methoxyethanol; a glycol ether-based solvent, such as, for example, ethylene glycol monomethyl ether, propylene glycol monomethyl ether (PGME), propylene glycol monoethyl ether, diethylene glycol monomethyl ether, dipropylene glycol monomethyl ether, dipropylene glycol monoethyl ether, ethylene glycol dimethyl ether, propylene glycol dimethyl ether, ethylene glycol diethyl ether, propylene glycol diethyl ether, diethylene glycol dimethyl ether, dipropylene glycol dimethyl ether, dipropylene glycol diethyl ether; a glycol ether acetate-based solvent, such as, for example, ethylene glycol monoethyl ether acetate, diethylene glycol monoethyl ether acetate, diethylene glycol monobutyl ether acetate, propylene glycol monomethyl ether acetate (PGMEA), propylene glycol monoethyl ether acetate, dipropylene glycol monomethyl ether acetate, dipropylene glycol monoethyl ether acetate; a ketone-based solvent, such as, for example, 2-propanone (acetone), 2-butanone (ethyl methyl ketone), diethyl ketone, 4-methyl-2-pentanone (methyl isobutyl ketone), cyclopentanone, cyclohexanone, cycloheptanone; an ester-based solvent, such as, for example, methyl acetate, ethyl acetate, n-propyl acetate, isopropyl acetate, isobutyl acetate, sec-butyl acetate, tert-butyl acetate, ethyl butyrate, isoamyl butyrate, ethyl lactate (EL), n-propyl lactate, isopropyl lactate, isobutyl lactate, sec-butyl lactate, tert-butyl lactate, isoamyl lactate, γ-butyrolactone, butyl stearate; an amide-based solvent, such as, for example, N,N-dimethylformamide, N,N-dimethylacetamide, 1-methyl-2-pyrrolidinone (N-methylpyrrolidone), 1,3-dimethyl-2-imidazolidinone (dimethylethylene urea); a nitrile-based solvent, such as, for example, acetonitrile, etc. Among these organic solvents, the glycol ether acetate-based solvent and the ester-based solvent are preferable. The glycol ether acetate-based solvent and the ester-based solvent have the following characteristics (1) because of having suitable boiling point, not only preparation of the composition, which is usually carried out at room temperature, can be carried out stably but also the base generator and the base-reactive compound, etc., little receive adverse influence by heat, because high baking temperature is not necessary, (2) because of having good compatibility with a substrate and good flatting of the base-reactive composition in spin coating, the composition can be coated onto a substrate simply and conveniently, (3) because of having higher solubility of the base generator, as compared with other solvents, phase separation of the base generator is difficult to be caused, for example, in preparing a coated film, and (4) stability is high because the decomposing materials does not indicate basicity, different from the amide-based solvent. It should be noted that, as such an organic solvent, one kind of the organic solvent may be used alone, or two or more kinds of organic solvents may be used in combination. In addition, as such an organic solvent, a commercially available one may be used.

A contained amount of the organic solvent contained, as needed, in the base-reactive composition of the present invention, is not especially limited, as long as it is practical amount, and may be selected as appropriate so as to attain uniform coating, for example, in coating the base-reactive composition onto a predetermined substrate, and forming a layer made of the base-reactive composition, and it is usually 0.01 to 50 mL, preferably 0.05 to 30 mL, and more preferably 0.1 to 10 mL, for example, relative to 1 g of the base-reactive compound.

In the case of using the base-reactive composition of the present invention as a photosensitive resin composition, a sensitizer may be added thereto to enhance sensitivity, by enlarging a photosensitive wavelength region. The sensitizer is not especially limited, as long as it is a sensitizer generally used in this field usually. Preferable specific examples of the sensitizer include, for example, benzophenone, p,p'-tetramethyl diaminobenzophenone, p,p'-tetraethyl aminobenzophenone, 2-chlorothioxanthone, anthrone, 9-ethoxyanthracene, anthracene, pyrene, perylene, phenothiazine, benzil, acridine orange, benzoflavin, setflavin-T, 9,10-diphenylanthracene, 9-fluorenone, acetophenone, phenanthrene, 2-nitrofluorene, 5-nitroacenaphthene, benzoquinone, 2-chloro-4-nitroaniline, N-acetyl-p-nitroaniline, p-nitroaniline, N-acetyl-4-nitro-1-naphthylamine, picramide, anthraquinone, 2-ethylanthraquinone, 2-tert-butylanthraquinone, 1,2-benzanthraquinone, 3-methyl-1,3-diaza-1,9-benzanthrone, dibenzalacetone, 1,2-naphthoquinone, 3,3'-carbonyl-bis(5,7-dimethoxycarbonylcoumarin), coronene, etc. As such a sensitizer, one kind of the sensitizer may be used alone, or two or more kinds of the sensitizers may be used in combination. It should be noted that, as such a sensitizer, a commercially available one, or the one synthesized as appropriate by a method known per se may be used.

A contained amount of the sensitizer contained, as needed, in the base-reactive composition of the present invention, is not especially limited, as long as it is practical amount, and may be determined as appropriate, by the base generator or the base reactive compound to be used, and sensitivity required, etc. In more specifically, in the case where the sensitizer is contained, the contained amount of the sensitizer is preferably 1 to 30% by mass, and among them, 5 to 20% by weight is more preferable, relative to the whole base-reactive composition. When the contained amount of the sensitizer is less than 1% by mass, there is the case where sensitivity cannot be enhanced sufficiently. On the other hand, when the contained amount of the sensitizer is over 30% by mass, there is the case where it is excessive to enhance sensitivity.

The base-reactive composition of the present invention, other than the above-described sensitizer, may contain an additive, such as, for example, a filler, a pigment, a dye, a leveling agent, an anti-foaming agent, an anti-static agent, a pH-adjusting agent, a dispersing agent, a dispersing auxiliary agent, a surface modifier, a plasticizer, a plasticizing accelerator, an anti-sagging agent, a curing accelerator, in an range not interfering the purpose and effect of the present invention. As such an additive, one kind of the additive may be used alone, or two or more kinds of the additives may be used in combination. It should be noted that, as such an additive, a commercially available one, or the one synthesized as appropriate by a method known per se may be used.

A pattern formation using the base-reactive composition of the present invention is carried out, for example, as follows. A coating solution is prepared, for example, by dissolving the composition into an organic solvent, coating thus prepared coating solution to an appropriate solid surface, such as a substrate, and drying to form the coated film. Then a polymerization reaction of the base-reactive compound contained in the base-reactive composition may be promoted by carrying out heating treatment under the predetermined condition, after generating the base by carrying out pattern exposure to the coated film thus formed.

The base-reactive composition of the present invention makes progress of a polymerization reaction even at room temperature, by irradiation of active energy ray, due to containing of the base generator of the present invention, however, it is preferable to carry out baking (heating) treatment to make progress of a polymerization reaction in good efficiency. A condition of the baking (heating) treatment may be determined as appropriate depending on irradiation (exposure) energy, kind of a strong base (biguanides) generating from the base generator to be used, and kind of the base-reactive compound, such as the epoxy-based compound, the silicon-based compound, however, it is preferable that baking (heating) temperature is set within a range of 50° C. to 150° C., and it is more preferable to set within a range of 60° C. to 130° C. In addition, it is preferable to set the baking (heating) time at 10 seconds to 60 minutes, and it is more preferable to set at 60 seconds to 30 minutes. A substrate formed with a coated film after irradiating active energy ray and carrying out heating treatment, as needed, is immersed into a solvent (developing solution), which causes difference of solubility between an exposed area and an unexposed area, and development is carried out, then a pattern can be obtained.

As for a coating method of the base reactive composition of the present invention onto a substrate, a baking method, an irradiation method of active energy ray, a development method, etc., to be carried out in the above-described pattern formation, a method known per se may be adopted as appropriate.

The base-reactive composition of the present invention as explained above, by containing the base generator of the present invention and the base-reactive compound, can be made a composition in which a polymerization reaction of the base-reactive compound proceeds in a chain reaction, using a strong base (biguanides) generated from the base generator by operation, such as irradiation of active energy ray or heating, as an initiator, and curing is carried out quickly and sufficiently. The base-reactive composition of the present invention, which exerts such effect, can be used suitably, for example, for a photo-curing material or a resist material (pattern formation material), etc. having high sensitivity.

In the case when the base-reactive composition of the present invention was used for a curing material, a molded article to be formed after curing operation is widely used, as members, etc. of a field that characteristics, such as heat resistance, dimensional stability, insulation properties, are considered to be effective, for example, as constitutional members of a paint, a printing ink, a color filter, a film for a flexible display, a semiconductor apparatus, electronics parts, an interlayer insulating film, a wiring covering film, an optical circuit, optical circuit parts, an antireflection film, a hologram, optical members or a construction material, and thus a printed matter, a color filter, a film for a flexible display, a semiconductor apparatus, electronics parts, an interlayer insulating film, a wiring covering film, an optical circuit, optical circuit parts, an antireflection film, a hologram, optical parts or a construction material, etc., are provided. In addition, in the case where the base-reactive composition of the present invention was used for a resist material (pattern forming material), the pattern, etc. to be formed after a pattern formation operation is provided with heat resistance and insulation properties, and can be used effectively as, for example, a color filter, a film for a flexible display, electronics parts, a semiconductor apparatus, an interlayer insulating film, a wiring covering film, an optical circuit, optical circuit parts, an antireflection film, other optical parts or electronics parts.

—A Method for Generating a Base of the Present Invention—

The method for generating a base of the present invention is a method, which comprises irradiating active energy ray, such as, for example, ultraviolet rays, visible rays, infrared rays, X-rays, to the compound represented by the general formula (A) of the present invention.

The method for generating a base of the present invention is a method for generating a base, in more specifically, by irradiation of active energy ray having a wavelength of 100 to 700 nm, and preferably a wavelength of 200 to 500 nm, and among the above-described wavelength regions, it is preferable to comprise active energy ray of at least one or more of i-rays, h-rays, and g-rays. In addition, among active energy ray having the above-described wavelength regions, by irradiation of active energy ray having exposure intensity thereof of usually 0.1 to 100 mW/cm$^2$, and preferably 1.0 to 50 mW/cm$^2$, during an irradiation time of 0.01 to 1,000 seconds, and preferably 0.1 to 300 seconds, a strong base (biguanides) can be generated in good efficiency.

—A Compound Represented by the General Formula (E) of the Present Invention—

The compound represented by the following general formula (E) of the present invention, among the compounds represented by the general formula (A) of the present invention, is a compound having property as the base generator, as well as property as the radical generator.

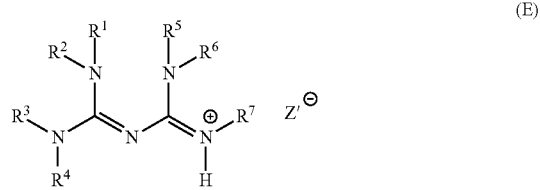

(E)

(wherein $Z'^-$ represents an anion derived from a carboxylic acid, represented by the above-described general formula $(B_1)$ or $(B_2)$, and $R^1$ to $R^7$ are the same as described above.)

More preferable specific examples of the anion derived from a carboxylic acid, represented by $Z'^-$ in the general formula (E) include anions represented by the above-described general formulae $(B_1')$ and $(B_2')$.

As the $Z'^-$ in the general formula (E), the anion derived from a carboxylic acid, represented by the general formula $(B_1)$ is preferable.

—A Radical Generator of the Present Invention—

The radical generator of the present invention is a radical generator comprising the compound represented by the above-described general formula (E) of the present invention, and is a radical generator which generates a radical by irradiation of light (active energy ray) of, for example, ultraviolet rays, visible rays, infrared rays, X-rays, etc., or heating.

In the case where the radical generator of the present invention generates a radical by irradiation of active energy ray, the radical generator of the present invention can generate a radical by irradiation of active energy ray, having particularly a wavelength of 100 to 780 nm, and preferably a wavelength of 200 to 450 nm. The radical generator of the present invention is capable of generating a radical efficiently, because of presence of an absorption wavelength region with high molar absorption coefficient, in a region of a wavelength of 200 to 450 nm. In addition, as the radical generator of the present invention, such a radical generator is preferable that shows absorption of active energy ray of at least one or more of i-rays, h-rays, and g-rays, among the above-described wavelength regions, in view of general-purpose.

In addition, the radical generator of the present invention can be used also as a radical generator in a resist stripping agent in a surface treatment process of a semiconductor, and by using the composition containing the radical generator of the present invention, a residue of a remained resist layer or a residue of a remained antireflection film layer can be removed efficiently, by treating the semiconductor surface where the antireflection film layer, etc. is provided.

In the case used for such a purpose, the radical generator of the present invention may be used, for example, in accordance with the description of WO 2009/110582, and also use amount thereof, other components to be coexisted, or use amount thereof, etc., may be selected as appropriate in accordance with the description of the publication.

Furthermore, it is also possible to use the radical generator of the present invention as a catalyst in a carbon-carbon bond-forming reaction using a radical reaction.

In the case used for such a purpose, the radical generator of the present invention may be used, for example, in accordance with the description of JP-A-11-5033, and also use amount thereof, other components to be coexisted, or use amount thereof, etc., may be selected as appropriate in accordance with the description of the publication.

—A Radical Reactive Composition of the Present Invention—

The radical reactive composition of the present invention is a composition comprising the radical generator of the present invention and a radical-reactive compound.

A radical-reactive compound contained in the radical reactive composition of the present invention is not especially limited, as long as it is a compound, which progresses a polymerization reaction and cures by an action of a radical generated by the radical generator of the present invention. The radical-reactive compound may be a compound having at least one ethylenic unsaturated bond which is radical polymerizable, and preferable specific examples of the radical-reactive compound include, an unsaturated carboxylic acid, such as, for example, an acrylate, a methacrylate, an allylate, itaconic acid, crotonic acid, isocrotonic acid, maleic acid; a radical reactive compound, such as an ester, a urethane, an amide, an amide anhydride, an acid amide, acrylonitrile, styrene, an unsaturated polyester, an unsaturated polyether, an unsaturated polyamide, an unsaturated polyurethane, etc. As such a radical-reactive compound, one kind of the radical-reactive compound may be used alone, or two or more kinds of the radical-reactive compounds may be used in combination.

The acrylates may be any of a monomer, an oligomer or a polymer, and specifically include, for example, monofunctional alkyl acrylates, monofunctional ether group-containing acrylates, monofunctional carboxyl-containing acrylates, bifunctional acrylates, tri or more functional acrylates, etc. Such an acrylate may be halogenated or hydrogenated. In addition, as such an acrylate, a derivative of the above-described specific examples is also included. It should be noted that, as such an acrylate, one kind of the acrylate may be used alone, or two or more kinds of the acrylates may be used in combination. In addition, as such an acrylate, a commercially available one, or the one synthesized as appropriate by a method known per se may be used.

Specific examples of the monofunctional alkyl acrylates include methyl acrylate, ethyl acrylate, propyl acrylate, isopropyl acrylate, butyl acrylate, isoamyl acrylate, hexyl acrylate, 2-ethylhexyl acrylate, octyl acrylate, decyl acrylate, lauryl acrylate, stearyl acrylate, isobornyl acrylate, cyclohexyl acrylate, dicyclopentenyl acrylate, dicyclopentenyloxyethyl acrylate, benzyl acrylate, etc.

Specific examples of the monofunctional ether group-containing acrylates include 2-methoxyethyl acrylate, 1,3-butylene glycol methyl ether acrylate, butoxyethyl acrylate, methoxytriethylene glycol acrylate, methoxypolyethylene glycol #400 acrylate, methoxydipropylene glycol acrylate, methoxytripropylene glycol acrylate, methoxypolypropylene glycol acrylate, ethoxydiethylene glycol acrylate, ethylcarbitol acrylate, 2-ethylhexylcarbitol acrylate, tetrahydrofurfuryl acrylate, phenoxyethyl acrylate, phenoxydiethylene glycol acrylate, phenoxypolyethylene glycol acrylate, cresylpolyethylene glycol acrylate, p-nonylphenoxyethyl acrylate, p-nonylphenoxypolyethylene glycol acrylate, glycidyl acrylate, etc.

Specific examples of the monofunctional carboxyl-containing acrylates include β-carboxyethyl acrylate, succinic acid monoacryloyloxyethyl ester, ω-carboxypolycaprolactone monoacrylate, 2-acryloyloxyethyl hydrogen phthalate, 2-acryloyloxypropyl hydrogen phthalate, 2-acryloyloxypropyl hexahydro hydrogen phthalate, 2-acryloyloxypropyl tetrahydro hydrogen phthalate, etc.

Specific examples of other monofunctional acrylates not included in the monofunctional alkyl acrylates, the monofunctional ether group-containing acrylates and the monofunctional carboxyl-containing acrylates, include N,N-dimethylaminoethyl acrylate, N,N-dimethylaminopropyl acrylate, morpholinoethyl acrylate, trimethylsiloxyethyl acrylate, diphenyl-2-acryloyloxyethyl phosphate, 2-acryloyloxyethyl acid phosphate, caprolactone-modified 2-acryloyloxyethyl acid phosphate, etc.

Specific examples of the bifunctional acrylates include 1,4-butandiol diacrylate, 1,6-hexanediol diacrylate, ethylene glycol diacrylate, diethylene glycol diacrylate, triethylene glycol diacrylate, tetraethylene glycol diacrylate, polyethylene glycol #200 diacrylate, polyethylene glycol #300 diacrylate, polyethylene glycol #400 diacrylate, polyethylene glycol #600 diacrylate, dipropylene glycol diacrylate, tripropylene glycol diacrylate, tetrapropylene glycol diacrylate, polypropylene glycol #400 diacrylate, polypropylene glycol #700 diacrylate, neopentyl glycol diacrylate, neopentyl glycol PO-modified diacrylate, hydroxypivalic acid neopentyl glycol ester diacrylate, caprolactone adduct diacrylate of hydroxypivalic acid neopentyl glycol ester, 1,6-hexanediol bis(2-hydroxy-3-acryloyloxypropyl) ether, bis(4-acryloxypolyethoxyphenyl)propane, 1,9-nonanediol diacrylate, pentaerythritol diacrylate, pentaerythritol diacrylate monostearate, pentaerythritol diacrylate monobenzoate, bisphenol A diacrylate, EO-modified bisphenol A diacrylate, PO-modified bisphenol A diacrylate, hydrogenated bisphenol A diacrylate, EO-modified hydrogenated bisphenol A diacrylate, PO-modified hydrogenated bisphenol A diacrylate, bisphenol F diacrylate, EO-modified bisphenol F diacrylate, PO-modified bisphenol F diacrylate, EO-modified tetrabromobisphenol A diacrylate, tricyclodecane dimethylol diacrylate, isocyanuric acid EO-modified diacrylate, etc.

Specific examples of the tri or more functional acrylates include glycerin PO-modified triacrylate, trimethylolpropane triacrylate, trimethylolpropane EO-modified triacrylate, trimethylolpropane PO-modified triacrylate, isocyanuric acid EO-modified triacrylate, isocyanuric acid EO-modified ε-caprolactone-modified triacrylate, 1,3,5-triacryloylhexahydro-s-triazine, pentaerythritol triacrylate, dipentaerythritol triacrylate tripropionate, pentaerythritol tetraacrylate, dipentaerythritol tetraacrylate, dipentaerythritol pentaacrylate monopropionate, dipentaerythritol hexaacrylate, tetramethylolmethane tetraacrylate, oligo ester tetraacrylate, tris(acryloyloxy) phosphate, etc.

In the case where the acrylate is an oligomer or a polymer, it is preferable to set weight average molecular weight, at 100 to 30,000, and more preferably at 200 to 20,000, in view of heat resistance, coating properties, solubility to an organic solvent, solubility to a developing solution of the radical reactive composition of the present invention, etc. When the weight average molecular weight is below 100, strength of a cured film or a molded article obtained from the radical reactive composition of the present invention is likely to be insufficient. On the other hand, when the weight average molecular weight is over 30,000, not only viscosity of the acrylate itself increases, which deteriorates solubility, but also it is likely to be difficult to obtain a cured film having uniform surface and constant film thickness of the cured film. It should be noted that weight average molecular weight is a value measured by gel permeation chromatography and then converted to standard polystyrene.

The methacrylates may be any of a monomer, an oligomer or a polymer, and specifically include, for example, monofunctional alkyl methacrylates, monofunctional ether group-containing methacrylates, monofunctional carboxyl-containing methacrylates, bifunctional methacrylates, tri or more functional methacrylates, etc. Such a methacrylate may be halogenated or hydrogenated. In addition, as such a methacrylate, a derivative of the above-described specific examples is also included. It should be noted that, as such a methacrylate, one kind of the methacrylate may be used alone, or two or more kinds of the methacrylates may be used in combination. In addition, as such a methacrylate, a commercially available one, or the one synthesized as appropriate by a method known per se may be used.

Specific examples of the monofunctional alkyl methacrylates include methyl methacrylate, ethyl methacrylate, propyl methacrylate, isopropyl methacrylate, butyl methacrylate, isoamyl methacrylate, hexyl methacrylate, 2-hexyl methacrylate, 2-ethylhexyl methacrylate, octyl methacrylate, decyl methacrylate, lauryl methacrylate, stearyl methacrylate, isobornyl methacrylate, cyclohexyl methacrylate, dicyclopentenyl methacrylate, dicyclopentenyloxyethyl methacrylate, benzyl methacrylate, etc.

Specific examples of the monofunctional ether group-containing methacrylates include 2-methoxyethyl methacrylate, 1,3-butylene glycol methyl ether methacrylate, butoxyethyl methacrylate, methoxytriethylene glycol methacrylate, methoxypolyethylene glycol #400 methacrylate, methoxydipropylene glycol methacrylate, methoxytripropylene glycol methacrylate, methoxypolypropylene glycol methacrylate, ethoxydiethylene glycol methacrylate, 2-ethylhexyl carbitol methacrylate, tetrahydrofurfuryl methacrylate, phenoxyethyl methacrylate, phenoxydiethylene glycol methacrylate, phenoxypolyethylene glycol methacrylate, cresyl polyethylene glycol methacrylate, p-nonylphenoxyethyl methacrylate, p-nonylphenoxy polyethylene glycol methacrylate, glycidyl methacrylate, etc.

Specific examples of the monofunctional carboxyl-containing methacrylates include β-carboxyethyl methacrylate, succinic acid monomethacryloyloxyethyl ester, ω-carboxypolycaprolactone monomethacrylate, 2-methacryloyloxyethyl hydrogen phthalate, 2-methacryloyloxypropyl hydrogen phthalate, 2-methacryloyloxypropyl hexahydro hydrogen phthalate, 2-methacryloyloxypropyl tetrahydro hydrogen phthalate, etc.

Specific examples of other monofunctional methacrylates not included in the monofunctional alkyl methacrylates, the monofunctional ether group-containing methacrylates and the monofunctional carboxyl-containing methacrylates, include dimethylaminomethyl methacrylate, N,N-dimethylaminoethyl methacrylate, N,N-dimethylaminopropyl methacrylate, morpholinoethyl methacrylate, trimethylsiloxyethyl methacrylate, diphenyl-2-methacryloyloxyethyl phosphate, 2-methacryloyloxyethyl acid phosphate, caprolactone-modified 2-methacryloyloxyethyl acid phosphate, etc.

Specific examples of the bifunctional methacrylates include 1,4-butandiol dimethacrylate, 1,6-hexanediol dimethacrylate, ethylene glycol dimethacrylate, diethylene glycol dimethacrylate, triethylene glycol dimethacrylate, tetraethylene glycol dimethacrylate, polyethylene glycol #200 dimethacrylate, polyethylene glycol #300 dimethacrylate, polyethylene glycol #400 dimethacrylate, polyethylene glycol #600 dimethacrylate, dipropylene glycol dimethacrylate, tripropylene glycol dimethacrylate, tetrapropylene glycol dimethacrylate, polypropylene glycol #400 dimethacrylate, polypropylene glycol #700 dimethacrylate, neopentyl glycol dimethacrylate, neopentyl glycol PO-modified dimethacrylate, hydroxypivalic acid neopentyl glycol ester dimethacrylate, caprolactone adduct dimethacrylate of hydroxypivalic acid neopentyl glycol ester, 1,6-hexanediol bis(2-hydroxy-3-methacryloyloxypropyl) ether, 1,9-nonanediol dimethacrylate, pentaerythritol dimethacrylate, pentaerythritol dimethacrylate monostearate, pentaerythritol dimethacrylate monobenzoate, 2,2-bis(4-methacryloxypolyethoxyphenyl)propane, bisphenol A dimethacrylate, EO-modified bisphenol A dimethacrylate, PO-modified bisphenol A dimethacrylate, hydrogenated bisphenol A dimethacrylate, EO-modified hydrogenated bisphenol A dimethacrylate, PO-modified hydrogenated bisphenol A dimethacrylate, bisphenol F dimethacrylate, EO-modified bisphenol F dimethacrylate, PO-modified bisphenol F dimethacrylate, EO-modified tetrabromobisphenol A dimethacrylate, tricyclodecanedimethylol dimethacrylate, isocyanuric acid EO-modified dimethacrylate, etc.

Specific examples of the tri or more functional methacrylates include glycerin PO-modified trimethacrylate, trimethylolethane trimethacrylate, trimethylolpropane trimethacrylate, trimethylolpropane EO-modified trimethacrylate, trimethylolpropane PO-modified trimethacrylate, isocyanuric acid EO-modified trimethacrylate, isocyanuric acid EO-modified ε-caprolactone-modified trimethacrylate, 1,3,5-trimethacryloylhexahydro-s-trizine, pentaerythritol trimethacrylate, dipentaerythritol trimethacrylate tripropionate, pentaerythritol tetramethacrylate, dipentaerythritol pentamethacrylate monopropionate, dipentaerythritol hexamethacrylate, tetramethylolmethane tetramethacrylate, oligo ester tetramethacrylate, tris(methacryloyloxy) phosphate, etc.

In the case where the methacrylate is an oligomer or a polymer, it is preferable to set weight average molecular weight, at 100 to 30,000, and more preferably at 200 to 20,000, in view of heat resistance, coating properties, solubility to an organic solvent, solubility to a developing solution of the radical reactive composition of the present invention, etc. When the weight average molecular weight is below 100, strength of a cured film or a molded article obtained from the radical reactive composition of the present invention is likely to be insufficient. On the other hand, when the weight average molecular weight is over 30,000, not only viscosity of the methacrylate itself increases, which deteriorates solubility, but also it is likely to be difficult to obtain a cured film having uniform surface and constant film thickness of the cured film. It should be noted that weight average molecular weight is a value measured by gel permeation chromatography and then converted to standard polystyrene.

The allylates may be any of a monomer, an oligomer or a polymer, and specifically include, for example, allyl glycidyl ether, diallyl phthalate, triallyl trimellitate, triallyl isocyanurate, etc. Such an allylate may be halogenated or hydrogenated. In addition, as such an allylate, a derivative of the above-described specific examples is also included. It should be noted that, as such an acrylate, one kind of the acrylate may be used alone, or two or more kinds of the acrylates may be used in combination. In addition, as such an acrylate, a commercially available one, or the one synthesized as appropriate by a method known per se may be used.

In the case where the allylate is an oligomer or a polymer, it is preferable to set weight average molecular weight, at 100 to 30,000, and more preferably at 200 to 20,000, in view of heat resistance, coating properties, solubility to an organic solvent, solubility to a developing solution of the radical reactive composition of the present invention, etc. When the weight average molecular weight is below 100, strength of a cured film or a molded article obtained from the radical reactive composition of the present invention is likely to be insufficient. On the other hand, when the weight average molecular weight is over 30,000, not only viscosity of the allylate itself increases, which deteriorates solubility, but also it is likely to be difficult to obtain a cured film having uniform surface and constant film thickness of the cured film. It should be noted that weight average molecular weight is a value measured by gel permeation chromatography and then converted to standard polystyrene.

The acid amides may be any of a monomer, an oligomer or a polymer, and specifically include, for example, acrylamide, N-methylolacrylamide, diacetone acrylamide, N,N-dimethylacrylamide, N,N-diethylacrylamide, N-isopropylacrylamide, acryloylmorpholine, methacrylamide, N-methylolmethacrylamide, diacetone methacrylamide, N,N-dimethylmethacrylamide, N,N-diethylmethacrylamide, N-isopropylmethacrylamide, methacryloylmorpholine, etc. Such an acid amide may be halogenated or hydrogenated. In addition, as such an acid amide, a derivative of the above-described specific examples is also included. It should be noted that, as such an acid amide, one kind of the acid amide may be used alone, or two or more kinds of the acid amides may be used in combination. In addition, as such an acid amide, a commercially available one, or the one synthesized as appropriate by a method known per se may be used.

In the case where the acid amide is an oligomer or a polymer, it is preferable to set weight average molecular weight, at 100 to 30,000, and more preferably at 200 to 20,000, in view of heat resistance, coating properties, solubility to an organic solvent, solubility to a developing solution of the radical reactive composition of the present invention, etc. When the weight average molecular weight is below 100, strength of a cured film or a molded article obtained from the radical reactive composition of the present invention is likely to be insufficient. On the other hand, when the weight average molecular weight is over 30,000, not only viscosity of the acid amide itself increases, which deteriorates solubility, but also it is likely to be difficult to obtain a cured film having uniform surface and constant film thickness of the cured film. It should be noted that weight average molecular weight is a value measured by gel permeation chromatography and then converted to standard polystyrene.

The styrenes may be any of a monomer, an oligomer or a polymer, and specifically include, for example, styrene, p-methylstyrene, p-methoxystyrene, p-tert-butoxystyrene, p-tert-butoxycarbonylstyrene, p-tert-butoxycarbonyloxystyrene, 2,4-diphenyl-4-methyl-1-pentene, etc. Such styrenes may be halogenated or hydrogenated. In addition, as such styrenes, a derivative of the above-described specific examples is also included. It should be noted that, as such styrenes, one kind of the styrenes may be used alone, or two or more kinds of the styrenes may be used in combination. In addition, as such styrenes, a commercially available one, or the one synthesized as appropriate by a method known per se may be used.

In the case where the styrenes are an oligomer or a polymer, it is preferable to set weight average molecular weight, at 100 to 30,000, and more preferably at 200 to 20,000, in view of heat resistance, coating properties, solubility to an organic solvent, solubility to a developing solution of the radical reactive composition of the present invention, etc. When the weight average molecular weight is below 100, strength of a cured film or a molded article obtained from the radical reactive composition of the present invention is likely to be insufficient. On the other hand, when the weight average molecular weight is over 30,000, not only viscosity of the styrenes themselves increases, which deteriorates solubility, but also it is likely to be difficult to obtain a cured film having uniform surface and constant film thickness of the cured film. It should be noted that weight average molecular weight is a value measured by gel permeation chromatography and then converted to standard polystyrene.

Specific examples of other vinyl compound not included in the unsaturated carboxylic acid, the acid amide and styrenes, include vinyl acetate, vinyl monochloroacetate, vinyl benzoate, vinyl pivalate, vinyl butyrate, vinyl laurate, divinyl adipate, vinyl methacrylate, vinyl crotonate, vinyl 2-ethylhexanoate, N-vinylcarbazole, N-vinylpyrrolidone, etc.

In the case where the vinyl compound is an oligomer or a polymer, it is preferable to set weight average molecular weight, at 100 to 30,000, and more preferably at 200 to 20,000, in view of heat resistance, coating properties, solubility to an organic solvent, solubility to a developing solution of the radical reactive composition of the present invention, etc. When the weight average molecular weight is below 100, strength of a cured film or a molded article obtained from the radical reactive composition of the present invention is likely to be insufficient. On the other hand, when the weight average molecular weight is over 30,000, not only viscosity of the vinyl compound itself increases, which deteriorates solubility, but also it is likely to be difficult to obtain a cured film having uniform surface and constant film thickness of the cured film. It should be noted that weight average molecular weight is a value measured by gel permeation chromatography and then converted to standard polystyrene.

A contained amount of the radical generator of the present invention, contained in the radical reactive composition of the present invention, is not especially limited, as long as it is an amount generally used in this field usually, and is usually 0.1 to 100% by weight, preferably 1 to 50% by weight, and more preferably 5 to 30% by weight, for example, relative to weight of the radical-reactive compound. When the contained amount of the radical generator of the present invention is extremely small, curing of the radical reactive composition is likely to be insufficient. On the other hand, when the contained amount of the radical generator of the present invention is very large, a problem of impairing economic performance, etc. occurs.

In the case of using the radical reactive composition of the present invention as a photosensitive resin composition, a sensitizer may be added thereto to enhance sensitivity, by enlarging a photosensitive wavelength region. The sensitizer is not especially limited, as long as it is a sensitizer generally used in this field usually. Specific examples of the sensitizer include the same as specific examples of the sensitizer to be used in the above-described base-reactive composition of the present invention. As such a sensitizer, one kind of the sensitizer may be used alone, or two or more kinds of the sensitizers may be used in combination. It should be noted that, as such a sensitizer, a commercially available one, or the one synthesized as appropriate by a method known per se may be used A contained amount of the sensitizer contained, as needed, in the radical reactive composition of the present invention, is not especially limited, as long as it is an amount generally used in this field usually, and may be determined as appropriate, by the radical generator or the radical-reactive compound to be used, and sensitivity required, etc. In more specifically, in the case where the sensitizer is contained, the contained amount of the sensitizer is preferably 1 to 30% by mass, and among them, 1 to 20% by weight is more preferable, relative to the whole radical reactive composition. When the contained amount of the sensitizer is less than 1% by mass, there is the case where sensitivity cannot be enhanced sufficiently. On the other hand, when the contained amount of the sensitizer is over 30% by mass, there is the case where it is excessive to enhance sensitivity.

In the case of coating the radical reactive composition of the present invention onto a predetermined substrate, there is the case where the composition containing an organic solvent is desirable. By containing the organic solvent into the radical reactive composition, coating properties can be enhanced, thus leading to good workability. The organic solvent is not especially limited, as long as it is an organic solvent generally used in this field usually. Specific examples of the organic solvent include the same as specific examples of the organic solvent to be used in the above-described base-reactive composition of the present invention. It should be noted that, as such an organic solvent, one kind of the organic solvent may be used alone, or two or more kinds of the organic solvents may be used in combination. In addition, as such an organic solvent, a commercially available one may be used.

A contained amount of the organic solvent contained, as needed, in the radical reactive composition of the present invention, is not especially limited, as long as it is an amount generally used in this field usually, and may be selected as appropriate so as to attain uniform coating, for example, in coating the radical reactive composition onto a predetermined substrate, and forming a layer made of the radical reactive composition, and it is usually 0.01 to 50 mL, preferably 0.05 to 30 mL, and more preferably 0.1 to 10 mL, for example, relative to 1 g of the radical-reactive compound.

The radical reactive composition of the present invention, other than the above-described additive, may contain an additive, such as, for example, a pigment; a dye; a thermal-polymerization inhibitor, such as p-methoxyphenol, hydroquinone, alkyl substituted hydroquinone, catechol, tert-butylcatechol, phenothiazine; a curing accelerator or a chain transfer catalyst, such as amines, such as N-phenylglycine, triethanol amine, N,N-diethylaniline, thiols, disulfides, thiones, O-acylthiohydroxamate, N-alkyloxypyridinethiones; an oxygen removing agent or a reducing agent, such as phosphine, phosphonate, phosphite; an anti-fogging agent; an anti-fading agent; an anti-halation agent; a fluorescent brightening agent; a surfactant; a coloring agent; an extender; a plasticizer; a flame retardant; an antioxidant; an ultraviolet absorbing agent; a foaming agent; a fungicide; an anti-static agent; a magnetic substance or an additive which give other various characteristics; a diluent solvent, etc., in an range not interfering the purpose and effect of the present invention. As such an additive, one kind of the additive may be used alone, or two or more kinds of the additives may be used in combination. It should be noted that, as such an additive, a commercially available one, or the one synthesized as appropriate by a method known per se may be used.

A pattern formation using the radical reactive composition of the present invention is carried out, for example, as follows. A coating solution is prepared, for example, by dissolving the composition into an organic solvent, coating thus prepared coating solution to an appropriate solid surface, such as a substrate, and drying to form the coated film. Then a polymerization reaction of the radical-reactive compound contained in the radical reactive composition may be promoted by generating the radical by carrying out pattern exposure to the coated film thus formed.

As for a coating method of the radical reactive composition of the present invention onto a substrate, an irradiation method of active energy ray, a development method, etc., to be carried out in the above-described pattern formation, a method known per se may be adopted as appropriate.

The radical reactive composition of the present invention as explained above, by containing the radical generator of the present invention and the radical-reactive compound, can be made a composition in which a polymerization reaction of the radical-reactive compound proceeds, using a radical generated from the radical generator by operation, such as irradiation of active energy ray or heating, as an initiator, and curing of the radical-reactive compound is carried out effectively. The radical reactive composition of the present invention, which exerts such effect, can be used suitably, for example, for a curing material or a resist material (pattern formation material), etc.

In the case when the radical reactive composition of the present invention was used for a curing material, a molded article to be formed after curing operation is widely used, as members, etc. of a field that characteristics, such as heat resistance, dimensional stability, insulation properties, are considered to be effective, for example, constitutional members of a paint, a printing ink, a color filter, a film for a flexible display, a semiconductor apparatus, electronics parts, an interlayer insulating film, a wiring covering film, an optical circuit, optical circuit parts, an antireflection film, a hologram, optical members or a construction material, and thus a printed matter, a color filter, a film for a flexible display, a semiconductor apparatus, electronics parts, an interlayer insulating film, a wiring covering film, an optical circuit, optical circuit parts, an antireflection film, a hologram, optical parts or a construction material, etc., are provided. In addition, in the case where the radical reactive composition of the present invention was used for a resist material (patter forming material), the pattern, etc., to be formed after a pattern formation operation is provided with heat resistance and insulation properties, and can be used effectively as, for example, a color filter, a film for a flexible display, electronics parts, a semiconductor apparatus, an interlayer insulating film, a wiring covering film, an optical circuit, optical circuit parts, an antireflection film, other optical parts or electronics parts.

—Compounds Represented by the General Formulae ($C_1$) and ($C_2$) of the Present Invention—

The compounds of the present invention are compounds represented by the following general formulae ($C_1$) and ($C_2$).

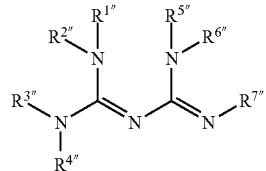

($C_1$)

(wherein $R^{1''}$ to $R^{4''}$ each independently represent an alkyl group having 1 to 8 carbon atoms, $R^{5''}$ represents an alkyl group having 2 to 8 carbon atoms, $R^{6''}$ represents an alkyl group having 1 to 6 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group; an alkenyl group having 2 to 6 carbon atoms; or an arylalkyl group having 7 to 15 carbon atoms which may have a substituent selected from the group consisting of an alkyl group having 1 to 6 carbon atoms, an alkoxy group having 1 to 6 carbon atoms, a halogen atom and a nitro group, and $R^{7''}$ represents an alkyl group having 2 to 8 carbon atoms which may have an amino group.)

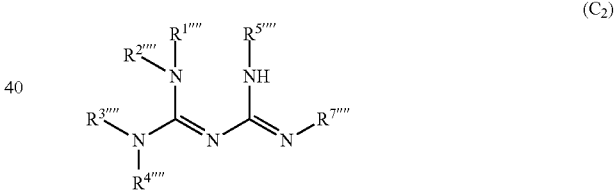

($C_2$)

(wherein $R^{1''''}$ to $R^{4''''}$ each independently represent an alkyl group having 1 to 8 carbon atoms, $R^{5''''}$ represents an alkyl group having 1 to 10 carbon atoms; or an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group, and $R^{7''''}$ represents an aryl group having 6 to 14 carbon atoms which may have a substituent selected from the group consisting of an alkyl group having 1 to 6 carbon atoms, an alkoxy group having 1 to 6 carbon atoms, a halogen atom and a nitro group.)

Specific examples of the alkyl group having 1 to 8 carbon atoms represented by $R^{1''}$ to $R^{4''}$ in the general formula ($C_1$), include those similar to specific examples of the alkyl group having 1 to 8 carbon atoms represented by $R^{1'}$ to $R^{4'}$ in the general formula (A'), and also specific examples of the preferable alkyl group and the more preferable alkyl group include the same.

Specific examples of the alkyl group having 2 to 8 carbon atoms represented by $R^{5''}$ in the general formula ($C_1$), include those similar to specific examples of the alkyl group having 2 to 8 carbon atoms, which is included as a preferable alkyl group represented by $R^{5'}$ in the general formula (A'), and also more preferable specific examples include the same.

Specific examples of "an alkyl group having 1 to 6 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group" represented by $R^{6''}$ in the general formula ($C_1$) include those similar to specific examples of "an alkyl group having 1 to 6 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group" represented by $R^{6'}$ in the general formula (A'), and also preferable specific examples include the same.

Specific examples of the alkenyl group having 2 to 6 carbon atoms represented by $R^{6''}$ in the general formula ($C_1$), include those similar to specific examples of the alkenyl group having 2 to 6 carbon atoms represented by $R^{6'}$ in the general formula (A'), and also preferable specific examples include the same.

Specific examples of "an arylalkyl group having 7 to 15 carbon atoms, which may have a substituent selected from the group consisting of an alkyl group having 1 to 6 carbon atoms, an alkoxy group having 1 to 6 carbon atoms, halogen atom and a nitro group" represented by $R^{6''}$ in the general formula ($C_1$), include those similar to specific examples of "an arylalkyl group having 7 to 15 carbon atoms, which may have a substituent selected from the group consisting of an alkyl group having 1 to 6 carbon atoms, an alkoxy group having 1 to 6 carbon atoms, halogen atom and a nitro group" represented by $R^{6'}$ in the general formula (A'), and also preferable specific examples include the same.

Specific examples of "an alkyl group having 2 to 8 carbon atoms which may have an amino group" represented by $R^{7''}$ in the general formula ($C_1$), include those similar to specific examples of "an alkyl group having 2 to 8 carbon atoms which may have an amino group", which is included as a preferable alkyl group represented by $R^{7'}$ in the general formula (A'), and also more preferable specific examples include the same.

A preferable specific example of the compound represented by the general formula ($C_1$) includes the compound represented by following formula (13).

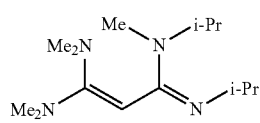

(13)

The compound represented by the formula (13) corresponds to a compound, in the compound represented by the general formula ($C_1$), where $R^{1''}$ to $R^{4''}$ are a methyl group, which is an alkyl group having one carbon atom, $R^{5''}$ to $R^{7''}$ are an isopropyl group, which is a branched alkyl group having 3 carbon atoms, $R^{6''}$ is a methyl group, which is an alkyl group having one carbon atom and not having a substituent.

Specific examples of the alkyl group having 1 to 8 carbon atoms represented by $R^{1''''}$ to $R^{4''''}$ in the general formula ($C_2$), include those similar to specific examples of the alkyl group having 1 to 8 carbon atoms represented by $R^{1'''}$ to $R^{4'''}$ in the general formula (A''), and also specific examples of the preferable alkyl group and the more preferable alkyl group include the same.

Specific examples of the alkyl group having 1 to 10 carbon atoms represented by $R^{5''''}$ in the general formula ($C_2$), include those similar to specific examples of the alkyl group having 1 to 10 carbon atoms represented by $R^{5'''}$ in the general formula (A''), and also specific examples of the preferable alkyl group and the more preferable alkyl group include the same.

Specific examples of the aryl group having 6 to 14 carbon atoms in "an aryl group having 6 to 14 carbon atoms which may have a substituent selected from the group consisting of an alkyl group having 1 to 6 carbon atoms, an alkoxy group having 1 to 6 carbon atoms, halogen atom and a nitro group" represented by $R^{5''''}$ and $R^{7''''}$ in the general formula ($C_2$), include those similar to specific examples of the aryl group having 6 to 14 carbon atoms in "an aryl group having 6 to 14 carbon atoms which may have a substituent selected from the group consisting of an alkyl group having 1 to 6 carbon atoms, an alkoxy group having 1 to 6 carbon atoms, halogen atom and a nitro group" represented by $R^1$ to $R^7$ in the general formula (A), and also specific examples of the preferable aryl group and the more preferable aryl group include the same.

Specific examples of the alkyl group having 1 to 6 carbon atoms in "an aryl group having 6 to 14 carbon atoms which may have a substituent selected from the group consisting of an alkyl group having 1 to 6 carbon atoms, an alkoxy group having 1 to 6 carbon atoms, halogen atom and a nitro group" represented by $R^{5''''}$ and $R^{7''''}$ in the general formula ($C_2$), include those similar to specific examples of the alkyl group having 1 to 6 carbon atoms in "an aryl group having 6 to 14 carbon atoms which may have a substituent selected from the group consisting of an alkyl group having 1 to 6 carbon atoms, an alkoxy group having 1 to 6 carbon atoms, halogen atom and a nitro group" represented by $R^1$ to $R^7$ in the general formula (A), and also specific examples of the preferable alkyl group include the same.

Specific examples of the alkoxy group having 1 to 6 carbon atoms in "an aryl group having 6 to 14 carbon atoms which may have a substituent selected from the group consisting of an alkyl group having 1 to 6 carbon atoms, an alkoxy group having 1 to 6 carbon atoms, halogen atom and a nitro group" represented by $R^{5''''}$ and $R^{7''''}$ in the general formula ($C_2$), include those similar to specific examples of the alkoxy group having 1 to 6 carbon atoms in "an aryl group having 6 to 14 carbon atoms which may have a substituent selected from the group consisting of an alkyl group having 1 to 6 carbon atoms, an alkoxy group having 1 to 6 carbon atoms, halogen atom and a nitro group" represented by $R^1$ to $R^7$ in the general formula (A), and also specific examples of the preferable alkoxy group include the same.

Specific examples of the halogen atom in "an aryl group having 6 to 14 carbon atoms which may have a substituent selected from the group consisting of an alkyl group having 1 to 6 carbon atoms, an alkoxy group having 1 to 6 carbon atoms, halogen atom and a nitro group" represented by $R^{5''''}$ and $R^{7''''}$ in the general formula ($C_2$), include those similar to specific examples of the halogen atom in "an aryl group having 6 to 14 carbon atoms which may have a substituent selected from the group consisting of an alkyl group having 1 to 6 carbon atoms, an alkoxy group having 1 to 6 carbon atoms, halogen atom and a nitro group" represented by $R^1$ to $R^7$ in the general formula (A), and also specific examples of the preferable halogen atom include the same.

The nitro group in "an aryl group having 6 to 14 carbon atoms which may have a substituent selected from the group consisting of an alkyl group having 1 to 6 carbon atoms, an alkoxy group having 1 to 6 carbon atoms, halogen atom and a nitro group" represented by $R^{5''''}$ and $R^{7''''}$ in the general formula ($C_2$), means a nitro group binding to carbon atom on the aryl group.

Among the substituent in "an aryl group having 6 to 14 carbon atoms which may have a substituent selected from the group consisting of an alkyl group having 1 to 6 carbon atoms, an alkoxy group having 1 to 6 carbon atoms, halogen atom and a nitro group" represented by $R^{5''''}$ and $R^{7''''}$ in the general formula ($C_2$), the alkyl group having 1 to 6 carbon atoms, and the alkoxy group having 1 to 6 carbon atoms are preferable.

Specific examples of "an aryl group having 6 to 14 carbon atoms which may have a substituent selected from the group consisting of an alkyl group having 1 to 6 carbon atoms, an alkoxy group having 1 to 6 carbon atoms, halogen atom and a nitro group" represented by $R^{5''''}$ and $R^{7''''}$ in the general formula ($C_2$), include those similar to specific examples of "an aryl group having 6 to 14 carbon atoms which may have a substituent selected from the group consisting of an alkyl group having 1 to 6 carbon atoms, an alkoxy group having 1 to 6 carbon atoms, halogen atom and a nitro group" represented by $R^{5'''}$ and $R^{7'''}$ in the general formula (A'').

Preferable specific examples of the compounds represented by the general formula ($C_2$) include the compounds represented by following formulae (14), (15), (16) and (17).

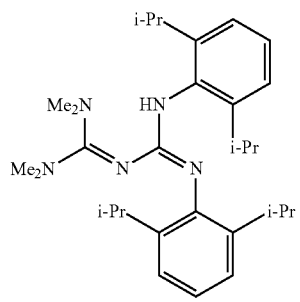
(14)

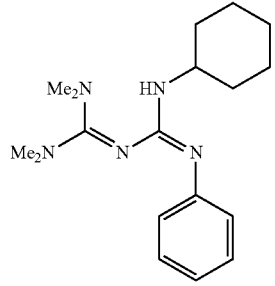 [SMILES: CN(C)C(=N/C(=N\c1ccccc1)NC1CCCCC1)N(C)C]
(15)

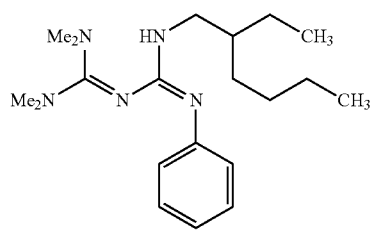 [SMILES: CCCCC(CC)CN/C(N=C(N(C)C)N(C)C)=N/c1ccccc1]
(16)

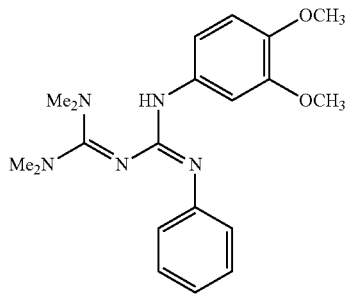 [SMILES: COc1ccc(N/C(N=C(N(C)C)N(C)C)=N/c2ccccc2)cc1OC]
(17)

The compounds represented by the general formulae ($C_1$) and ($C_2$) correspond to the base generating from the compound represented by the general formula (A) of the present invention, and these compounds indicate strong basicity, as well as have low nucleophilicity, and are thus the biguanide derivatives which are capable of functioning as a catalyst having freedom without being incorporated in a polymer (resin).

The compounds represented by such general formulae ($C_1$) and ($C_2$) are capable of providing the base generator, by forming salts with the carboxylic acids represented by the above-described general formulae ($B_1$—H), ($B_2$—H), ($B_3$—H) and ($B_4$—H), as well as with carboxylic acids shown below.

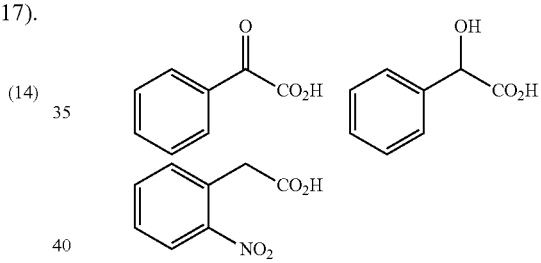

EXAMPLES

Explanation on the present invention will be given specifically below based on Examples and Comparative Examples, however, the present invention should not be limited to these Examples.

Synthetic Example 1: Synthesis of 1,2-diisopropyl-4,4,5,5-tetramethylbiguanide

Into 11.9 g of 1,1,3,3-tetramethylguanidine (10.3 mmol; produced by Wako Pure Chemical Industries, Ltd.), 13.1 g of N,N'-diisopropylcarbodiimide (10.3 mmol; produced by Wako Pure Chemical Industries, Ltd.) was added and heated under stirring at 100° C. for two hours. After completion of the reaction, hexane was added to the reaction solution, cooled to 5° C. and the solvent was removed from the resulting crystal to obtain 9.88 g of 1,2-diisopropyl-4,4,5,5-tetramethylbiguanide (white powder, yield: 39%). Measurement results of $^1$H-NMR, and a structural formula of 1,2-diisopropyl-4,4,5,5-tetramethylbiguanide are shown below.

$^1$H-NMR (400 MHz, CDCl$_3$) δ (ppm): 1.10 (12H, d), 2.78 (12H, s), 3.38 (2H, q).

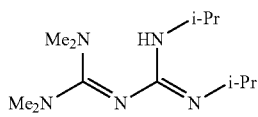

Example 1: Synthesis of 1,2-diisopropyl-1,4,4,5,5-pentamethylbiguanide 1.00 g of 1,2-diisopropyl-4,4,5,5-tetramethylbiguanide (4.1 mmol; produced by Wako Pure Chemical Industries, Ltd.), obtained in the Synthetic Example 1, and 0.3 g of 60% NaH (4.1 mmol; produced by Wako Pure Chemical Industries, Ltd.) were dissolved into 20 mL of anhydrous tetrahydrofuran (THF) and stirred at 50° C. for one hour. Next, after cooling the reaction solution to room temperature, 0.63 g of methyl iodide (4.5 mmol; produced by Wako Pure Chemical Industries, Ltd.) was added to the reaction solution and reacted at room temperature for one hour. After completion of the reaction, hexane was added to the reaction solution, and then it was filtrated by Celite and the resulting filtrate was concentrated under reduced pressure to obtain 0.82 g of 1,2-diisopropyl-1,4,4,5,5-pentamethylbiguanide (slight yellow oil, yield: 78%). Measurement results of $^1$H-NMR, and a structural formula of 1,2-diisopropyl-1,4,4,5,5-pentamethylbiguanide are shown below.

$^1$H-NMR (400 MHz, CDCl$_3$) δ (ppm): 1.04 (12H, d), 2.83 (15H, s), 3.03 (1H, brs), 4.45 (1H, brs).

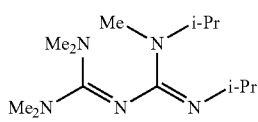

Synthetic Example 2: Synthesis of 1,2-dicyclohexyl-4,4,5,5-tetramethylbiguanide carbonate Into 12.2 g of 1,1,3,3-tetramethylguanidine (106 mmol; produced by Wako Pure Chemical Industries, Ltd.), 10.9 g of N,N'-dicyclohexylcarbodiimide (53 mmol; produced by Wako Pure Chemical Industries, Ltd.) was added and heated under stirring at 100° C. for two hours. After completion of the reaction, the reaction solution was concentrated under reduced pressure, to remove 1,1,3,3-tetramethylguanidine, and then 20 mL of acetone and 2 mL of water were added to the resulting residue and dry ice was charged and the resulting crystal was collected by filtration to obtain 8.44 g of 1,2-dicyclohexyl-4,4,5,5-tetramethylbiguanide carbonate (white powder, yield: 45%). Measurement results of $^1$H-NMR and $^{13}$C-NMR, and a structural formula of 1,2-dicyclohexyl-4,4,5,5-tetramethylbiguanide carbonate are shown below.

$^1$H-NMR (400 MHz, D$_2$O) δ (ppm): 1.22-1.80 (20H, brm), 2.86 (12H, s), 3.02 (2H, m).

$^{13}$C-NMR (400 MHz, CD$_3$OD) δ (ppm): 26.1, 34.1, 40.1, 52.4, 158.0, 161.2, 164.4.

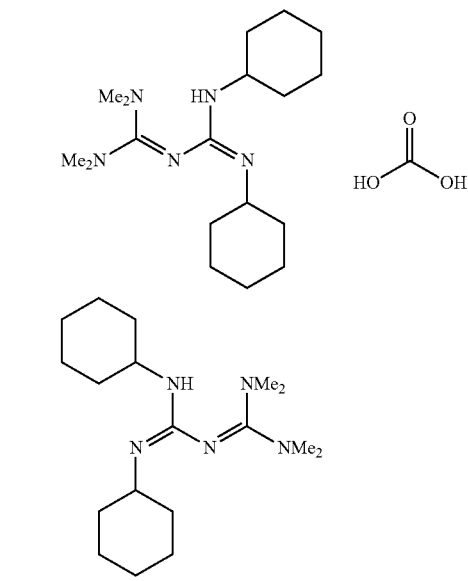

Example 2: Synthesis of 1,2-bis(2,6-diisopropylphenyl)-4,4,5,5-tetramethylbiguanide Into 3.18 g of 1,1,3,3-tetramethylguanidine (27.6 mmol; produced by Wako Pure Chemical Industries, Ltd.), 13.1 g of bis(2,6-diisopropylphenyl)carbodiimide (27.6 mmol; produced by Tokyo Chemical Industry Co., Ltd.) was added and stirred at 25° C. for 30 minutes. After completion of the reaction, hexane was added to the reaction solution, cooled to 5° C., and the solvent was removed from the resulting crystal to obtain 10.20 g of 1,2-bis(2,6-diisopropylphenyl)-4,4,5,5-tetramethylbiguanide (white powder, yield: 77%). Measurement results of $^1$H-NMR, and a structural formula of 1,2-bis(2,6-diisopropylphenyl)-4,4,5,5-tetramethylbiguanide are shown below.

$^1$H-NMR (400 MHz, CDCl$_3$) δ (ppm): 1.00-1.29 (24H, m), 2.81 (12H, s), 3.43 (4H, m), 7.07-7.26 (6H, m).

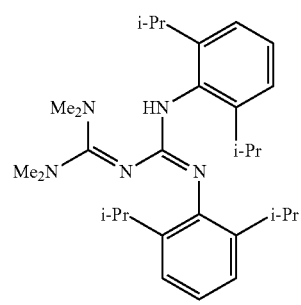

Synthetic Example 3: Synthesis of 1-cyclohexyl-3-phenylcarbodiimide

Into 10.0 g of phenyl isothiocyanate (74.0 mmol; produced by Wako Pure Chemical Industries, Ltd.), 20 mL of acetonitrile was added and cooled to 5° C., and then 7.34 g of cyclohexylamine (74.0 mmol; produced by Wako Pure Chemical Industries, Ltd.) was added and stirred at 5° C. for 30 minutes. After completion of the reaction, the crystal precipitated in the reaction solution was isolated by filtration, and 10.0 g (42.6 mmol) among the resulting crystal was suspended in acetone, to which 4.32 g of triethylamine (42.6 mmol; produced by Wako Pure Chemical Industries, Ltd.) and 5.96 g of iodine (42.6 mmol; produced by Wako Pure Chemical Industries, Ltd.) were added, and stirred at 25° C. for one hour. After completion of the reaction, the crystal precipitated in the reaction solution was removed by filtration, and the filtrate after filtration was concentrated, and the resulting residue was purified by silica gel column chromatography to obtain 1.32 g of 1-cyclohexyl-3-phenylcarbodiimide (slight yellow oil, yield: 13%). Measurement results of $^1$H-NMR, and a structural formula of 1-cyclohexyl-3-phenylcarbodiimide are shown below.

$^1$H-NMR (400 MHz, CDCl$_3$) δ (ppm): 1.27-1.55 (5H, m), 1.75-1.79 (2H, m), 1.99-2.02 (2H, m), 3.44-3.50 (1H, m), 7.01-7.25 (3H, m), 7.25-7.30 (2H, m).

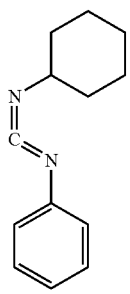

Example 3: Synthesis of 1-cyclohexyl-3-phenyl-4,4,5,5-tetramethylbiguanide

Into 1.32 g of 1,1,3,3-tetramethylguanidine (6.59 mmol; produced by Wako Pure Chemical Industries, Ltd.), 0.76 g of 1-cyclohexyl-3-phenylcarbodiimide (6.59 mmol) obtained in the Synthetic Example 3 and 20 mL of hexane, were added and stirred at 25° C. for 24 hours. After completion of the reaction, the crystal precipitated in the reaction solution was filtrated (isolated) by filtration, to obtain 1.82 g of 1-cyclohexyl-3-phenyl-4,4,5,5-tetramethylbiguanide (white powder, yield: 87%). Measurement results of $^1$H-NMR, and a structural formula of 1-cyclohexyl-3-phenyl-4,4,5,5-tetramethylbiguanide are shown below.

$^1$H-NMR (400 MHz, CDCl$_3$) δ (ppm): 1.12-1.19 (3H, m), 1.34-1.43 (2H, m), 1.57-1.71 (3H, m), 2.08-2.11 (2H, m), 2.49 (12H, s), 3.71-3.73 (1H, m), 6.74 (1H, t), 7.80 (2H, d).

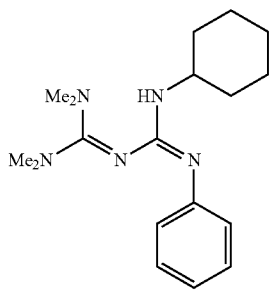

Synthetic Example 4: Synthesis of 1-(2-ethyl)hexyl-3-phenylcarbodiimide

Into 5.4 g of phenyl isothiocyanate (40.2 mmol; produced by Wako Pure Chemical Industries, Ltd.), 10 mL of acetonitrile was added and cooled to 5° C., and then 5.20 g of 2-ethylhexylamine (40.2 mmol; produced by Wako Pure Chemical Industries, Ltd.) was added and stirred at 5° C. for two hours. After completion of the reaction, the reaction solution was concentrated, and then the resulting residue was dissolved into acetone, and 4.07 g of triethylamine (40.2 mmol; produced by Wako Pure Chemical Industries, Ltd.) and 5.11 g of iodine (40.2 mmol; produced by Wako Pure Chemical Industries, Ltd.) were added, and stirred at 5° C. for two hours. After completion of the reaction, the crystal precipitated in the reaction solution was removed by filtration, and the filtrate after filtration was concentrated, and the resulting residue was purified by silica gel column chromatography to obtain 1.00 g of 1-(2-ethyl)hexyl-3-phenylcarbodiimide (slight yellow oil, yield: 10%). Measurement results of $^1$H-NMR, and a structural formula of 1-(2-ethyl)hexyl-3-phenylcarbodiimide are shown below.

$^1$H-NMR (400 MHz, CDCl$_3$) δ (ppm): 0.87-0.93 (6H, m), 1.25-3.40 (9H, m), 3.40 (2H, d), 7.06-7.11 (3H, m), 7.27 (2H, t).

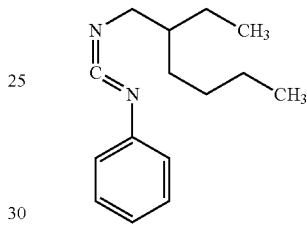

Example 4: Synthesis of 1-(2-ethyl)hexyl-3-phenyl-4,4,5,5-tetramethylbiguanide Into 0.50 g of 1,1,3,3-tetramethylguanidine (4.34 mmol; produced by Wako Pure Chemical Industries, Ltd.), 1.00 g of 1-(2-ethyl)hexyl-3-phenylcarbodiimide (4.34 mmol) obtained in the Synthetic Example 4 and 20 mL of hexane, were added and stirred at 25° C. for 24 hours. After completion of the reaction, reaction solution was concentrated to obtain 1.42 g of 1-(2-ethyl)hexyl-3-phenyl-4,4,5,5-tetramethylbiguanide (yellow oil, yield: 95%). Measurement results of $^1$H-NMR, and a structural formula of 1-(2-ethyl)hexyl-3-phenyl-4,4,5,5-tetramethylbiguanide are shown below.

$^1$H-NMR (400 MHz, CDCl$_3$) δ (ppm): 0.83-0.92 (6H, m), 1.30-1.40 (9H, m), 2.50 (12H, s), 3.26 (2H, d), 6.75 (1H, t), 6.80 (2H, d), 7.11 (2H, t).

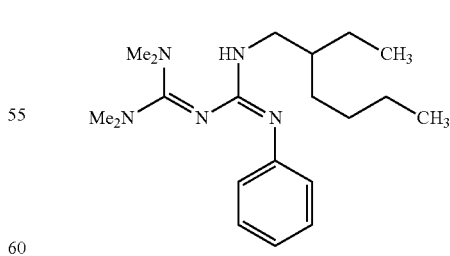

Synthetic Example 5: Synthesis of 1-(3,4-dimethoxyphenyl)-3-phenylcarbodiimide Into 10.0 g of phenyl isothiocyanate (74.0 mmol; produced by Wako Pure Chemical Industries, Ltd.), 30 mL of acetonitrile was added and cooled to 5° C., and then the 11.3 g of 3,4-dimethoxyaniline (74.0 mmol; produced by Wako Pure Chemical Industries, Ltd.) was added and stirred at 5° C. for two hours. After completion of the reaction, the crystal precipitated in the reaction solution was isolated by filtration, and 5.0 g (17.3 mmol) among the resulting crystal was suspended in ethyl acetate, to which 3.50 g of triethylamine (34.6 mmol; produced by Wako Pure Chemical Industries, Ltd.) and 2.41 g of iodine (19.0 mmol; produced by Wako Pure Chemical Industries, Ltd.) were added, and stirred at 25° C. for one hour. After completion of the reaction, the crystal precipitated in the reaction solution was removed by filtration, and the filtrate after filtration was concentrated, and the resulting residue was purified by silica gel column chromatography to obtain 0.98 g of 1-(3,4-dimethoxyphenyl)-3-phenylcarbodiimide (slight yellow oil, yield: 20%). Measurement results of $^1$H-NMR, and a structural formula of 1-(3,4-dimethoxyphenyl)-3-phenylcarbodiimide are shown below.

$^1$H-NMR (400 MHz, CDCl$_3$) δ (ppm): 3.87 (6H, s), 6.70 (1H, s), 6.75 (2H, q), 7.18 (3H, m), 7.34 (2H, t).

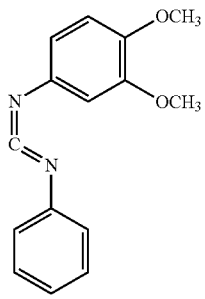

Example 5: Synthesis of 1-(3,4-dimethoxyphenyl)-3-pheny-4,4,5,5-tetramethylbiguanide Into 0.98 g of 1,1,3,3-tetramethylguanidine (3.85 mmol; produced by Wako Pure Chemical Industries, Ltd.), 0.98 g of 1-(3,4-dimethoxyphenyl)-3-phenylcarbodiimide (3.85 mmol) obtained in the Synthetic Example 5 and 20 mL of toluene, were added and stirred at 25° C. for 24 hours. After completion of the reaction, reaction solution was concentrated to obtain 1.42 g of 1-(3,4-dimethoxyphenyl)-3-pheny-4,4,5,5-tetramethylbiguanide (yellow amorphous, yield: 95%). Measurement results of $^1$H-NMR, and a structural formula of 1-(3,4-dimethoxyphenyl)-3-pheny-4,4,5,5-tetramethylbiguanide are shown below.

$^1$H-NMR (400 MHz, CDCl$_3$) δ (ppm): 2.55 (12H, s), 3.82 (3H, s), 3.84 (3H, s), 6.73 (1H, s), 6.90 (1H, t), 7.17-7.28 (6H, t).

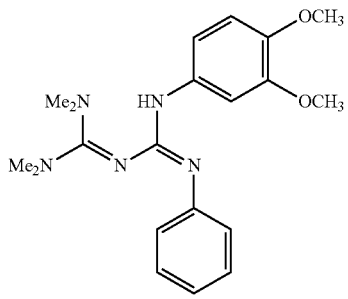

Example 6: Synthesis of 1,2-diisopropyl-4,4,5,5-tetramethylbiguanidium 2-(3-benzoylphenyl)propionate (Compound Represented by the Formula (1))

7.62 g of ketoprofen (30.0 mmol; produced by Hamari Chemicals, Ltd.) and 7.24 g of 1,2-diisopropyl-4,4,5,5-tetramethylbiguanide (30.0 mmol) obtained in the Synthetic Example 1, were dissolved into 30 mL of acetone, and stirred at room temperature for 10 minutes. After completion of the reaction, reaction solution was concentrated under reduced pressure, and the resulting residue was washed with hexane, and then dried under reduced pressure to obtain 14.86 g of 1,2-diisopropyl-4,4,5,5-tetramethylbiguanidium 2-(3-benzoylphenyl)propionate (white wax-like solid, yield: 100%). Measurement results of $^1$H-NMR, and a structural formula of 1,2-diisopropyl-4,4,5,5-tetramethylbiguanidium 2-(3-benzoylphenyl)propionate are shown below.

$^1$H-NMR (400 MHz, CDCl$_3$) δ (ppm): 1.10 (12H, d), 1.53 (3H, d), 2.82 (12H, s), 3.26 (2H, q), 3.70 (1H, t), 7.35 (1H, t), 7.44 (1H, t), 7.52-7.60 (2H, m), 7.74 (1H, d), 7.80 (1H, d), 7.89 (1H, s), 9.97 (1H, brs).

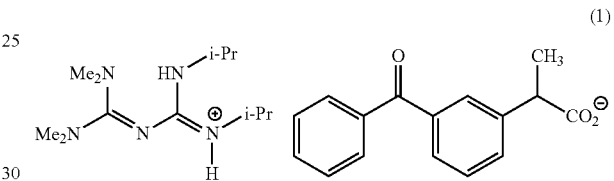

(1)

Example 7: Synthesis of 1,2-diisopropyl-1-methyl-4,4,5,5-tetramethylbiguanidium 2-(3-benzoylphenyl)propionate (Compound Represented by the Formula (2))

0.81 g of ketoprofen (3.2 mmol; produced by Hamari Chemicals, Ltd.) and 0.82 g of 1,2-diisopropyl-1,4,4,5,5-pentamethylbiguanide (3.2 mmol) obtained in the Example 1, were dissolved into 30 mL of acetone, and stirred at room temperature for 10 minutes. After completion of the reaction, reaction solution was concentrated under reduced pressure, and the resulting residue was washed with hexane, and then dried under reduced pressure to obtain 1.63 g of 1,2-diisopropyl-1-methyl-4,4,5,5-tetramethylbiguanidium 2-(3-benzoylphenyl)propionate (slight yellow oil, yield: 100%). Measurement results of $^1$H-NMR, and a structural formula of 1,2-diisopropyl-1-methyl-4,4,5,5-tetramethylbiguanidium 2-(3-benzoylphenyl)propionate are shown below.

$^1$H-NMR (400 MHz, CDCl$_3$) δ (ppm): 1.06 (6H, d), 1.40 (6H, d), 1.51 (3H, d), 1.98 (1H, brm), 2.90 (12H, s), 3.10 (3H, s), 3.12 (1H, brm), 3.67 (1H, q), 7.34 (1H, t), 7.46 (2H, t), 7.52-7.58 (2H, m), 7.73 (1H, d), 7.79 (2H, s), 7.85 (1H, s).

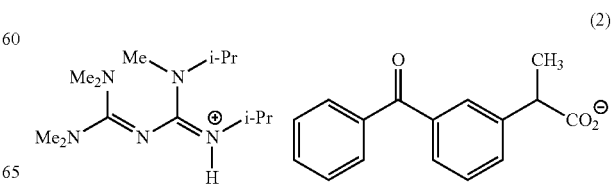

(2)

Example 8: Synthesis of 1,2-dicyclohexyl-4,4,5,5-tetramethylbiguanidium 2-(3-benzoylphenyl)propionate (Compound Represented by the Formula (3))

1.39 g of ketoprofen (5.5 mmol; produced by Hamari Chemicals, Ltd.) and 1.90 g of 1,2-dicyclohexyl-4,4,5,5-tetramethylbiguanide carbonate (2.7 mmol) obtained in the Synthetic Example 2, were dissolved into 30 mL of methanol, and stirred at room temperature for 10 minutes. After completion of the reaction, reaction solution was concentrated under reduced pressure, and the resulting residue was washed with hexane, and then dried under reduced pressure to obtain 3.16 g of 1,2-dicyclohexyl-4,4,5,5-tetramethylbiguanidium 2-(3-benzoylphenyl)propionate (colorless viscous oily-substance, yield: 100%). Measurement results of $^1$H-NMR, and a structural formula of 1,2-dicyclohexyl-4,4,5,5-tetramethylbiguanidium 2-(3-benzoylphenyl)propionate are shown below.

$^1$H-NMR (400 MHz, CDCl$_3$) δ (ppm): 1.08-1.12 (6H, brm), 1.28-1.31 (4H, brm), 1.50-1.52 (2H, brm), 1.52 (3H, d), 1.66-1.68 (8H, brm), 2.08 (2H, brs), 2.81 (12H, s), 3.72 (1H, q), 7.35 (1H, t), 7.44 (2H, t), 7.53-7.60 (2H, m), 7.72 (1H, d), 7.79 (2H, d), 7.85 (1H, s).

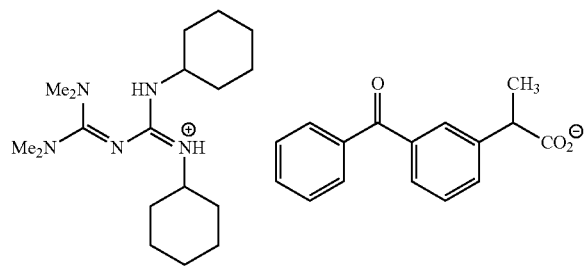

(3)

Example 9: Synthesis of 1,2-dicyclohexyl-4,4,5,5-tetramethylbiguanidium 2-(9-oxoxanthene-2-yl)propionate (Compound Represented by the Formula (4))

88 mg of 2-(9-oxoxanthene-2-yl)propionic acid (0.32 mmol; produced by Tokyo Chemical Industry Co., Ltd.) and 112 mg of 1,2-dicyclohexyl-4,4,5,5-tetramethylbiguanide carbonate (0.16 mmol) obtained in the Synthetic Example 2, were dissolved into 20 mL of methanol, and stirred at room temperature for 10 minutes. After completion of the reaction, reaction solution was concentrated under reduced pressure, and the resulting residue was washed with hexane, and then dried under reduced pressure to obtain 0.17 g of 1,2-dicyclohexyl-4,4,5,5-tetramethylbiguanidium 2-(9-oxoxanthene-2-yl)propionate (slight yellow amorphous, yield: 90%). Measurement results of $^1$H-NMR, and a structural formula of 1,2-dicyclohexyl-4,4,5,5-tetramethylbiguanidium 2-(9-oxoxanthene-2-yl)propionate are shown below.

$^1$H-NMR (400 MHz, CDCl$_3$) δ (ppm): 1.08-1.12 (6H, brm), 1.29-1.31 (4H, brm), 1.48-1.54 (2H, brm), 1.58 (3H, d), 1.66-1.68 (8H, brm), 2.08 (2H, brs), 2.87 (12H, s), 3.80 (1H, q), 7.35 (1H, t), 7.45 (1H, t), 7.47 (1H, d), 7.67 (1H, t), 7.98 (1H, dd), 8.34 (2H, m), 9.80 (1H, brs).

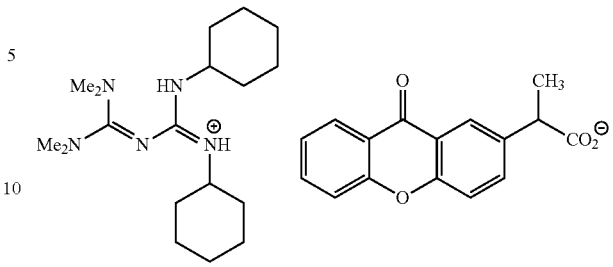

(4)

Example 10: Synthesis of 1,2-diisopropyl-4,4,5,5-tetramethylbiguanidium 8(7H)-ethylidene-4-methoxy-5,6-dihydronaphthalene-1-carboxylate (Compound Represented by the Formula (5))

0.23 g of 8(7H)-ethylidene-4-methoxy-5,6-dihydronaphthalene-1-carboxylic acid (1.0 mmol; produced by Wako Pure Chemical Industries, Ltd.) and 0.26 g of 1,2-diisopropyl-4,4,5,5-tetramethylbiguanide (1.0 mmol), were dissolved into 10 mL of acetone, and stirred at room temperature for 10 minutes. After completion of the reaction, reaction solution was concentrated under reduced pressure, and the resulting residue was washed with hexane, and then dried under reduced pressure to obtain 0.47 g of 1,2-diisopropyl-4,4,5,5-tetramethylbiguanidium 8(7H)-ethylidene-4-methoxy-5,6-dihydronaphthalene-1-carboxylate (white amorphous, yield: 100%). Measurement results of $^1$H-NMR, and a structural formula of 1,2-diisopropyl-4,4,5,5-tetramethylbiguanidium 8(7H)-ethylidene-4-methoxy-5,6-dihydronaphthalene-1-carboxylate are shown below.

$^1$H-NMR (400 MHz, CDCl$_3$) δ (ppm): 1.20 (12H, d), 1.69 (3H, d), 1.80 (2H, q), 2.47 (2H, t), 2.62 (2H, t), 2.91 (12H, s), 3.35 (2H, q), 3.76 (3H, s), 6.18 (1H, t), 6.61 (1H, d), 7.24 (1H, d).

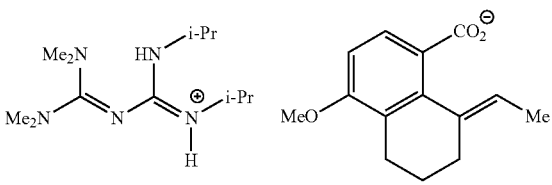

(5)

Example 11: Synthesis of 1,2-dicyclohexyl-4,4,5,5-tetramethylbiguanidium 8(7H)-ethylidene-4-methoxy-5,6-dihydronaphthalene-1-carboxylate (Compound Represented by the Formula (6))

1.16 g of 8(7H)-ethylidene-4-methoxy-5,6-dihydronaphthalene-1-carboxylic acid (5.0 mmol; produced by Wako Pure Chemical Industries, Ltd.) and 1.76 g of 1,2-dicyclohexyl-4,4,5,5-tetramethylbiguanide carbonate (2.5 mmol) obtained in the Synthetic Example 2, were dissolved into 10 mL of methanol, and stirred at room temperature for 10 minutes. After completion of the reaction, reaction solution was concentrated under reduced pressure, and the resulting residue was washed with hexane, and then dried under reduced pressure to obtain 2.56 g of 1,2-dicyclohexyl-4,4, 5,5-tetramethylbiguanidium 8(7H)-ethylidene-4-methoxy-5,6-dihydronaphthalene-1-carboxylate (white amorphous, yield: 92%). Measurement results of ¹H-NMR, and a structural formula of 1,2-dicyclohexyl-4,4,5,5-tetramethylbiguanidium 8(7H)-ethylidene-4-methoxy-5,6-dihydronaphthalene-1-carboxylate are shown below.

¹H-NMR (400 MHz, CDCl₃) δ (ppm): 1.22-1.80 (25H, brm), 2.48 (2H, t), 2.61 (2H, t), 2.92 (12H, s), 3.35 (2H, brm), 3.78 (3H, s), 6.18 (1H, t), 6.61 (1H, d), 7.24 (1H, d).

(6)

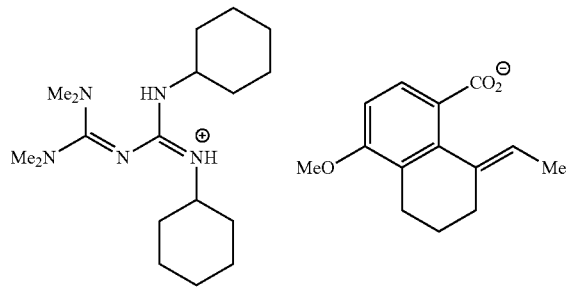

Example 12: Synthesis of 1,2-diisopropyl-4,4,5,5-tetramethylbiguanidium 2-(9-oxoxanthene-2-yl)propionate (Compound Represented by the Formula (7))

0.26 g of 2-(9-oxoxanthene-2-yl)propionic acid (10 mmol; produced by Tokyo Chemical Industry Co., Ltd.) and 0.24 g of 1,2-diisopropyl-4,4,5,5-tetramethylbiguanide (10 mmol) obtained in the Synthetic Example 1, were dissolved into 20 mL of acetone, and stirred at room temperature for 10 minutes. After completion of the reaction, reaction solution was concentrated under reduced pressure, and the resulting residue was washed with diisopropyl ether, and then dried under reduced pressure to obtain 0.44 g of 1,2-diisopropyl-4,4,5,5-tetramethylbiguanidium 2-(9-oxoxanthene-2-yl)propionate (slight yellow powder, yield: 88%). Measurement results of ¹H-NMR, and a structural formula of 1,2-diisopropyl-4,4,5,5-tetramethylbiguanidium 2-(9-oxoxanthene-2-yl)propionate are shown below.

¹H-NMR (400 MHz, CDCl₃) δ (ppm): 1.15 (12H, d), 1.58 (3H, d), 2.89 (12H, s), 3.31 (2H, m), 3.80 (1H, q), 7.35 (1H, t), 7.46 (1H, t), 7.47 (1H, d), 7.67 (1H, t), 7.97 (1H, dd), 8.32 (2H, m), 9.86 (1H, brs).

(7)

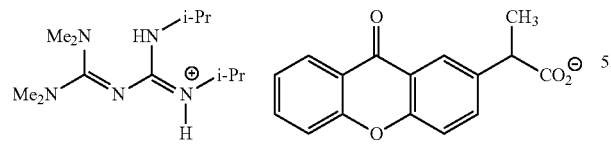

Example 13: Synthesis of 1,2-diisopropyl-4,4,5,5-tetramethylbiguanidium N-phthaloylglycine (Compound Represented by the Formula (8))

2.05 g of N-phthaloylglycine (10 mmol; produced by Wako Pure Chemical Industries, Ltd.) and 2.41 g of 1,2-diisopropyl-4,4,5,5-tetramethylbiguanide (10 mmol) obtained in the Synthetic Example 1, were dissolved into 20 mL of methanol, and stirred at room temperature for 10 minutes. After completion of the reaction, reaction solution was concentrated under reduced pressure, and the resulting residue was washed with acetone, and then dried under reduced pressure to obtain 3.42 g of 1,2-diisopropyl-4,4,5,5-tetramethylbiguanidium N-phthaloylglycine (white powder, yield: 76%). Measurement results of ¹H-NMR, and a structural formula of 1,2-diisopropyl-4,4,5,5-tetramethylbiguanidium N-phthaloylglycine are shown below.

¹H-NMR (400 MHz, CDCl₃) δ (ppm): 1.13 (12H, d), 2.85 (12H, s), 3.30 (2H, m), 4.30 (1H, s), 7.64 (2H, d), 7.82 (2H, d), 9.76 (1H, brs).

(8)

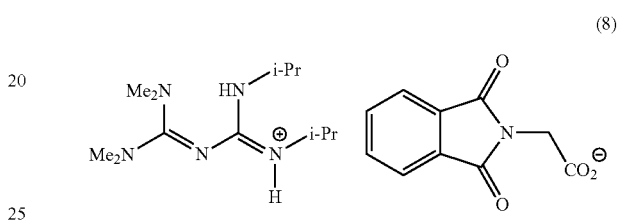

Example 14: Synthesis of 1,2-bis(2,6-diisopropylphenyl)-4,4,5,5-tetramethylbiguanidium 2-(3-benzoylphenyl)propionate (Compound Represented by the Formula (9))

0.63 g of ketoprofen (2.5 mmol; produced by Hamari Chemicals, Ltd.) and 1.19 g of 1,2-bis(2,6-diisopropylphenyl)-4,4,5,5-tetramethylbiguanide (2.5 mmol) obtained in the Example 2, were dissolved into 20 mL of methanol, and stirred at room temperature for 10 minutes. After completion of the reaction, reaction solution was concentrated under reduced pressure, and the resulting residue was washed with diisopropyl ether, and then dried under reduced pressure to obtain 1.84 g of 1,2-bis(2,6-diisopropylphenyl)-4,4,5,5-tetramethylbiguanidium 2-(3-benzoylphenyl)propionate (white powder, yield: 100%). Measurement results of ¹H-NMR, and a structural formula of 1,2-bis(2,6-diisopropylphenyl)-4,4,5,5-tetramethylbiguanidium 2-(3-benzoylphenyl)propionate are shown below.

¹H-NMR (400 MHz, CDCl₃) δ (ppm): 0.97-1.37 (23H, m), 2.47 (6H, s), 2.91 (6H, s), 3.18-3.47 (4H, m), 3.55 (1H, q), 7.09-7.30 (1H, t), 7.46 (1H, t), 7.47 (1H, d), 7.67 (1H, t), 7.97 (1H, dd), 8.32 (2H, m), 9.86 (1H, brs).

(9)

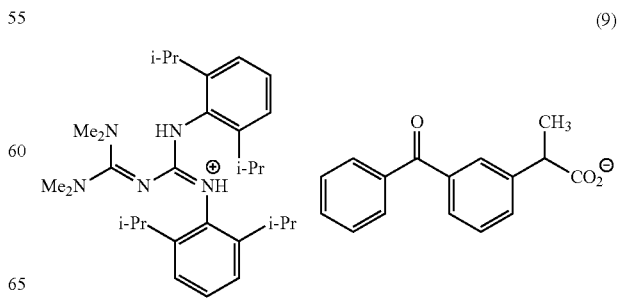

Example 15: Synthesis of 1-cyclohexyl-3-phenyl-4,4,5,5-tetramethylbiguanidium 2-(3-benzoylphenyl)propionate (Compound Represented by the Formula (10))

0.25 g of ketoprofen (1.0 mmol; produced by Hamari Chemicals, Ltd.) and 0.31 g of 1-cyclohexyl-3-phenyl-4,4,5,5-tetramethylbiguanide (1.0 mmol) obtained in the Example 3, were dissolved into 20 mL of acetone, and stirred at room temperature for 10 minutes. After completion of the reaction, reaction solution was concentrated under reduced pressure, and the resulting residue was washed with diisopropyl ether, and then dried under reduced pressure to obtain 0.55 g of 1-cyclohexyl-3-phenyl-4,4,5,5-tetramethylbiguanidium 2-(3-benzoylphenyl)propionate (white powder, yield: 100%). Measurement results of $^1$H-NMR, and a structural formula of 1-cyclohexyl-3-phenyl-4,4,5,5-tetramethylbiguanidium 2-(3-benzoylphenyl)propionate are shown below.

$^1$H-NMR (400 MHz, CDCl$_3$) δ (ppm): 1.21-1.24 (3H, m), 1.36 (2H, q), 1.51 (3H, d), 1.52-1.54 (1H, m), 1.72-1.85 (5H, m), 2.56 (12H, s), 3.40-3.58 (1H, m), 3.72 (1H, q), 6.97-7.01 (3H, m), 7.18 (2H, t), 7.32 (1H, t), 7.44 (1H, t), 7.42 (1H, t), 7.53-7.57 (2H, m), 7.71 (1H, d), 7.79 (1H, d), 7.88 (1H, s), 10.50 (1H, brs).

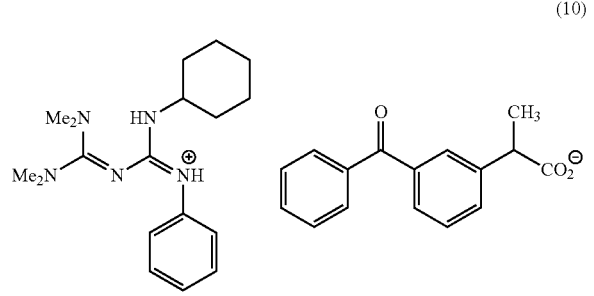

(10)

Example 16: Synthesis of 1-(2-ethyl)hexyl-3-phenyl-4,4,5,5-tetramethylbiguanidium 2-(3-benzoylphenyl)propionate (Compound Represented by the Formula (11))

0.29 g of ketoprofen (1.1 mmol; produced by Hamari Chemicals, Ltd.) and 0.40 g of 1-(2-ethyl)hexyl-3-phenyl-4,4,5,5-tetramethylbiguanide (1.1 mmol) obtained in the Example 4, were dissolved into 20 mL of acetone, and stirred at room temperature for 10 minutes. After completion of the reaction, reaction solution was concentrated under reduced pressure, and the resulting residue was washed with diisopropyl ether, and then dried under reduced pressure to obtain 0.68 g of 1-(2-ethyl)hexyl-3-phenyl-4,4,5,5-tetramethylbiguanidium 2-(3-benzoylphenyl)propionate (slight yellow oil, yield: 100%). Measurement results of $^1$H-NMR, and a structural formula of 1-(2-ethyl)hexyl-3-phenyl-4,4,5,5-tetramethylbiguanidium 2-(3-benzoylphenyl)propionate are shown below.

$^1$H-NMR (400 MHz, CDCl$_3$) δ (ppm): 0.81-0.88 (6H, m), 1.25-1.32 (8H, m), 1.50 (3H, d), 1.51-1.54 (1H, m), 2.57 (12H, s), 3.11-3.16 (2H, m), 3.71 (1H, q), 6.98-7.03 (3H, m), 7.18 (2H, t), 7.32 (1H, t), 7.43 (2H, t), 7.53 (1H, t), 7.59 (2H, d), 7.71 (1H, d), 7.78 (1H, d), 7.85 (1H, s), 10.80 (1H, brs).

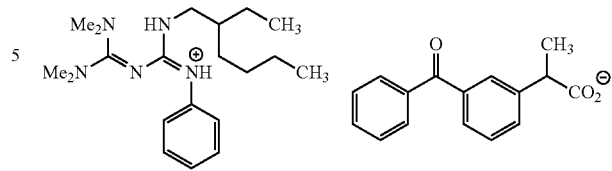

(11)

Example 17: Synthesis of 1-(3,4-dimethoxyphenyl)-3-phenyl-4,4,5,5-tetramethylbiguanidium 2-(3-benzoylphenyl)propionate (Compound Represented by the Formula (12))

0.25 g of ketoprofen (1.0 mmol; produced by Hamari Chemicals, Ltd.) and 0.36 g of 1-(3,4-dimethoxyphenyl)-3-pheny-4,4,5,5-tetramethylbiguanide (1.0 mmol) obtained in the Example 5, were dissolved into 20 mL of acetone, and stirred at room temperature for 10 minutes. After completion of the reaction, reaction solution was concentrated under reduced pressure, and the resulting residue was washed with diisopropyl ether, and then dried under reduced pressure to obtain 0.58 g of 1-(3,4-dimethoxyphenyl)-3-phenyl-4,4,5,5-tetramethylbiguanidium 2-(3-benzoylphenyl)propionate (slight yellow oil, yield: 92%). Measurement results of $^1$H-NMR, and a structural formula of 1-(3,4-dimethoxyphenyl)-3-phenyl-4,4,5,5-tetramethylbiguanidium 2-(3-benzoylphenyl)propionate are shown below.

$^1$H-NMR (400 MHz, CDCl$_3$) δ (ppm): 1.50 (3H, d), 2.59 (12H, s), 3.76 (1H, q), 3.78 (3H, s), 3.82 (3H, s), 6.70 (1H, d), 6.91 (1H, d), 7.00-7.03 (2H, m), 7.19 (2H, t), 7.21-7.43 (5H, m), 7.53 (1H, t), 7.59 (1H, d), 7.61 (1H, d), 7.76 (2H, d), 7.85 (1H, s), 10.80 (1H, brs).

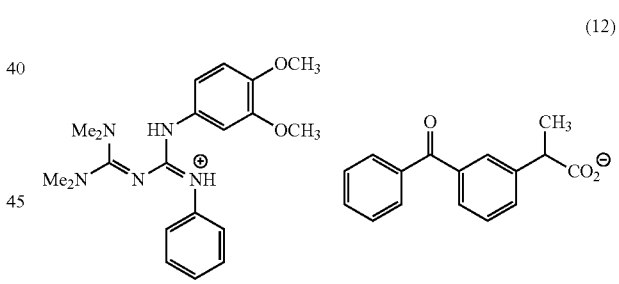

(12)

Synthetic Example 6: Synthesis of guanidium 2-(3-benzoylphenyl)propionate (Compound Represented by the Formula (101))

2.54 g of ketoprofen (10 mmol; produced by Hamari Chemicals, Ltd.) and 1.37 g of guanidine carbonate (7.6 mmol; produced by Wako Pure Chemical Industries, Ltd.), were dissolved into 3 mL of methanol, and stirred at 50° C. for 10 minutes. After completion of the reaction, reaction solution was concentrated under reduced pressure, and 5 mL of isopropanol was added to the resulting residue for recrystallization, and the crystal collected by filtration was dried under reduced pressure to obtain 2.27 g of guanidium 2-(3-benzoylphenyl)propionate (white powder, yield: 72%). Measurement results of $^1$H-NMR and $^{13}$C-NMR, and a structural formula of guanidium 2-(3-benzoylphenyl)propionate are shown below.

$^1$H-NMR (400 MHz, D$_2$O) δ (ppm): 1.29 (3H, d), 3.55 (1H, q), 7.35-7.64 (9H, m).

$^{13}$C-NMR (400 MHz, d-DMSO) δ (ppm): 19.7, 48.4, 124.3, 124.4, 126.9, 127.8, 128.4, 128.7, 129.5, 132.0, 132.4, 136.3, 137.2, 145.7, 158.8, 177.9, 195.9.

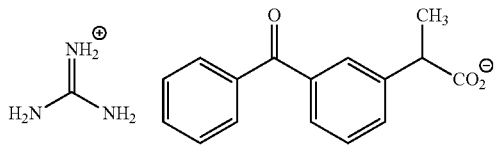

(101)

Experimental Example 1: Solubility Test for Organic Solvents and Base-Reactive Compounds Each 0.1 g of the compounds (base generators) obtained in the Examples 6 to 17, the compound (base generator) represented by the above-described formula (101) obtained in the Synthetic Example 6, and compound (base generator: 1,5,7-triazabicyclo[4.4.0]deca-5-ene 2-(9-oxoxanthene-2-yl)propionate; produced by Tokyo Chemical Industry Co., Ltd.) represented by the following formula (102) was weighed, and into these compounds, various kinds of organic solvents (PGMEA: propylene glycol monomethyl ether acetate, EL: ethyl lactate), various kinds of base-reactive compounds (SR-NPG: neopentyl glycol diglycidyl ether; produced by Sakamoto Yakuhin Kogyo, Co., Ltd., SR-TMP: trimethylolpropane polyglycidyl ether; produced by Sakamoto Yakuhin Kogyo, Co., Ltd.) and water were gradually added at room temperature, to confirm visually solubility of the compounds (base generators) to the organic solvents and the base-reactive compounds. Evaluation was conducted by the following standards: the case where the compounds (base generators) obtained in the Examples 6 to 17, the compound (base generator) represented by the above-described formula (101) obtained in the Synthetic Example 6, and the compound (base generator) represented by the following formula (102) dissolved in an additive amount of less than 1 mL of the organic solvents, the base-reactive compounds or water, was [++]; the case where these compounds (base generators) dissolved in an additive amount of 1 mL or more to less than 5 mL of the organic solvents, the base-reactive compounds or water, was [+]; the case where these compounds (base generators) dissolved in an additive amount of 5 mL or more to less than 10 mL of the organic solvents, the base-reactive compounds or water, was [−]; and the case where these compounds (base generators) dissolved only in an additive amount of 10 mL or more of the organic solvents, the base-reactive compounds or water, was [−−]. The results of solubility are shown in Table 1, as well as a structural formula of the compound represented by the formula (102) is shown below.

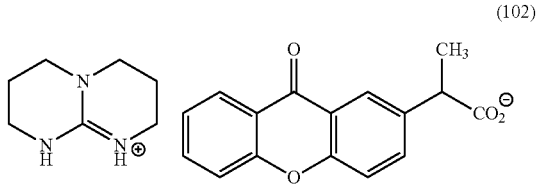

(102)

TABLE 1

| Compound | PGMEA | EL | SR-NPG | SR-TMP | H$_2$O |
| --- | --- | --- | --- | --- | --- |
| Compound represented by formula (1) | ++ | ++ | ++ | − | ++ |
| Compound represented by formula (2) | ++ | ++ | ++ | + | ++ |
| Compound represented by formula (3) | ++ | ++ | ++ | + | −− |
| Compound represented by formula (4) | ++ | + | + | + | −− |
| Compound represented by formula (5) | ++ | + | + | − | ++ |
| Compound represented by formula (6) | ++ | ++ | + | + | −− |
| Compound represented by formula (7) | + | + | + | − | ++ |
| Compound represented by formula (8) | + | + | + | − | ++ |
| Compound represented by formula (9) | ++ | ++ | ++ | + | −− |
| Compound represented by formula (10) | ++ | + | + | − | −− |
| Compound represented by formula (11) | ++ | ++ | ++ | ++ | −− |
| Compound represented by formula (12) | + | + | + | − | −− |
| Compound represented by formula (101) | −− | −− | −− | −− | ++ |
| Compound represented by formula (102) | −− | −− | −− | −− | ++ |

PGMEA: propylene glycol monomethyl ether acetate
EL: ethyl lactate
SR-NPG: neopentyl glycol diglycidyl ether
SR-TMP: trimethylolpropane polyglycidyl ether Experimental Example 2: Heat Resistance Test Each 10 mg of the compounds (base generators) obtained in the Examples 6 to 17, and the compounds (base generators) represented by the above-described formulae (101) and (102) was weighed, and weight reduction of these compounds (base generators) was measured using TG-DTA 2000 SA (manufactured by BRUKER AXS K.K.), in a range of 30° C. to 500° C. under a temperature raising speed of 10° C./min, to calculate initiation temperature of 5% weight decrease, respectively, and this temperature was used as decomposition initiation temperature to evaluate heat resistance of these compounds (base generators). The results thereof are shown in Table 2.

TABLE 2

| Compound | Decomposition initiation temperature |
|---|---|
| Compound represented by formula (1) | 191° C. |
| Compound represented by formula (2) | 189° C. |
| Compound represented by formula (3) | 219° C. |
| Compound represented by formula (4) | 199° C. |
| Compound represented by formula (5) | 204° C. |
| Compound represented by formula (6) | 205° C. |
| Compound represented by formula (7) | 200° C. |
| Compound represented by formula (8) | 206° C. |
| Compound represented by formula (9) | 168° C. |
| Compound represented by formula (10) | 181° C. |
| Compound represented by formula (11) | 204° C. |
| Compound represented by formula (12) | 177° C. |
| Compound represented by formula (101) | 161° C. |
| Compound represented by formula (102) | 247° C. |

Experimental Example 3: Exposure Curing Test Using Bisphenol A-Type Diglycidyl Ether Each 10 mg of the compounds (base generators) obtained in the Examples 6 to 17, and the compounds (base generators) represented by the above-described formulae (101) and (102) was weighed, and each of these compounds (base generators) was mixed into 100 mg of a bisphenol A-type diglycidyl ether oligomer (trade name: jER 828; produced by Mitsubishi Chemical Corp.) and 50 mg of pentaerythritol tetrakis(3-mercaptobutyrate) (trade name: KarenzMT PE1; produced by Showa Denko K.K.). The compounds (base generators) obtained in the Examples 6 to 17 dissolved into the mixed solution of the bisphenol A-type diglycidyl ether oligomer and pentaerythritol tetrakis(3-mercaptobutyrate), therefore, each of these mixed solutions was bar-coated onto a glass plate, and by irradiation of ultraviolet rays (active energy ray) for 1 minute, using an ultraviolet rays irradiation light source apparatus, that is, HLR-100T-2 (manufactured by SEN LIGHTS Corp.), having specific exposure intensity to the coated film, it was left at room temperature to cure the coated film. Hardness of the coated film was evaluated by a pencil hardness test, and curing time to give the hardness of 4H or higher was determined. On the contrary, the compounds (base generators) represented by the above-described formulae (101) and (102) did not dissolve into the mixed solution of the bisphenol A-type diglycidyl ether oligomer and pentaerythritol tetrakis(3-mercaptobutyrate), therefore, a coated film was not cured even by exposure, and it was not possible to evaluate curing time. Exposure intensity at specific wavelength of the ultraviolet rays irradiation light source apparatus HLR-100T-2 is shown in Table 3, as well as the measurement results of curing time are shown in Table 4.

TABLE 3

| Wavelength | HLR-100T-2 |
|---|---|
| 254 nm | 9.0 mW/cm$^2$ |
| 365 nm | 11.7 mW/cm$^2$ |
| 405 nm | 17.3 mW/cm$^2$ |

TABLE 4

| Compound | Curing time at room temperature |
|---|---|
| Compound represented by formula (1) | 20 to 30 min |
| Compound represented by formula (2) | 10 to 20 min |
| Compound represented by formula (3) | 20 to 30 min |
| Compound represented by formula (4) | 20 to 30 min |
| Compound represented by formula (5) | 20 to 30 min |
| Compound represented by formula (6) | 20 to 30 min |
| Compound represented by formula (7) | 20 to 30 min |
| Compound represented by formula (8) | 60 to 70 min |
| Compound represented by formula (9) | 30 to 40 min |
| Compound represented by formula (10) | 30 to 40 min |
| Compound represented by formula (11) | 30 to 40 min |
| Compound represented by formula (12) | 30 to 40 min |
| Compound represented by formula (101) | Not evaluable due to not dissolving |
| Compound represented by formula (102) | Not evaluable due to not dissolving |

Experimental Example 4: Exposure Curing Test Using an Acrylate

Each 10 mg of the compounds (base generators) obtained in the Examples 6, 10, 12 and 13, and the compound (base generator) represented by the above-described formula (101) was weighed, and each of these compounds (base generators) was mixed into 100 mg of dipentaerythritol (trade name: KAYARAD DPHA; produced by Nippon Kayaku Co., Ltd.). Each of these mixed solutions prepared was bar-coated onto a glass plate, and by irradiation of ultraviolet rays (active energy ray) for 10 seconds, using an ultraviolet rays irradiation light source apparatus, that is, REX-250 (manufactured by Asahi Spectra Co., Ltd.), having specific exposure intensity to the coated film, the coated film was cured. Pencil hardness of the coated film was measured by a pencil hardness test. Exposure intensity at specific wavelength of the ultraviolet rays irradiation light source apparatus REX-250 is shown in Table 5, as well as the measurement results of pencil hardness are shown in Table 6.

Experimental Example 5: Exposure Gelation Test Using Acrylamide in Water

Each 10 mg of the compounds (base generators) obtained in the Examples 6, 10, 12 and 13, and the compound (base generator) represented by the above-described formula (101) was weighed, and each of these compounds (base generators) was mixed into 100 mg of acrylamide (produced by Wako Pure Chemical Industries, Ltd.) and 50 mg of water. Each of these mixed solutions prepared was bar-coated onto a glass plate, and by irradiation of ultraviolet rays (active energy ray) for 10 seconds, using an ultraviolet rays irradiation light source apparatus, that is, REX-250 (manufactured by Asahi Spectra Co., Ltd.), having specific exposure intensity to the coated film, a polymer gel was obtained. Evaluation was conducted by the following standards: the case where acrylamide gel was obtained by polymerization of acrylamide, was [○]; and the case where acrylamide gel was not obtained, was [x]. The results thereof are shown in Table 6.

TABLE 5

| Wavelength | REX-250 |
|---|---|
| 254 nm | 0 mW/cm$^2$ |
| 365 nm | 55.0 mW/cm$^2$ |
| 405 nm | 31.0 mW/cm$^2$ |

TABLE 6

| Compound | Example 4 Pencil hardness | Example 5 Presence or absence of gelation |
|---|---|---|
| Compound represented by formula (1) | 3H | ○ |
| Compound represented by formula (5) | <6B | x |
| Compound represented by formula (7) | 3H | ○ |
| Compound represented by formula (8) | <6B | x |
| Compound represented by formula (101) | Not evaluable due to not dissolving | ○ |

Experimental Example 6: Exposure Curing Test Using a Sol-Gel-Reaction

Each 10 mg of the compound (base generator) obtained in the Example 6, and the compounds (photo-acid generators; both produced by Wako Pure Chemical Industries, Ltd.) represented by the following formulae (103) and (104) was weighed, and each of these compounds was mixed into 200 mg of a propylene glycol monomethyl ether acetate (PG-MEA) solution of 28% poly-3-(trimethoxysilyl)propyl methacrylate (produced by Wako Pure Chemical Industries, Ltd., Mw=15000). It should be noted that into the compounds represented by the formulae (103) and (104), 5 mg of 2-isopropylthioxanthone represented by the following formula (105) was added, as a sensitizer. Each of these mixed solutions prepared was bar-coated onto a glass plate, and the coated film was pre-baked at 80° C. for 1 minute. After irradiation of ultraviolet rays (active energy ray) with arbitrary exposure amount, using an ultraviolet rays irradiation light source apparatus, that is, REX-250 (manufactured by Asahi Spectra Co., Ltd.), having specific exposure intensity to the resulting coated film, the coated film was heated at 80° C. for 5 minutes. Exposure amount to the coated film was determined in the case where the coated film remained not dissolved in acetone, after immersing the coated film in acetone for 1 minute. The exposure amounts to the coated film are shown in Table 7, as well as structural formulae of the compounds (photo-acid generators) represented by the formulae (103) and (104), and the compound (sensitizer) represented by the formula (105) are shown below.

TABLE 7

| Compound | Exposure amount |
|---|---|
| Compound represented by formula (1) | 27 mJ/cm² |
| Photo-acid generator represented by formula (103) and sensitizer represented by formula | 55 mJ/cm² |
| Photo-acid generator represented by formula (104) and sensitizer represented by formula | 165 mJ/cm² |

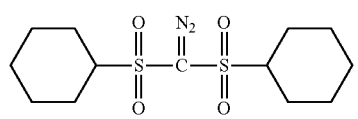

(103)

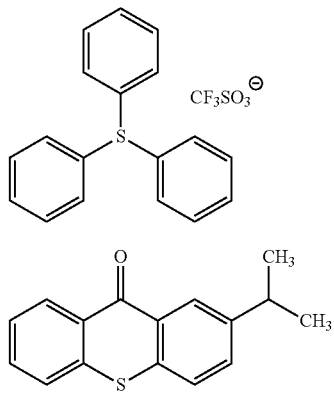

(104)

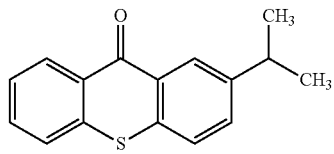

(105)

It was found, from the results of Experimental Example 1 and Experimental Example 3, that a conventionally known base generator is difficult to provide a pattern with high contrast, caused by poor solubility even by making the base generator contained in a resin composition, because of having poor solubility to an organic solvent and a base-reactive compound, however, the compound (base generator) represented by the general formula (A) of the present invention is capable of providing a pattern with high contrast, and providing the base generator having high general-purpose, because of having good solubility to an organic solvent and a base-reactive compound generally used in this field. In particular, it was found that the compound (base generator) represented by the general formula (A) of the present invention has superior effect of enabling to be used also in a composition not containing an organic solvent, because of having high solubility also to a base-reactive compound. In addition, it was found, from the result of Experimental Example 3, that the compound (base generator) represented by the general formula (A) of the present invention generates a sufficiently strong base (biguanides) by irradiation of active energy ray having a wavelength of 200 nm or longer, and is capable of providing a cured resin composed of a base-reactive compound, by making the compound (base generator) represented by the general formula (A) of the present invention reacted with the base-reactive compound. In addition, it was found, from the result of Experimental Example 2, that the compound (base generator) represented by the general formula (A) of the present invention is relatively stable to heat, because it is a compound having a decomposition initiation temperature of over 150° C. Therefore, in the case where the base generator of the present invention was used, not only there is advantage be capable of setting baking temperature high and using an organic solvent having high boiling point, but also the residue of the organic solvent can be decreased as small as possible, after baking. In this way, deterioration of contrast between an exposed area (cured area) and an unexposed area (uncured area), caused by the remaining organic solvent, can be suppressed. Still more, it was found, from the result of Experimental Example 6, that the compound (base generator) represented by the general formula (A) of the present invention can generate biguanides, in an amount sufficient to cure an alkoxysilyl compound, under less photo energy, and has high sol-gel reactivity, therefore it is a suitable compound for curing these compounds, because biguanides generating from the compound (base generator) represented by the general formula (A) of the present invention are capable of curing the alkoxysilyl compound under smaller exposure amount (less photo energy), as compared with a strong acid generating from a conventional photo-acid generator. Still more, it was found, from the results of Experimental Example 4 and Experimental Example 5, that among the compounds represented by the general formula (A) of the present invention, the compound represented by the general formula (E) having a benzophenone skeleton, has radical curing performance, because it is capable of curing an acrylate which reacts with a radical, and it is a radical generator which is applicable also to an aqueous radical photo-curing system. It was found that, from the above results, the compound represented by the general formula (A) of the present invention is the compound useful, for example, as the base generator and the radical generator for resin curing.

INDUSTRIAL APPLICABILITY

The compound represented by the general formula (A) of the present invention and the base generator of the present invention are those which generate a strong base (biguanides) by irradiation of active energy ray, have high solubility to organic solvents generally used in this field, such as, for example, a glycol ether acetate-based solvent, an ester-based solvent, etc., as well as capable of directly dissolving into base-reactive compounds, such as an epoxy-based compound, and have both performance of high heat resistance and low nucleophilicity, therefore is the compound useful, for example, as the base generator for curing the base-reactive compound such as, for example, the epoxy-based compound, etc., where a curing reaction is difficult to progress.

The base-reactive composition of the present invention is a composition comprising the base generator of the present invention, and is capable of preparing a cured film or a molded article without using an organic solvent, depending on conditions, and is thus the composition useful, for example, for a paint, a printing ink, a dental material, an optical material, such as resist, an electronic material, etc.

The method for generating a base of the present invention is a method which uses the compound represented by the general formula (A) of the present invention, and is a method capable of generating a strong base (biguanides) in good efficiency by irradiating active energy ray, for example, ultraviolet rays, visible rays, infrared rays, X-rays.

The invention claimed is:

1. A compound of formula (A') or (A''):

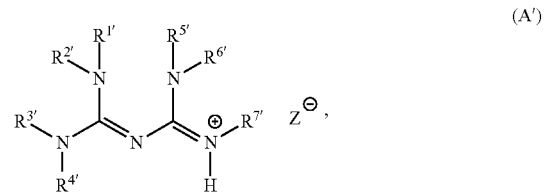

wherein $R^{1'}$ to $R^{5'}$ each independently is an alkyl group having 1 to 8 carbon atoms, $R^{6'}$ is a hydrogen atom; an alkyl group having 1 to 6 carbon atoms which may have a substituent selected from the group consisting of an epoxy group, an alkoxycarbonyl group having 2 to 6 carbon atoms, a coumarinylcarbonyl group, an anthraquinonyl group, a xanthonyl group and a thioxanthonyl group; an alkenyl group having 2 to 6 carbon atoms; or an arylalkyl group having 7 to 15 carbon atoms which may have a substituent selected from the group consisting of an alkyl group having 1 to 6 carbon atoms, an alkoxy group having 1 to 6 carbon atoms, a halogen atom, and a nitro group, $R^{7'}$ is an alkyl group having 1 to 8 carbon atoms which may have an amino group, and $Z^-$ is an anion derived from a carboxylic acid of formula $(B_1)$, $(B_2)$, $(B_3)$ or $(B_4)$;

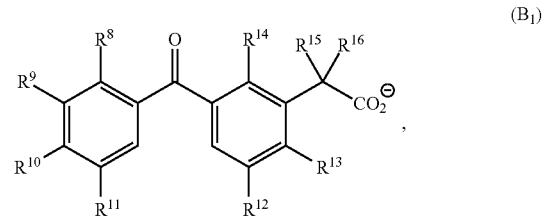

wherein $R^8$ to $R^{16}$ each independently is a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group;

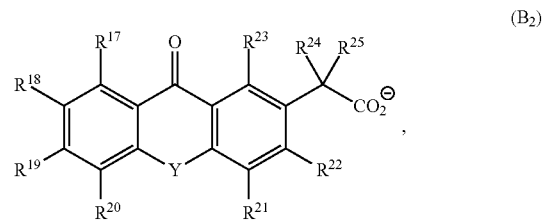

wherein $R^{17}$ to $R^{25}$ each independently is a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, and Y is an oxygen atom or a sulfur atom;

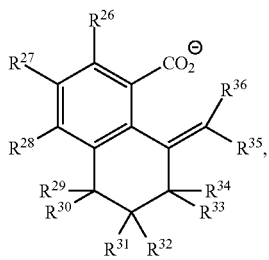

wherein $R^{26}$ to $R^{36}$ each independently is a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, and two pieces of R may form a ring structure by binding to each other;

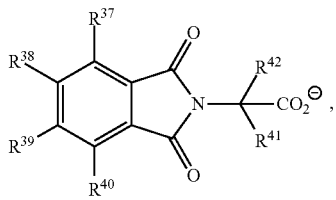

wherein $R^{37}$ to $R^{42}$ each independently is a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, and two pieces of R may form a ring structure by binding to each other;

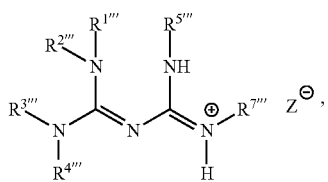

wherein $R^{1'''}$ to $R^{4'''}$ each independently is an alkyl group having 1 to 8 carbon atoms, $R^{5'''}$ is an alkyl group having 1 to 10 carbon atoms or an aryl group having 6 to 14 carbon atoms which may have a substituent selected from the group consisting of an alkyl group having 1 to 6 carbon atoms, an alkoxy group having 1 to 6 carbon atoms, a halogen atom, and a nitro group, $R^{7'''}$ is an aryl group having 6 to 14 carbon atoms which may have a substituent selected from the group consisting of an alkyl group having 1 to 6 carbon atoms, an alkoxy group having 1 to 6 carbon atoms, a halogen atom, and a nitro group, and $Z^-$ is the same as described above.

2. The compound according to claim 1, wherein the anion $Z^-$ derived from a carboxylic acid in the general formula (A') or (A'') is an anion of formula (B$_1$'), (B$_2$'), (B$_3$') or (B$_4$'):

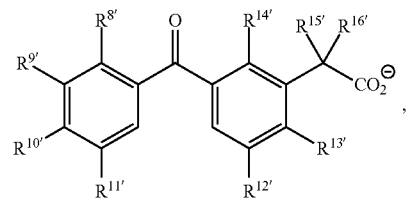

wherein $R^{8'}$ to $R^{16'}$ each independently is a hydrogen atom or an alkyl group having 1 to 4 carbon atoms;

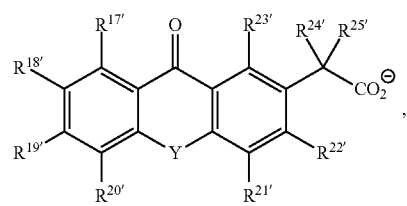

wherein $R^{17'}$ to $R^{25'}$ each independently is a hydrogen atom or an alkyl group having 1 to 4 carbon atoms, and Y is an oxygen atom or a sulfur atom;

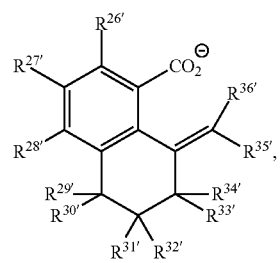

wherein $R^{26'}$, $R^{27'}$, and $R^{29'}$ to $R^{36'}$ each independently is a hydrogen atom or an alkyl group having 1 to 4 carbon atoms, and $R^{28'}$ is a hydrogen atom or an alkoxy group having 1 to 4 carbon atoms;

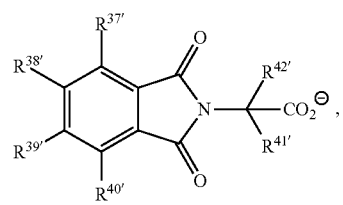

wherein $R^{37'}$ to $R^{42'}$ each independently is a hydrogen atom or an alkyl group having 1 to 4 carbon atoms.

3. The compound according to claim 1, wherein the compound of formula (A) is a compound of formula (1), (2), (3), (4), (5), (6), (7), (8), (9), (10), (11) or (12):

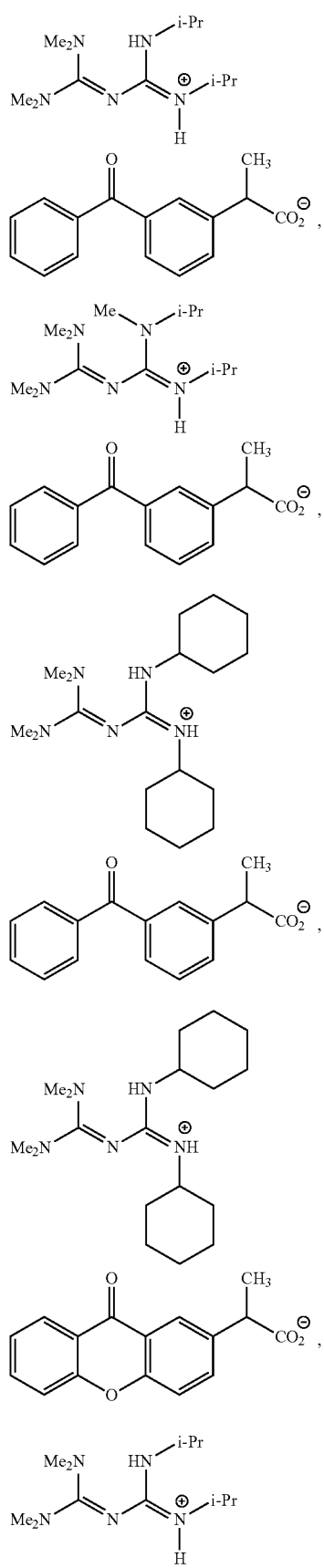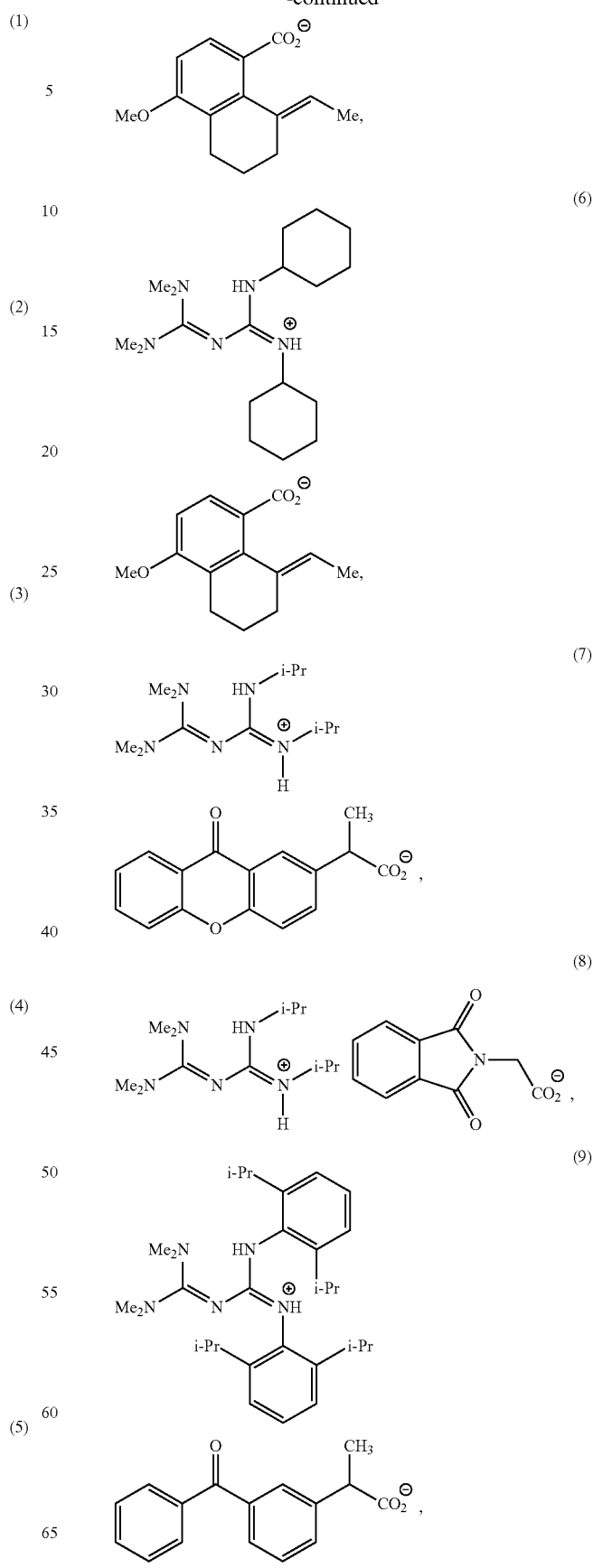

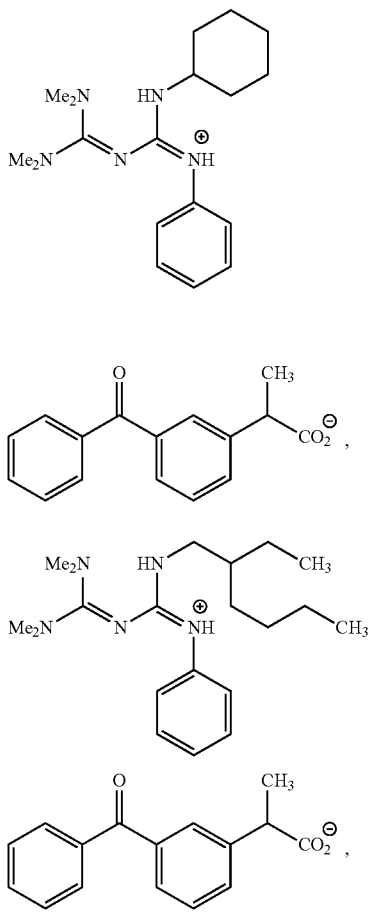

(10)

(11)

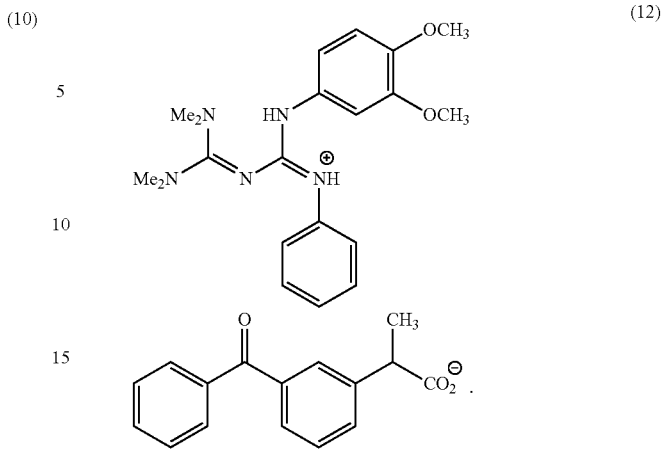

(12)

4. A base generator comprising the compound according to claim 1.

5. The base generator according to claim 4, which is a base generator generating a base by irradiation of active energy ray.

6. A base-reactive composition, which comprises the base generator according to claim 4 and a base-reactive compound, wherein the base reactive compound is a compound selected from the group consisting of an epoxy-based compound, a silicon-based compound, an isocyanate-based compound, and a polyamic acid-based compound.

7. The base-reactive composition according to claim 6, wherein the composition is a composition further comprising an organic solvent.

8. A method for generating a base, which comprises irradiating active energy ray having a wavelength of 100 to 700 nm to the compound according to claim 1 for an irradiation time of 0.01 to 1,000 seconds.

* * * * *